(12) United States Patent
Lewin et al.

(10) Patent No.: US 12,203,074 B2
(45) Date of Patent: Jan. 21, 2025

(54) COMPOSITIONS AND METHODS FOR TREATMENT OF DOMINANT RETINITIS PIGMENTOSA

(71) Applicants: University of Florida Research Foundation, Incorporated, Gainesville, FL (US); The Trustees of the University of Pennsylvania, Philadelphia, PA (US)

(72) Inventors: Alfred S. Lewin, Gainesville, FL (US); William W. Hauswirth, Gainesville, FL (US); Michael T. Massengill, Gainesville, FL (US); William Beltran, Wynnewood, PA (US); Gustavo D. Aguirre, Media, PA (US); Artur Cideciyan, Lafayette Hill, PA (US); Samuel Jacobson, Penn Valley, PA (US)

(73) Assignees: University of Florida Research Foundation, Incorporated, Gainesville, FL (US); The Trustees of the University of Pennsylvania, Philadelphia, PA (US)

( * ) Notice: Subject to any disclaimer, the term of this patent is extended or adjusted under 35 U.S.C. 154(b) by 984 days.

(21) Appl. No.: 17/059,815

(22) PCT Filed: Jun. 3, 2019

(86) PCT No.: PCT/US2019/035159
§ 371 (c)(1),
(2) Date: Nov. 30, 2020

(87) PCT Pub. No.: WO2019/232517
PCT Pub. Date: Dec. 5, 2019

(65) Prior Publication Data
US 2021/0207147 A1 Jul. 8, 2021

Related U.S. Application Data

(60) Provisional application No. 62/809,539, filed on Feb. 22, 2019, provisional application No. 62/679,585, filed on Jun. 1, 2018.

(51) Int. Cl.
*C12N 15/113* (2010.01)
*C12N 15/86* (2006.01)

(52) U.S. Cl.
CPC .......... *C12N 15/1138* (2013.01); *C12N 15/86* (2013.01); *C12N 2310/121* (2013.01); *C12N 2310/122* (2013.01); *C12N 2310/14* (2013.01); *C12N 2320/32* (2013.01); *C12N 2750/14142* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 7,138,378 B1 | 11/2006 | Farrar et al. | |
| 8,450,473 B2 * | 5/2013 | Sullivan | A61P 43/00 536/24.5 |
| 8,551,970 B2 | 10/2013 | Farrar et al. | |
| 11,118,185 B2 | 9/2021 | Lewin et al. | |
| 2007/0009899 A1 | 1/2007 | Mounts | |
| 2013/0064815 A1 | 3/2013 | Coller | |
| 2015/0159171 A1 | 6/2015 | Deglon | |
| 2017/0096683 A1* | 4/2017 | Scaria | C07K 14/015 |
| 2017/0173183 A1 | 6/2017 | O'Riordan et al. | |
| 2017/0348387 A1 | 12/2017 | Aquirre et al. | |
| 2018/0043034 A1 | 2/2018 | Pierce et al. | |
| 2019/0093111 A1 | 3/2019 | Lewin et al. | |
| 2021/0324387 A1 | 5/2021 | Lewin et al. | |

FOREIGN PATENT DOCUMENTS

| | | | |
|---|---|---|---|
| CN | 102061305 A | 5/2011 | |
| CN | 102061308 A | 5/2011 | |
| CN | 102061305 B * | 7/2012 | |
| CN | 105960413 A | 9/2016 | |
| JP | 2006-523464 A | 10/2006 | |
| JP | 2007-530431 A | 11/2007 | |
| JP | 2010-518821 A | 6/2010 | |
| WO | WO 2004/020631 A2 | 3/2004 | |
| WO | WO-2004022722 A2 * | 3/2004 | A01K 67/0275 |

(Continued)

OTHER PUBLICATIONS

Massengill et al., "Tandem Delivery of Short Hairpin RNAs and Rhodopsin cDNA to Combat Retinal Degeneration in Autosomal Dominant Retinitis Pigmentosa", IOVS, vol. 58, 4082, Published Jun. 2017. (Year: 2017).*

Palfi et al., "Adeno-Associated Virus-Mediated Rhodopsin Replacement Provides Therapeutic Benefit in Mice with a Targeted Disruption of the *Rhodopsin* Gene", Human Gene Therapy, vol. 21, Published Mar. 2010, pp. 311-321. (Year: 2010).*

(Continued)

*Primary Examiner* — Brian Whiteman
*Assistant Examiner* — Stephanie L Sullivan
(74) *Attorney, Agent, or Firm* — Wolf, Greenfield & Sacks, P.C.

(57) ABSTRACT

Aspects of the disclosure relate to methods and compositions useful for treating retinitis pigmentosa. In some aspects, the disclosure provides compositions and methods for delivering an interfering RNA to a subject in order to reduce expression of one or both alleles of an endogenous RHO gene (for example a mutant rho allele associated with retinitis pigmentosa) in a subject. In some embodiments, a replacement RHO coding sequence that is resistant to the interfering RNA also is delivered to the subject.

20 Claims, 45 Drawing Sheets

Specification includes a Sequence Listing.

(56) References Cited

FOREIGN PATENT DOCUMENTS

| | | |
|---|---|---|
| WO | WO 2004/094606 A2 | 11/2004 |
| WO | WO 2005/090572 A2 | 9/2005 |
| WO | WO 2008/100627 A2 | 8/2008 |
| WO | WO 2008/125846 A2 | 10/2008 |
| WO | WO 2009/035792 A1 | 3/2009 |
| WO | WO 2010/127209 A2 | 11/2010 |
| WO | WO 2014/138792 A1 | 9/2014 |
| WO | WO 2015/075154 A2 | 5/2015 |
| WO | WO 2015/143418 A2 | 9/2015 |
| WO | WO 2016/138353 A1 | 9/2016 |
| WO | WO 2016/176690 A2 | 11/2016 |
| WO | WO 2017/137493 A1 | 8/2017 |
| WO | WO 2017/151823 A1 | 9/2017 |

OTHER PUBLICATIONS

Plotkin et al., "Tissue-specific codon usage and the expression of human genes", PNAS, vol. 101, Published Aug. 24, 2004, pp. 12588-12591. (Year: 2004).*

Latella et al., "In vivo editing of human mutant *Rhodopsin* Gene by Electroporation of Plasmid-based CRISPR/Cas9 in the mouse Retina", Molecular Therapy-Nucleic Acids, Published Nov. 22, 2016, pp. 1-12. (Year: 2016).*

Bethke, "The Future of Gene Therapy", Review of Opthalmology, Published Apr. 5, 2016, retrieved on Jun. 27, 2024, retrieved from the Internet: < https://www.reviewofophthalmology.com/article/the-future-of-gene-therapy>. (Year: 2016).*

Supplementary Partial European Search Report for Application No. EP 17760752.0, mailed Jul. 5, 2019.

Extended European Search Report for Application No. EP 17760752.0, mailed Oct. 15, 2019.

Extended European Search Report for Application No. EP 22170988.4, mailed Dec. 19, 2022.

International Search Report and Written Opinion for Application No. PCT/US2017/020289, mailed Jul. 19, 2017.

International Preliminary Report on Patentability for Application No. PCT/US2017/020289, mailed Sep. 13, 2018.

Extended European Search Report for Application No. EP 19812143.6 mailed Sep. 16, 2022.

International Search Report and Written Opinion for Application No. PCT/US2019/035159, mailed Sep. 12, 2019.

International Preliminary Report on Patentability for Application No. PCT/US2019/035159 mailed Dec. 10, 2020.

[No Author Listed], GenBank Accession No. M55171.2. Mouse opsin (MOPS) gene, complete cds. Jun. 9, 2017. 4 pages.

Athanasiou et al., The molecular and cellular basis of rhodopsin retinitis pigmentosa reveals potential strategies for therapy. Prog Retin Eye Res. Jan. 2018:62:1-23. doi: 10.1016/j.preteyeres.2017.10.002. Epub Oct. 16, 2017. Author manuscript, 58 pages.

Behrman et al., A CHOP-regulated microRNA controls rhodopsin expression. J Cell Biol. Mar. 21, 2011; 192(6):919-27. doi: 10.1083/jcb.201010055. Epub Mar. 14, 2011.

Beltran et al., Optimization of Retinal Gene Therapy for X-Linked Retinitis Pigmentosa Due to RPGR Mutations. Mol Ther. Aug. 2, 2017;25(8):1866-1880. doi: 10.1016/j.ymthe.2017.05.004. Epub May 27, 2017.

Bennett et al., Taking Stock of Retinal Gene Therapy: Looking Back and Moving Forward. Mol Ther. May 3, 2017;25(5):1076-1094. doi: 10.1016/j.ymthe.2017.03.008. Epub Apr. 5, 2017.

Brummelkamp et al., A system for stable expression of short interfering RNAs in mammalian cells. Science. Apr. 19, 2002;296(5567):550-3. doi: 10.1126/science.1068999. Epub Mar. 21, 2002.

Burnight et al., Using CRISPR-Cas9 to Generate Gene-Corrected Autologous iPSCs for the Treatment of Inherited Retinal Degeneration. Mol Ther. Sep. 6, 2017;25(9):1999-2013. doi: 10.1016/j.ymthe.2017.05.015. Epub Jun. 12, 2017.

Cashman et al., Towards mutation-independent silencing of genes involved in retinal degeneration by RNA interference. Gene Ther. Aug. 2005;12(15):1223-8. doi: 10.1038/sj.gt.3302512.

Dunbar et al., Gene therapy comes of age. Science. Jan. 12, 2018;359(6372):eaan4672. doi: 10.1126/science.aan4672.

Froebel et al., Effects of Pathogenic Variations in the Human Rhodopsin Gene (hRHO) on the Predicted Accessibility for a Lead Candidate Ribozyme. Invest Ophthalmol Vis Sci. Jul. 1, 2017; 58(9):3576-3591. doi: 10.1167/iovs.16-20877.

Gorbatyuk et al., Suppression of mouse rhodopsin expression in vivo by AAV mediated siRNA delivery. Vision Res. Apr. 2007;47(9):1202-8. doi: 10.1016/j.visres.2006.11.026. Epub Feb. 12, 2007. PMID: 17292939; PMCID: PMC1892214.

Guziewicz et al., BEST1 gene therapy corrects a diffuse retina-wide microdetachment modulated by light exposure. Proc Natl Acad Sci U S A. Mar. 20, 2018;115(12):E2839-E2848. doi: 10.1073/pnas.1720662115. Epub Mar. 5, 2018.

Iwabe et al., Assessment of visual function and retinal structure following acute light exposure in the light sensitive T4R rhodopsin mutant dog. Exp Eye Res. May 2016;146:341-353. doi: 10.1016/j.exer.2016.04.006. Epub Apr. 13, 2016. Author Manuscript.

Jiang et al., Retinitis pigmentosa associated *Rhodopsin* gene; Intl Review of Ophthalmology. Dec. 22, 2014;38(6):391-394.

Lewin et al., Gene augmentation for adRP mutations in RHO. Cold Spring Harb Perspect Med. Jul. 18, 2014;4(9):a017400. doi: 10.1101/cshperspect.a017400.

Mao et al., Long-term rescue of retinal structure and function by rhodopsin RNA replacement with a single adeno-associated viral vector in P23H RHO transgenic mice. Hum Gene Ther. Apr. 2012;23(4):356-66. doi: 10.1089/hum.2011.213. Epub Mar. 28, 2012.

Millington-Ward et al., Suppression and replacement gene therapy for autosomal dominant disease in a murine model of dominant retinitis pigmentosa. Mol Ther. Apr. 2011;19(4):642-9. doi: 10.1038/mt.2010.293. Epub Jan. 11, 2011.

Murray et al., Allele-Specific Inhibition of Rhodopsin With an Antisense Oligonucleotide Slows Photoreceptor Cell Degeneration. Invest Ophthalmol Vis Sci. Oct. 2015; 56(11):6362-75. doi: 10.1167/iovs.15-16400.

O'Keefe, siRNAs and shRNAs: Tools for protein knockdown by gene silencing. Mater Methods. 2013;3(197). Jul. 7, 2017 (Jul. 7, 2017), XP055956975, Retrieved from the Internet: URL:https://web.archive.org/web/20170707171841/https://www.labome.com/method/siRNAsand-shRNAs-Tools-for-Protein-Knockdown-byGene-Silencing.html [retrieved on Sep. 1, 2022].

Rosas et al., Patterns of scAAV vector insertion associated with oncogenic events in a mouse model for genotoxicity. Mol Ther. Nov. 2012; 20(11):2098-110. doi: 10.1038/mt.2012.197. Epub Sep. 18, 2012.

Stanton et al., Novel pathogenic mutations in C1QTNF5 support a dominant negative disease mechanism in late-onset retinal degeneration. Sci Rep. Sep. 22, 2017;7(1):12147. doi: 10.1038/s41598-017-11898-3.

Sudharsan et al., Acute and Protracted Cell Death in Light-Induced Retinal Degeneration in the Canine Model of Rhodopsin Autosomal Dominant Retinitis Pigmentosa. Invest Ophthalmol Vis Sci. Jan. 1, 2017;58(1):270-281. doi: 10.1167/iovs.16-20749.

* cited by examiner

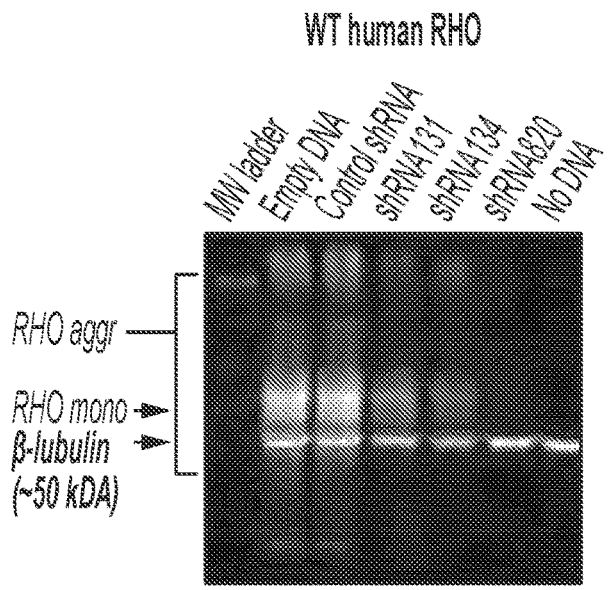
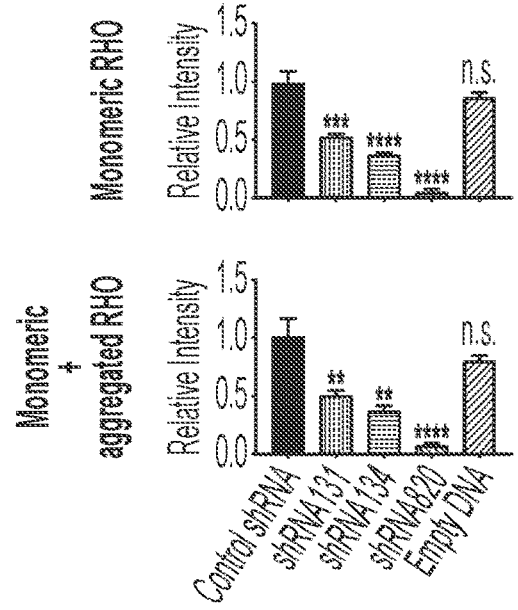
FIG. 1A
FIG. 1B
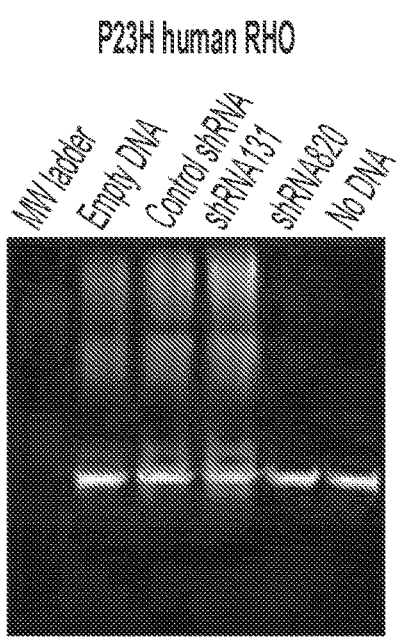
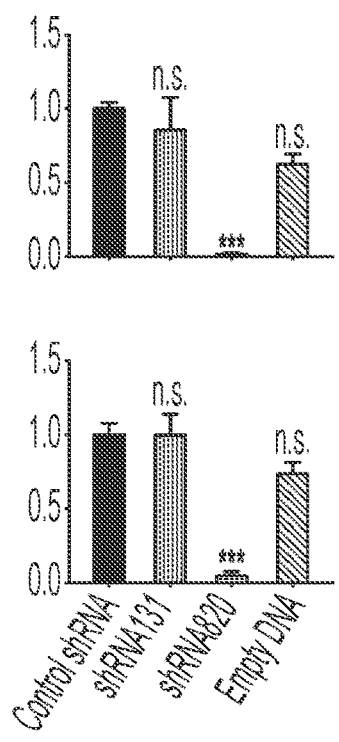
FIG. 1C
FIG. 1D

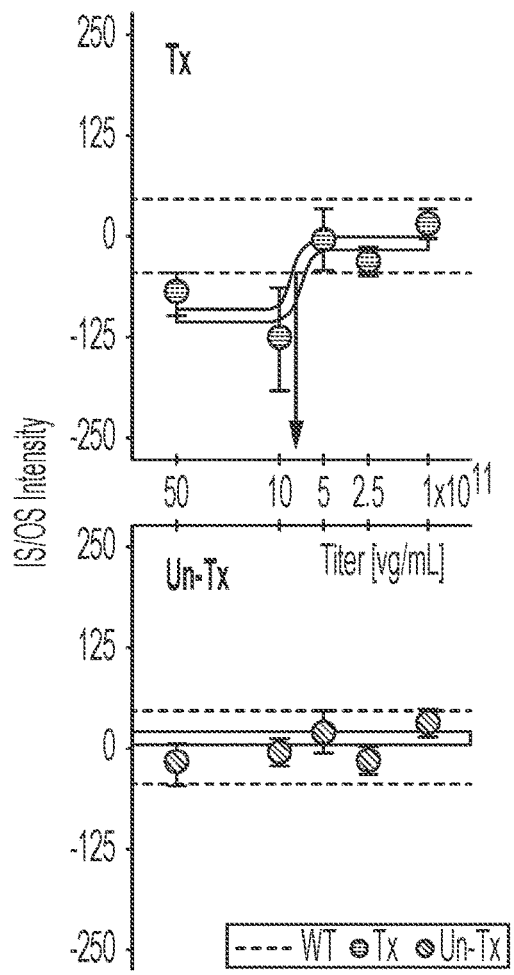
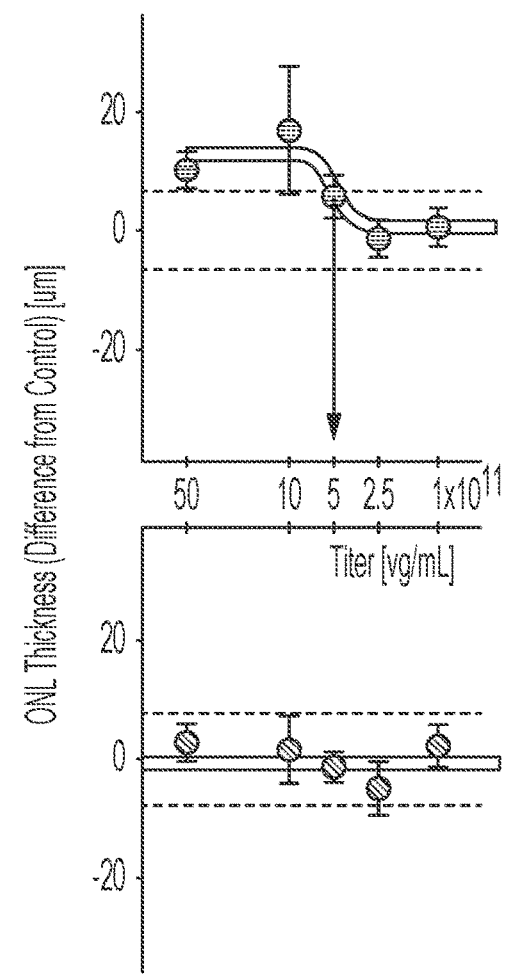
FIG. 2D  FIG. 2E
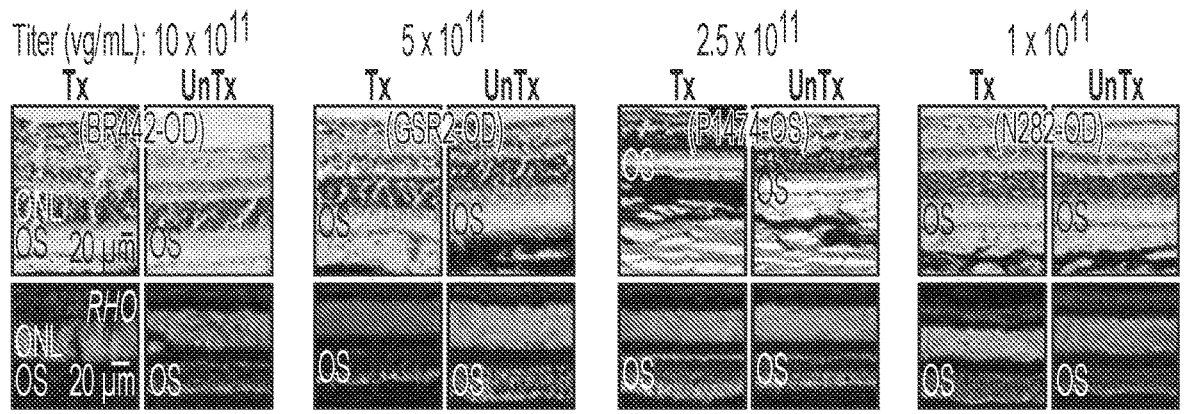
FIG. 2F

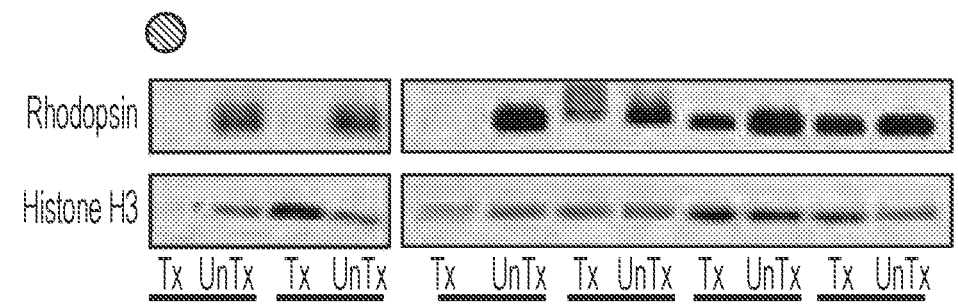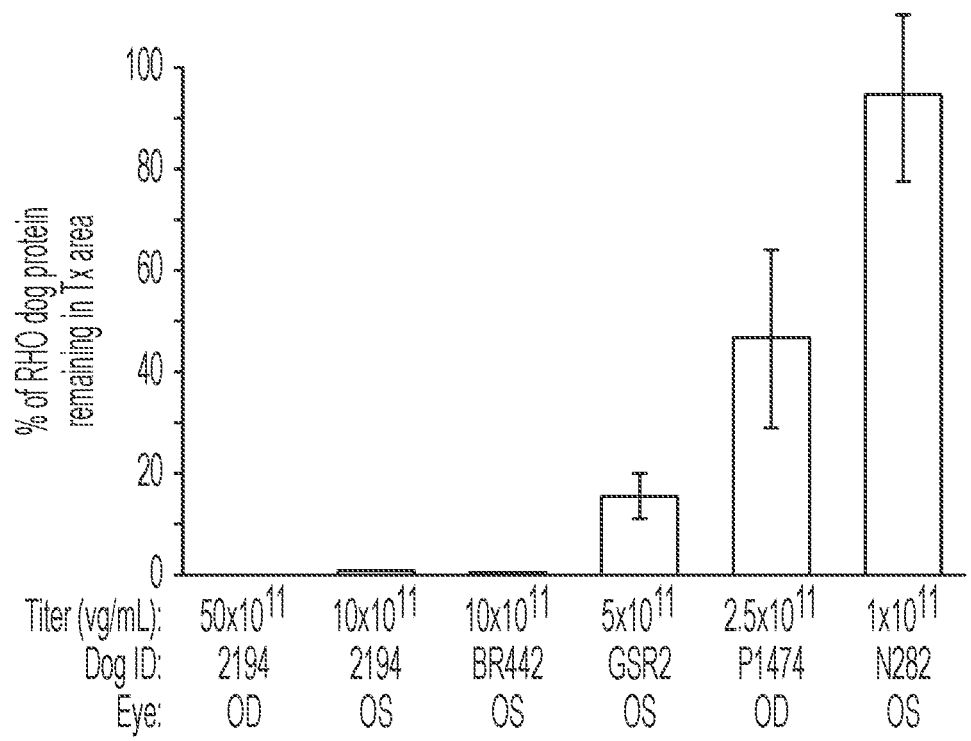
FIG. 2H (continued)

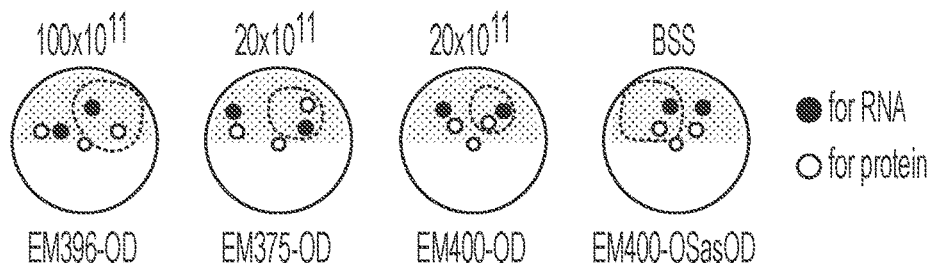
FIG. 10A
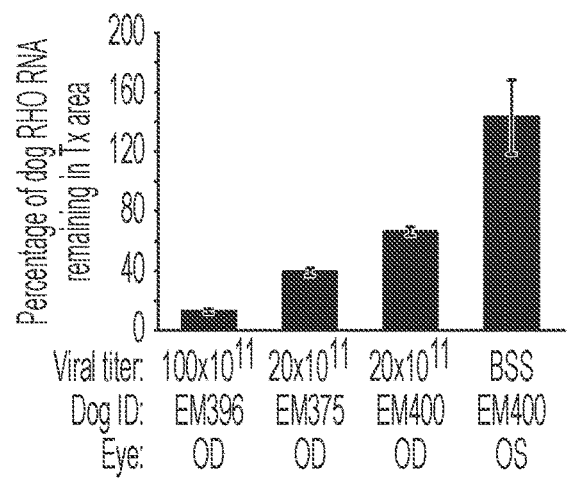
FIG. 10B
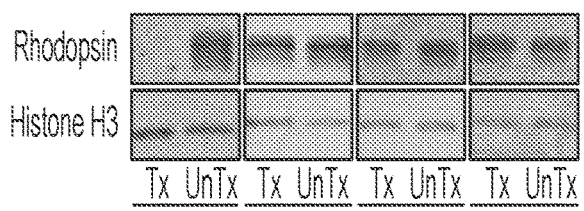
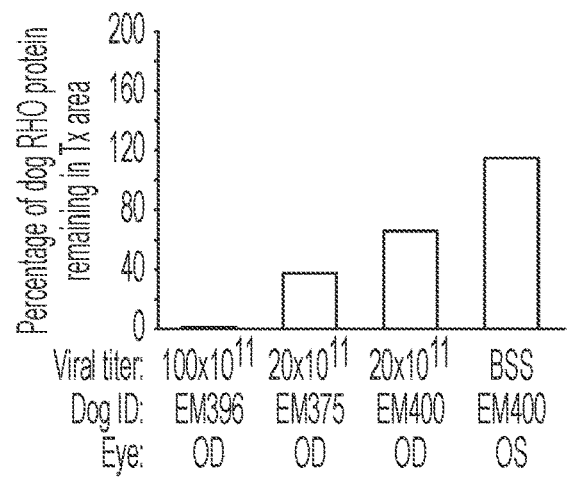
FIG. 10C

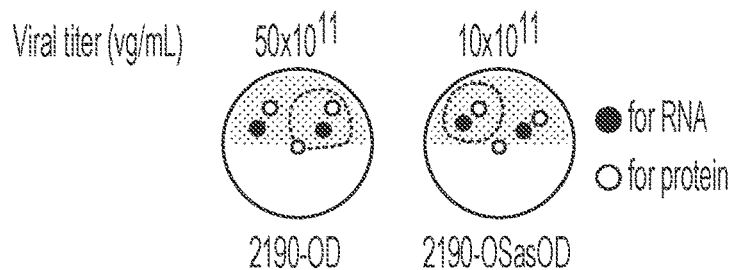
FIG. 11A
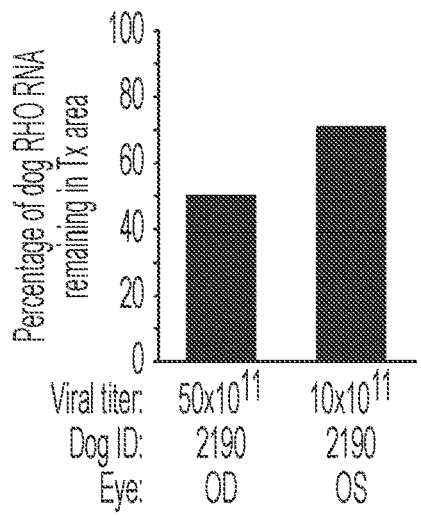
FIG. 11B
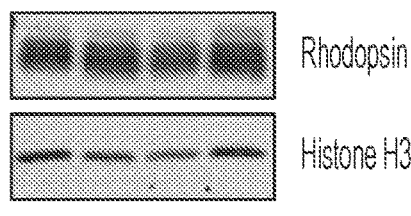
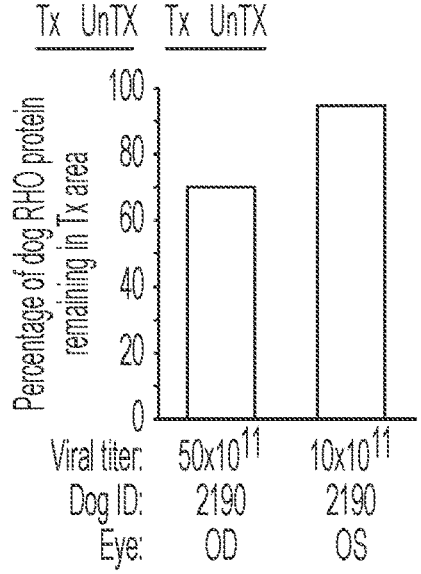
FIG. 11C

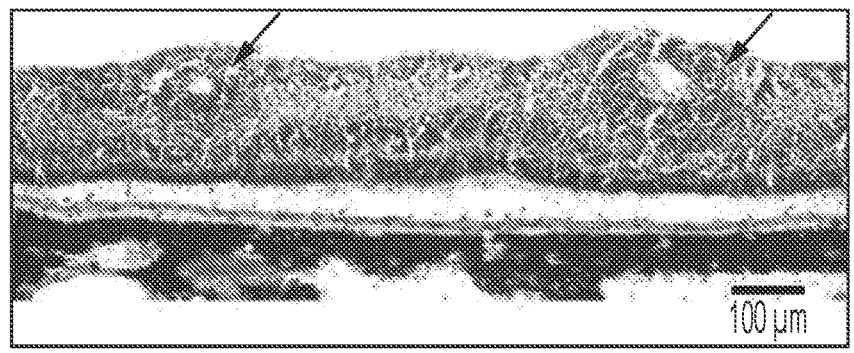
FIG. 13F
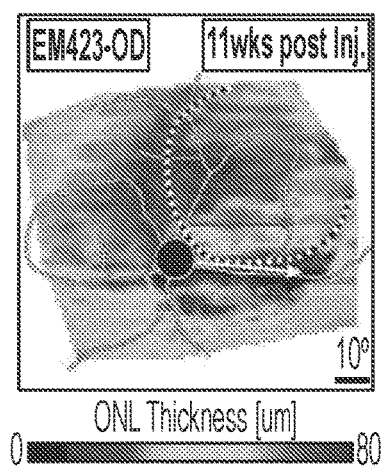 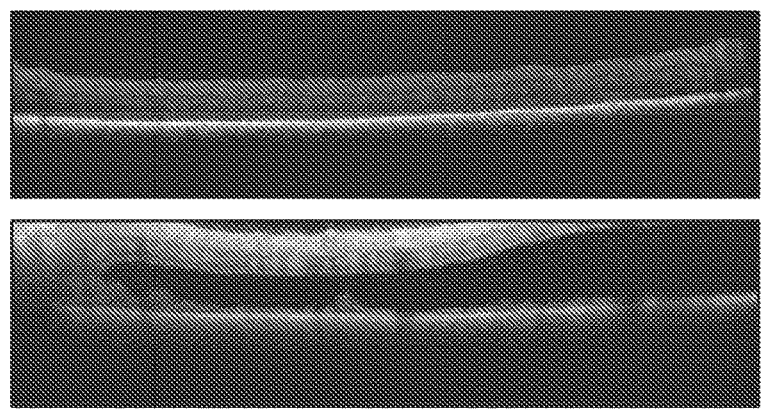
FIG. 13G

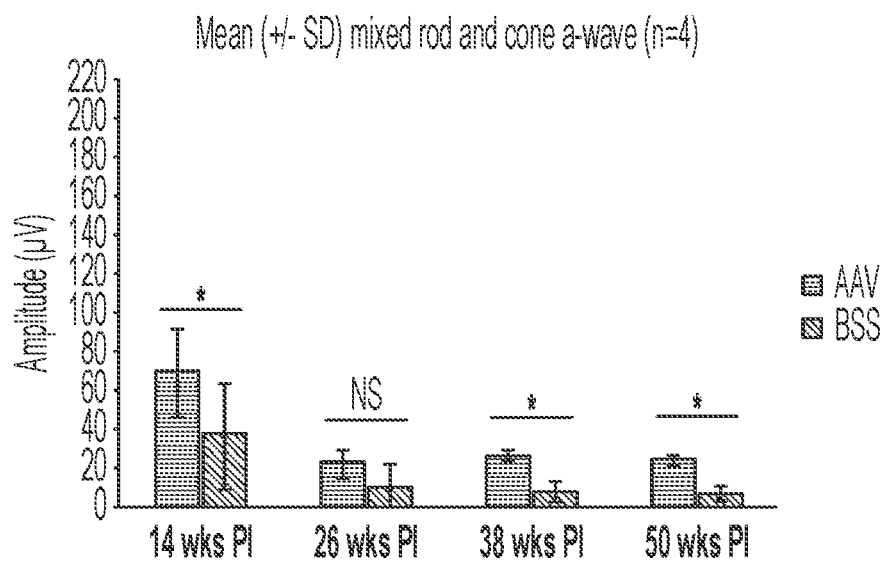
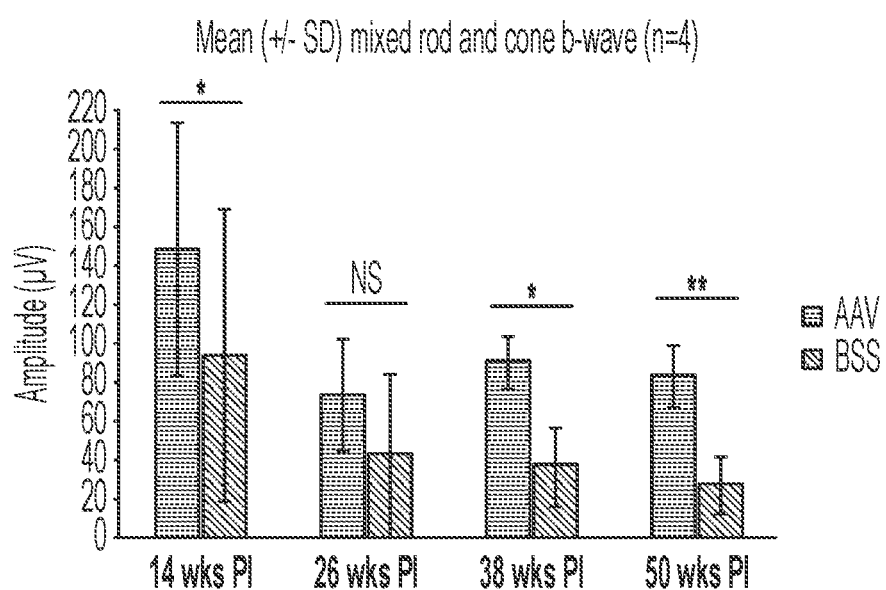
FIG. 19B

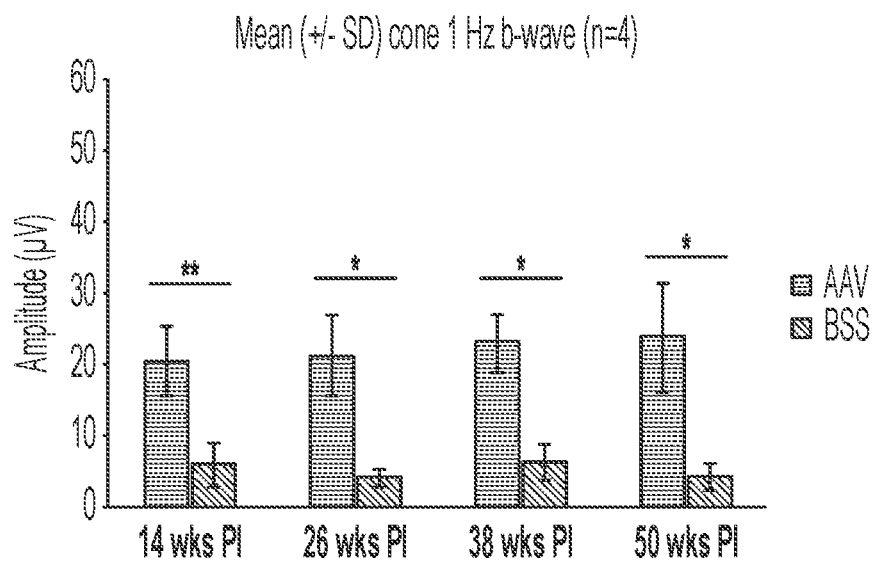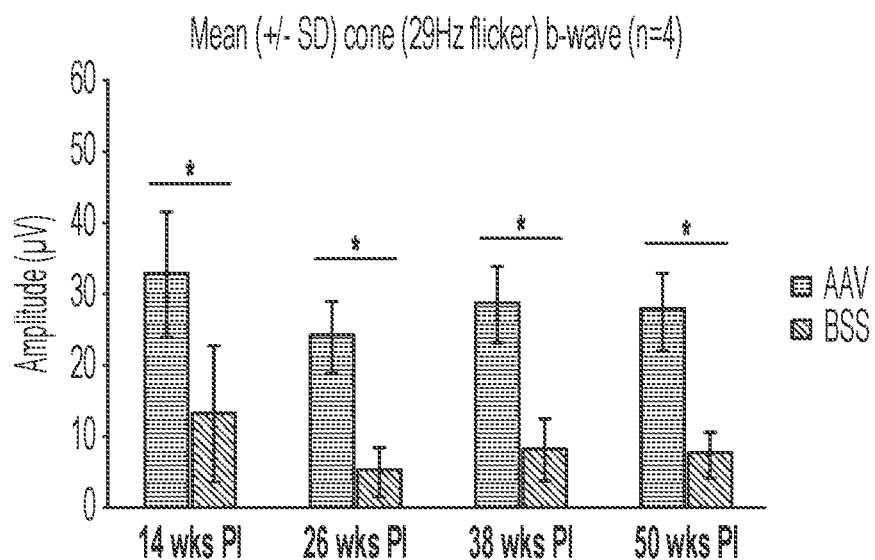
FIG. 19C

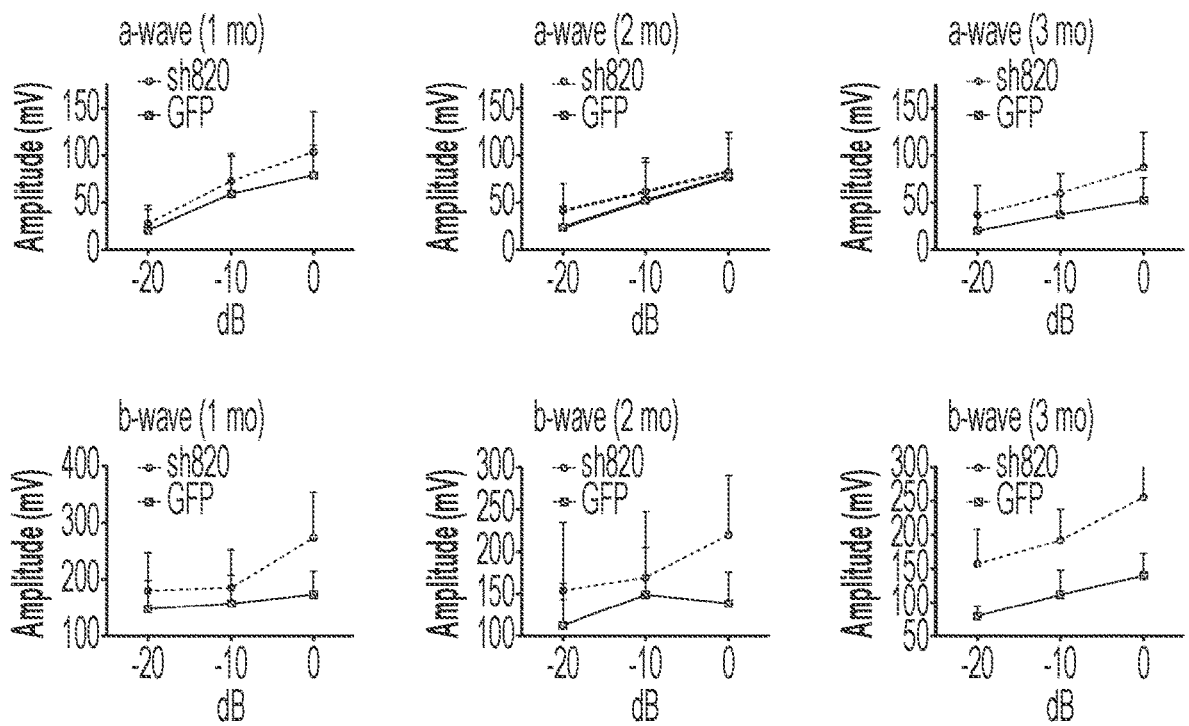

FIG. 23

| Length | #reads | % reads | sequence |
|---|---|---|---|

• Sense strand:

| | | | | | seed match |
|---|---|---|---|---|---|
| 2480 | 2502 | 22 | 68731 | 29.40% | CCGTGGCATTCTA<span>CATCTTC</span>AT (SEQ ID NO: 40) |
| 2480 | 2503 | 23 | 28642 | 12.25% | CCCTGGCATTCTA<span>CATCTTC</span>ATA (SEQ ID NO: 41) |
| 2481 | 2503 | 22 | 79959 | 34.21% | CGCGGCATTCTA<span>CATCTTC</span>ATT (SEQ ID NO: 42) |

• Guide strand:

| | | | | | seed seq |
|---|---|---|---|---|---|
| 2510 | 2531 | 21 | 65312 | 10.07% | <span>TGAAGATGTAGAATGCCAC</span>T (SEQ ID NO: 43) |
| 2510 | 2532 | 22 | 337157 | 51.97% | <span>TGAAGATGTAGAATGCCAC</span>TT (SEQ ID NO: 44) |
| 2510 | 2533 | 23 | 82623 | 12.74% | <span>TGAAGATGTAGAATGCCAC</span>TTA (SEQ ID NO: 45) |

FIG. 24

COMPOSITIONS AND METHODS FOR TREATMENT OF DOMINANT RETINITIS PIGMENTOSA

CROSS-REFERENCE TO RELATED APPLICATIONS

This application is a national stage filing under 35 U.S.C. § 371 of PCT Application No. PCT/US2019/035159, filed Jun. 3, 2019, which claims the benefit of the filing dates of U.S. Provisional Application No. 62/679,585, filed Jun. 1, 2018, and U.S. Provisional Application No. 62/809,539, filed Feb. 22, 2019, the entire contents of each of which are incorporated by reference.

GOVERNMENT SUPPORT

This invention was made with government support under R24-EY022012, R01-EY06855, P30-EY001583 and P30-EY021721 awarded by the National Institutes of Health. The government has certain rights in the invention.

REFERENCE TO AN ELECTRONIC SEQUENCE LISTING

The contents of the electronic sequence listing (U119670079US02-SUBSEQ-PRW.txt; Size: 23,193 bytes; and Date of Creation: May 21, 2024) is herein incorporated by reference in its entirety.

BACKGROUND

Autosomal dominant retinitis pigmentosa (adRP) is a blinding disease affecting 1 in 12,000 people. A sizeable fraction of these individuals carry a mutation in the rhodopsin gene (RHO), the light harvesting pigment protein of the photoreceptor cells in the retina. The disease is dominant because inheritance of the mutated gene from either parent leads to retinal degeneration and eventual blindness. Over 100 different mutations identified in RHO lead to blindness. There is currently no approved drug or gene therapy treatment for adRP. Thus, there is a need for effective treatment options pertaining to any and all causes of adRP and related conditions.

SUMMARY

Aspects of the disclosure relate to compositions and methods for treating retinitis pigmentosa (e.g., dominant retinitis pigmentosa) in a subject (e.g., in a human). In some embodiments, one or both alleles of the rhodopsin gene (RHO gene) of a subject (e.g., a human) are silenced by administering a short hairpin RNA (shRNA) molecule to a subject (e.g., to a subject having retinitis pigmentosa, for example to a human having dominant retinitis pigmentosa). In some embodiments, a replacement RHO coding sequence also is administered to the subject to provide a functional RHO protein, e.g., to restore photoreceptor function to the subject. In some embodiments, the replacement RHO coding sequence has one or more nucleotide substitutions relative to the endogenous gene allele(s) that render the replacement gene resistant to the effects of the interfering RNA. In some embodiments, the replacement RHO coding sequence is a human RHO coding sequence (e.g., a wild-type human RHO coding sequence) that includes one or more (e.g., 1, 2, 3, 4, 5, or more) substitutions to render the gene resistant (also referred to as "hardened") to degradation mediated by the shRNA.

In some aspects, the disclosure provides a short hairpin RNA (shRNA) comprising a sense strand comprising the nucleotide sequence GUGGCAUUCUACAUCUUCA (SEQ ID NO: 1), an antisense strand comprising the nucleotide sequence UGAAGAUGUAGAAUGCCAC (SEQ ID NO: 2), and a loop comprising the nucleotide sequence UUCAAGAGA (SEQ ID NO: 3).

In some aspects, the disclosure provides a short hairpin RNA (shRNA) comprising a sense strand comprising the nucleotide sequence GUGGCAUUCUACAUCUUCA (SEQ ID NO: 1), an antisense strand comprising the nucleotide sequence UGAAGAUGUAGAAUGCCAC (SEQ ID NO: 2), and a loop. The loop may consist of nine nucleotides.

In some embodiments, the shRNA comprises the nucleotide sequence: GUGGCAUUCUACAUCUUCAUUCAAGAGAUGAAGAUGUAGAAUGCCAC (SEQ ID NO: 4). In some embodiments, the shRNA consists of the nucleotide sequence GUGGCAUUCUACAUCUUCAUUCAAGAGAUGAAGAUGUAGAAUGCCAC (SEQ ID NO: 4). In some embodiments, the shRNA comprises the nucleotide sequence: GUGGCAUUCUACAUCUUCAUUCAAGAGAUGAAGAUGUAGAAUGCCACUU (SEQ ID NO: 36). In some embodiments, the shRNA consists of the nucleotide sequence GUGGCAUUCUACAUCUUCAUUCAAGAGAUGAAGAUGUAGAAUGCCACUU (SEQ ID NO: 36).

In some aspects, the disclosure provides a short hairpin RNA (shRNA) molecule comprising: a) a sense and antisense strand comprising one of the following sets of sequences: i) a sense strand comprising the nucleotide sequence CUGCCUACAUGUUUCUGCU (SEQ ID NO: 21) and an antisense strand comprising the nucleotide sequence AGCAGAAACAUGUAGGCAG (SEQ ID NO: 22); ii) a sense strand comprising the nucleotide sequence CCUACAUGUUUCUGCUGAU (SEQ ID NO: 23) and an antisense strand comprising the nucleotide sequence AUCAGCAGAAACAUGUAGG (SEQ ID NO: 24); iii) a sense strand comprising the nucleotide sequence GCAUGGUCAUCAUCAUGGU (SEQ ID NO: 25) and an antisense strand comprising the nucleotide sequence ACCAUGAUGAUGACCAUGC (SEQ ID NO: 26); or iv) a sense strand comprising the nucleotide sequence GUGGCAUUCUACAUCUUCA (SEQ ID NO: 1) and an antisense strand comprising the nucleotide sequence UGAAGAUGUAGAAUGCCAC (SEQ ID NO: 2); and b) a loop comprising the nucleotide sequence UUCAAGAGA (SEQ ID NO: 3).

In some aspects, the disclosure provides a short hairpin RNA (shRNA) molecule comprising: a) a sense and antisense strand comprising one of the following sets of sequences: i) a sense strand comprising the nucleotide sequence CUGCCUACAUGUUUCUGCU (SEQ ID NO: 21) and an antisense strand comprising the nucleotide sequence AGCAGAAACAUGUAGGCAG (SEQ ID NO: 22); ii) a sense strand comprising the nucleotide sequence CCUACAUGUUUCUGCUGAU (SEQ ID NO: 23) and an antisense strand comprising the nucleotide sequence AUCAGCAGAAACAUGUAGG (SEQ ID NO: 24); iii) a sense strand comprising the nucleotide sequence GCAUGGUCAUCAUCAUGGU (SEQ ID NO: 25) and an antisense strand comprising the nucleotide sequence ACCAUGAUGAUGACCAUGC (SEQ ID NO: 26); or iv) a sense strand comprising the nucleotide sequence GUGG- CAUUCUACAUCUUCA (SEQ ID NO: 1) and an antisense strand comprising the nucleotide sequence UGAAGAU-GUAGAAUGCCAC (SEQ ID NO: 2); and b) a loop consisting of nine nucleotides.

In some embodiments, the short hairpin RNA (shRNA) molecule comprising or consists of one of the following nucleotide sequences:

CUGCCUACAUGUUUCUGCUUUCAAGAGAAGCAGAAACAUGUAGGCAG; (SEQ ID NO: 27)

CCUACAUGUUUCUGCUGAUUUCAAGAGAAUCAGCAGAAACAUGUAGG; (SEQ ID NO: 28)

GCAUGGUCAUCAUCAUGGUUUCAAGAGAACCAUGAUGAUGACCAUGC; (SEQ ID NO: 29)
or

GUGGCAUUCUACAUCUUCAUUCAAGAGAUGAAGAUGUAGAAUGCCAC. (SEQ ID NO: 4)

In some embodiments, the short hairpin acid (shRNA) molecule comprising or consists of one of the following nucleotide sequences:

CUGCCUACAUGUUUCUGCUUUCAAGAGAAGCAGAAACAUGUAGGCAGUU; (SEQ ID NO: 37)

CCUACAUGUUUCUGCUGAUUUCAAGAGAAUCAGCAGAAACAUGUAGGUU; (SEQ ID NO: 38)

GCAUGGUCAUCAUCAUGGUUUCAAGAGAACCAUGAUGAUGACCAUGCUU; (SEQ ID NO: 39)
or

GUGGCAUUCUACAUCUUCAUUCAAGAGAUGAAGAUGUAGAAUGCCACUU. (SEQ ID NO: 36)

In other aspects, the disclosure provides a vector encoding an shRNA of any one of the above-mentioned embodiments or as otherwise described herein. In some embodiments, the shRNA coding sequence is operably linked to a promoter, e.g., a human H1 RNA promoter.

In some embodiments, the vector further comprises a recombinant RHO coding sequence that does not contain a sequence targeted by the shRNA. In some embodiments, the recombinant RHO coding sequence is codon-optimized for expression in a human cell. In some embodiments, the recombinant RHO coding sequence comprises a nucleotide sequence that is at least 90% (e.g., at least 90%, at least 91%, at least 92%, at least 93%, at least 94%, at least 95%, at least 96%, at least 97%, at least 98% or at least 99%) identical to the nucleotide sequence of SEQ ID NO: 5. In some embodiments, the recombinant RHO coding sequence comprises a nucleotide sequence that is one, two, three, four, five or between five and ten nucleotides different from the nucleotide sequence of SEQ ID NO: 5. In some embodiments, the recombinant RHO coding sequence comprises the nucleotide sequence of SEQ ID NO: 5. In some embodiments, the recombinant RHO coding sequence is operably linked to a promoter, e.g., a human opsin proximal promoter. In some embodiments, the vector is a plasmid. In some embodiments, the vector is a viral vector. In some embodiments, the viral vector is a recombinant adeno-associated viral (rAAV) vector. In some embodiments, the rAAV vector is self-complementary.

In other aspects, the disclosure provides a vector comprising a nucleotide sequence that is at least 90% (e.g., at least 90%, at least 91%, at least 92%, at least 93%, at least 94%, at least 95%, at least 96%, at least 97%, at least 98% or at least 99%) identical to the nucleotide sequence of SEQ ID NO: 6. In some embodiments, the recombinant RHO coding sequence comprises a nucleotide sequence that is one, two, three, four, five or between five and ten nucleotides different from the nucleotide sequence of SEQ ID NO: 6. In some embodiments, the vector comprises the nucleotide sequence of SEQ ID NO: 6. In some embodiments, the vector is a plasmid. In some embodiments, the vector is a viral vector. In some embodiments, the viral vector is a recombinant adeno-associated viral (rAAV) vector. In some embodiments, the rAAV vector is self-complementary.

In yet other aspects, the disclosure provides a recombinant adeno-associated viral (rAAV) particle comprising any one of the rAAV vectors described above or as otherwise described herein. In some embodiments, the rAAV particle is an rAAV serotype 5 (rAAV5) particle.

In other aspects, the disclosure provides a composition comprising any one of the shRNAs, vectors, or rAAV particles described above or as otherwise described herein and a pharmaceutically acceptable carrier. In some embodiments, the disclosure provides a method of modulating RHO expression in a subject (e.g., a human subject), the method comprising administering to the subject the composition. In some embodiments, the disclosure provides a method of treating retinitis pigmentosa in a subject (e.g., a human subject), the method comprising administering to the subject the composition. In some embodiments, the subject is a mammal. In some embodiments, the mammal is a rodent or a dog. In some embodiments, the mammal is a human (e.g., a human having or known to have, for example diagnosed as having, retinitis pigmentosa, for example dominant retinitis pigmentosa). In some embodiments, the composition is for use in treating retinitis pigmentosa. In some embodiments, the composition is for use in the manufacture of a medicament to treat retinitis pigmentosa.

These and other aspects are described in the following drawings, examples, and claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1H show shRNA-mediated knockdown of wild type (WT), P23H, T17M, and shRNA820-resistant ($RHO_{820}$) variants of human rhodopsin (RHO). HEK293T cells were transfected with a plasmid expressing either WT, P23H, T17M or shRNA820-resistant ($RHO_{820}$) human RHO with a C-terminal turboGFP tag (RHO-tGFP) as well as with a rAAV2 plasmid (denoted with lane labels) encoding either empty DNA (no shRNA), a control shRNA, $shRNA_{131}$, $shRNA_{134}$, or $shRNA_{820}$. A no DNA transfection control was also included. (FIGS. 1A, 1C, 1E, 1G) Immunoblots of protein samples isolated from transfected HEK293T cells probed for turboGFP tag and β-tubulin as the loading control. (FIGS. 1B, 1D, 1F, 1H) Relative quantification of the monomeric form of RHO-GFP (top row) and of the monomeric and aggregated forms of RHO-GFP (lower row). The first lane of each western blot contained the Chameleon Duo Pre-stained Protein Ladder from Li-Cor. Bars denote mean value of three technical replicates, error bars denote SEM. ns.=not significant, *p<0.05, p<0.01, *p<0.001, ****p<0.0001.

FIGS. 2A-2H show suppression of rhodopsin with shRNA$_{820}$ in wildtype (WT) retinas. (FIGS. 2A-2C) In vivo imaging results from representative WT eyes 7-8 weeks post-injection with scAAV2/5-H1-shRNA$_{820}$ at $1\times10^{11}$ (FIG. 2B) and $5\times10^{11}$ vg/mL (FIG. 2C) titers as compared to uninjected control (FIG. 2A). Shown are OCT scans (left), normalized inner/outer segment (IS/OS) intensity topography (middle) and outer nuclear layer (ONL) thickness topography (right). Dotted lines, injection bleb boundaries. Arrows, location of the OCTs shown on left. (FIGS. 2D, 2E) Normalized IS/OS intensity (FIG. 2D) and ONL thickness (FIG. 2E) sampled within the injected blebs (horizontal line shaded circles, upper panels) and uninjected control locations (diagonal line shaded circles, lower panels) in ten eyes injected with a range of titers. Symbols represent group averages (±SD) from 33 to 95 samples (see FIG. 12). Dashed lines denote the 99$^{th}$ percentile limits of the respective parameters sampled at the same retinal locations in uninjected control eyes. Dropdown arrows estimate the titers corresponding to the transitions to a detectable effect. (FIG. 2F) Microphotographs of hematoxylin/eosin stained (top row) and rhodopsin (RHO) immunolabeled retinal cryosections showing morphology of the ONL and outer segments (OS) in treated (Tx; with 1-10×10$^{11}$ vg/mL titer range) and untreated (UnTx) areas 7-8 weeks post-injection. (FIG. 2G) Schematic representation of the retinas of WT dogs treated with 1-50×10$^{11}$ vg/mL titers showing the location of neuroretinal punches used for quantification of rhodopsin (RNA and protein) expression 7-8 weeks post-injection. Dashed lines, bleb boundaries; stippled area: tapetal region. (FIG. 2H) Quantification of the levels of endogenous canine RHO RNA remaining in the treated retinal area as a percentage of levels measured in the untreated area of eyes injected with the different vector titers. Representative immunoblot and quantification of the levels of endogenous canine RHO protein remaining in the treated retinal area as a percentage of levels measured in the untreated area of eyes injected with the different vector titers. Labels such as N282-OD refer to animal and eye; OSasOD designation refers to left eye being displayed as right eye for comparability.

(FIG. 3A) Schematic representation of the fundus of four RHO-mutant dog eyes injected with scAAV2/5-H1-shRNA$_{820}$ at 1-10×10$^{11}$ vg/mL titers showing the location of neuroretinal punches used for quantification of rhodopsin (RNA and protein) expression at 8-10 weeks post-injection. Dashed lines, bleb boundaries; stippled area: tapetal region. (FIG. 3B) Quantification of the levels of endogenous canine RHO RNA remaining in the treated retinal area as a percentage of levels measured in the untreated area of eyes injected with different titers. Representative immunoblot and quantification of the levels of endogenous canine RHO protein remaining in the treated retinal area as a percentage of levels measured in the untreated area of eyes injected with 1-50×10$^{11}$ vg/mL titers. (FIG. 3C) Outer nuclear layer (ONL) thickness topography two weeks post light exposure (8-10 weeks post-injection) in four RHO-mutant dog eyes treated with 1-10×10$^{11}$ vg/mL titers. Dotted lines, bleb boundaries; dashed lines, ONL rescue boundaries. Insets, maps of significance showing retinal regions with ONL thickness (left) and IS/OS intensity (right) values compared point by point to the 99$^{th}$ percentile confidence intervals of uninjected controls. (FIG. 3D) Microphotographs of H&E stained (top row) and rhodopsin (RHO,)/human cone arrestin (hCA) co-immunolabeled retinal cryosections showing morphology of the ONL and outer segments (OS) two weeks post light exposure (8-10 weeks post-injection) in treated (Tx; with 1-10×10$^{11}$ vg/mL titer range) and untreated (UnTx) areas of the same eyes shown in (FIG. 3C).

(FIGS. 4A-4B) Outer nuclear layer (ONL) thickness topography after injection/before light exposure (post Inj.) and two weeks post light exposure (post LE) in two RHO-mutant eyes injected with scAAV2/5-hOP-RHO$_{820}$-H1-shRNA$_{820}$ at 5×10$^{11}$ vg/mL titer. Dotted lines, bleb boundaries; dashed lines, ONL rescue boundaries. Insets, maps of significance described in FIGS. 3A-3E. (FIGS. 4C-4D) Rhodopsin (RHO)/human cone arrestin (hCA) co-immunolabeled retinal cryosections showing morphology of the ONL and outer segments (OS) in treated and untreated (UnTx) areas of the same eyes shown in (FIGS. 4A-4B). (FIG. 4E) Schematic representation of the fundus of four RHO-mutant dog eyes injected with a 5×10$^{11}$ vg/mL titer showing the location of neuroretinal punches used for quantification of rhodopsin (RNA and protein) expression. Dashed lines, bleb boundaries; stippled area: tapetal region. (FIG. 4F) Quantification of the levels of endogenous canine RHO RNA remaining in the treated retinal area as a percentage of levels measured in the untreated area of injected eyes. (FIG. 4G) Quantification of the levels of exogenous human RHO RNA (RHO$_{820}$) present in the treated retinal area as a percentage of physiological levels of endogenous canine RHO measured in the untreated area of injected eyes. Representative immunoblot and quantification of the levels of total (endogenous canine and RHO$_{820}$) RHO protein remaining in the treated retinal area as a percentage of levels measured in the untreated area of injected eyes.

(FIG. 5A) Upper, Timeline showing timepoints of injection of scAAV2/5-RHO$_{820}$-shRNA$_{820}$ (5×10$^{11}$ vg/mL titer) in one eye of two RHO-mutant dogs (contralateral eye injected with BSS), light exposures (LE1-LE4), OCT imaging and ERG sessions. Lower, Representative outer nuclear layer (ONL) thickness maps prior to injection, 11 weeks post-injection (immediately before LE1), 1.5 weeks post LE1, and 2.1 weeks post LE4 of an eye injected with scAAV2/5-RHO$_{820}$-shRNA$_{820}$. Dashed lines, ONL rescue boundaries. The optic nerve head (black circle) and major blood vessels (solid black line), tapetum boundary (solid grey line), and fovea-like region (ellipse) are overlaid (middle row). Insets, maps of significance described in FIGS. 3A-3E. (FIG. 5B) Schematics (left) showing retinal locations sampled for quantification of ONL thickness and IS/OS intensity within the treated area of two RHO mutant eyes injected with scAAV2/5-RHO$_{820}$-shRNA$_{820}$. Longitudinal quantification of the mean (+SD) difference in ONL thickness (middle) and IS/OS intensity (right) in the injected eyes when compared to uninjected controls. Horizontal dashed lines represent limits of WT variability (+/−3SD). (FIG. 5C) Representative ERG traces of rod (−1.7 log cd·s·m$^{-2}$), mixed rod-cone (0.51 log cd·s·m$^{-2}$) recorded dark adapted, and cone responses to single stimuli (0.51 log cd·s·m$^{-2}$) or 29-Hz cone flicker (0.26 log cd·s·m$^{-2}$) recorded light adapted at ~2 weeks after each of four light exposure sessions in a RHO-mutant dog injected in one eye with scAAV2/5-RHO$_{820}$-shRNA$_{820}$ (solid line) and with BSS (dashed line) in the contralateral eye. (FIG. 5D) Longitudinal quantification of maximal amplitudes of mixed rod-cone a- and b-waves (upper panel), and of cone 1 Hz and 29 Hz flicker responses (lower panel) in two RHO-mutant dogs injected in one eye with scAAV2/5-RHO$_{820}$-shRNA$_{820}$ (horizontal line shading) and in the contralateral eye with BSS (diagonal line shading) at similar time-points as shown in (FIG. 5C).

(FIG. 9A) Schematic representation of the retinas of RHO WT dogs injected subretinally with AAV2/5-Rz525 at 20 or 50×10$^{11}$ vg/mL titers showing the location of neuroretinal punches used for quantification of canine rhodopsin (RNA and protein) expression. Dashed lines, bleb boundaries; stippled area: tapetal region. (FIG. 9B) Quantification of the levels of endogenous canine RHO RNA remaining in the treated (Tx) retinal area (injected with 50×10$^{11}$ vg/mL titer) as a percentage of levels measured in the untreated (UnTx) area. (FIG. 9C) Representative immunoblot (upper) and quantification of the levels of endogenous canine RHO protein remaining (lower) in the treated retinal area as a percentage of levels measured in the untreated area of eyes injected with 20 or 50×10$^{11}$ vg/mL titers. OSasOD designation refers to left eye being displayed as right eye for comparability.

FIGS. 10A-10E show the suppression of RHO expression with Rz525 in RHO mutant canine retinas. (FIG. 10A) Schematic representation of the retinas of RHO mutant dogs injected with BSS or AAV2/5-Rz525 at 20 or 100×10$^{11}$ vg/mL titers showing the location of neuroretinal punches used for quantification of canine rhodopsin (RNA and protein) expression. Dashed lines, bleb boundaries; stippled area: tapetal region. (FIG. 10B) Quantification of the levels of endogenous canine RHO RNA remaining in the treated retinal area as a percentage of levels measured in the untreated area of eyes injected with BSS or AAV2/5-Rz525 at 20 or 100×10$^{11}$ vg/mL titers. (FIG. 10C) Representative immunoblot (upper) and quantification of the levels of endogenous canine RHO protein remaining (lower) in the treated retinal area as a percentage of levels measured in the untreated area of eyes injected with BSS or AAV2/5-Rz525 at 20 or 100×10$^{11}$ vg/mL titers. (FIG. 10D) ONL thickness topography two weeks post light exposure (post LE) in two RHO mutant dog eyes injected 8 weeks earlier with AAV2/5-Rz525 at 20 or 100×10$^{11}$ vg/mL titers. Dotted lines, bleb boundaries; dashed lines, ONL rescue boundaries. (FIG. 10E) Multifocal dark lesions (white arrows) visible by NIR cSLO imaging (upper and lower left panels) in both retinas of a RHO mutant dog treated 8 weeks earlier with AAV2/5-Rz525 at 100×10$^{11}$ vg/mL correspond on the OCT B scan (upper right panel) to focal nodules of increased reflectivity (white arrows) located in the subretinal space and RPE/choroid, and by histology (lower right panel) to focal inflammatory cell infiltrates. Retinal separation is visible on the OCT B scan (white arrowheads). Dashed lines, bleb boundaries; dotted line represents location of OCT B scan. OSasOD designation refers to left eye being displayed as right eye for comparability.

FIGS. 11A-11C show inefficient suppression of RHO expression with shRNA$_{131}$ in WT canine retinas. (FIG. 11A) Schematic representation of the fundus of eyes of RHO WT dogs injected with scAAV2/5-shRNA$_{131}$ at 10 or 50×10$^{11}$ vg/mL titers showing the location of neuroretinal punches used for quantification of canine rhodopsin (RNA and protein) expression at 8 weeks post-injection. Dashed lines, bleb boundaries; stippled area: tapetal region. (FIG. 11B) Quantification of the levels of endogenous canine RHO RNA remaining in the treated retinal area as a percentage of levels measured in the untreated area of eyes injected with 10 or 50×10$^{11}$ vg/mL titers. (FIG. 11C) Representative immunoblot and quantification of the levels of endogenous canine RHO protein remaining in the treated retinal area as a percentage of levels measured in the untreated area of eyes injected with 10 or 50×10$^{11}$ vg/mL titers. OSasOD designation refers to left eye being displayed as right eye for comparability.

FIGS. 13A-13G show suppression and replacement of rhodopsin with two separate vectors: incomplete protection of rods and retinal toxicity in RHO mutant eyes. (FIGS. 13A-13C) OCT imaging and histological analysis of retinal protection against light exposure (LE) in a RHO mutant eye co-injected with 5×10$^{11}$ vg/mL of scAAV2/5-shRNA$_{820}$ and 5×10$^{11}$ vg/mL of scAAV2/5-RHO$_{820}$ (Treatment 1:1). (FIG. 13A) ONL thickness topography 7 weeks after injection/before light exposure (post Inj.) and four weeks post light exposure (post LE) Dotted lines, bleb boundaries; white arrow, location of OCT B scan shown in lower panel. (FIG. 13B) Rhodopsin (Rho)/human cone arrestin (hCA) co-immunolabeled retinal cryosection showing morphology of the outer nuclear layer (ONL) and outer segments (OS) in treated and untreated (UnTx) areas of the same eye shown in (FIG. 13A). (FIG. 13C) H&E stained retinal microphotograph taken within the treated area showing maximal rescue effect. (FIG. 13D-13F) Similar analysis as in (FIGS. 13A-13C) in a RHO mutant eye co-injected with 5×10$^{11}$ vg/mL of scAAV2/5-shRNA$_{820}$ and 10×10$^{11}$ vg/mL of scAAV2/5-RHO$_{820}$ (Treatment 1:2). (FIG. 13D) ONL thickness topography. Dotted lines, bleb boundaries; dashed lines, ONL rescue boundaries; white arrow corresponds to location of OCT B scan shown in lower panel; white arrows on OCT B scan show increased perivascular thickening and reflectivity. (FIG. 13E) Double fluorescence IHC (Rhodopsin; human cone arrestin). (FIG. 13F) H&E stained retinal microphotograph taken within the treated area showing limited ONL rescue and severe lesions of perivascular cell infiltration (arrows). (FIG. 13G) OCT imaging 11 weeks post injection in a RHO mutant eye co-injected with 5×10$^{11}$ vg/mL of scAAV2/5-shRNA$_{820}$ and 10×10$^{11}$ vg/mL of scAAV2/5-RHO$_{820}$ (Treatment 1:2) but that was not exposed to light. Dotted lines, bleb boundaries; grey and white arrows show locations of single OCT B scans (right panel). OSasOD designation refers to left eye being displayed as right eye for comparability.

(FIG. 14A-14B) ONL thickness topography after injection/before light exposure (post Inj.) and two weeks post light exposure (post LE) in two RHO mutant dog eyes injected with scAAV2/5-RHO$_{820}$-shRNA$_{820}$ at 5×10$^{11}$ vg/mL titer. Dotted lines, bleb boundaries; dashed lines, ONL rescue boundaries. Insets, maps of significance showing retinal regions with ONL thickness (upper) and IS/OS intensity (lower) values compared point by point to the 99$^{th}$ percentile confidence intervals of uninjected controls. (FIGS. 14C-14D) Rhodopsin (Rho)/human cone arrestin (hCA) co-immunolabeled retinal cryosections showing morphology of the outer nuclear layer (ONL) and outer segments (OS) in treated and untreated (UnTx) areas of the same eyes shown in (FIGS. 14A-14B). OSasOD designation refers to left eye being displayed as right eye for comparability.

(FIGS. 15A, 15B) Pseudocolor ONL topographies of representative dogs housed under cyclic dim-red light (FIG. 15A) or cyclic standard white kennel illumination (FIG. 15B). All eyes are shown as equivalent right eyes. The optic nerve head (black circle) and major blood vessels (white lines), tapetum boundary (grey line), and fovea-like region (ellipse) are overlaid (FIG. 15C) Schematic, loci selected in five retinal regions for quantitation of ONL thickness. C, central; ST, superotemporal; SN, superonasal; IT, inferotemporal; and IN, inferonasal. Plots of ONL thickness as a function of age at all sampled individual loci shown as a difference from the mean normal value at the same location. Dashed lines delimit 99$^{th}$ percentile of normal variability.

(FIG. 16A) Single-stranded AAV carrying a mouse opsin proximal promoter (mOP) driving the expression of a hammerhead ribozyme (Rz525) designed to cleave murine, canine and human RHO mRNA. (FIG. 16B) Self-complementary AAV carrying an H1 RNA polymerase III promoter (H1) driving the expression of a short hairpin RNA (shRNA$_{131}$) designed to cleave canine and human RHO mRNA. (FIG. 16C) Self complementary AAV carrying an H1 RNA polymerase III promoter (H1) driving the expression of a short hairpin RNA (shRNA$_{820}$) designed to cleave canine and human RHO mRNA. (FIG. 16D) Self-complementary AAV carrying a human opsin promoter driving the expression of a replacement human RHO mRNA (RHO$_{820}$) designed to be resistant to suppression by shRNA$_{820}$. (FIG. 16E) Self-complementary AAV carrying both the knockdown reagent shRNA$_{820}$ and the human resistant replacement RHO$_{820}$. TR: AAV2 inverted terminal repeat; mTR: mutant TR; wtTR: wild type TR; SV40 SD/SA: splice donor/acceptor element derived from simian virus 40; hp Rz: hairpin ribozyme; SV40 pA: SV40 derived polyadenylation terminal signal; HSV TK pro: human herpes simplex virus derived thymidine kinase promoter; Neo R: neomycin resistance gene. bGH pA: bovine growth hormone polyadenylation terminal signal; hGFP: humanized GFP.

FIGS. 19A-19C show longitudinal quantification of maximal amplitudes of rod b-waves (FIG. 19A), mixed rod-cone a- and b-waves (FIG. 19B), and of cone 1 Hz and 29 Hz flicker responses (FIG. 19C) in four RHO-mutant dogs injected in one eye with scAAV2/5-RHO820-shRNA820 (horizontal line shading) and in the contralateral eye with BSS (diagonal line shading) at similar time-points as shown in FIGS. 18A-18D. AAV: scAAV2/5-RHO820-shRNA820.

FIG. 23 shows longitudinal quantification of maximal amplitudes of rod and mixed rod-cone a- and b-waves in P23H RHO mice injected in one eye with scAAV2/5-RHO820-shRNA820 (circles and dashed line) or AAV2/5-GFP (squares and solid line). These two groups of mice were subjected to brief light flashes of varying intensities (−20 decibels (dB), −10 dB and 0 dB). Electrical responses of these mice were analyzed at 1 month, 2 months, and 3 months post-injection.

FIG. 24 shows the sequences of most frequent short mRNAs expressed in HEK293 cells following transfection with scAAV2/5-RHO820-shRNA820, after size fractionation.

DETAILED DESCRIPTION

Figure 1E:
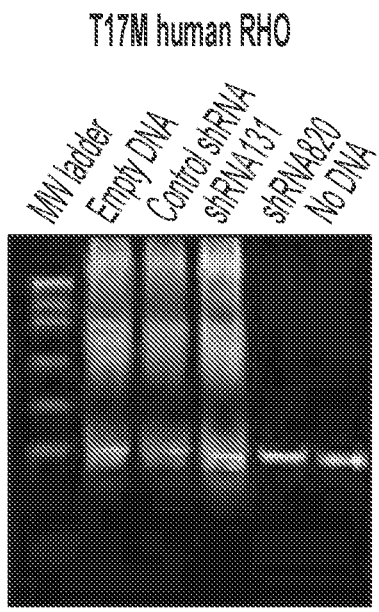

Aspects of the application provide methods and compositions that are useful for treating retinitis pigmentosa in a subject (e.g., in a subject having dominant retinitis pigmentosa such as a human subject having dominant retinitis pigmentosa).

In some embodiments, a short hairpin RNA (shRNA) is provided that targets human, dog and/or mouse rhodopsin (RHO) mRNA. In some embodiments, the shRNA comprises a sense strand comprising the nucleotide sequence GUGGCAUUCUACAUCUUCA (SEQ ID NO: 1), an antisense strand comprising the nucleotide sequence UGAAGAUGUAGAAUGCCAC (SEQ ID NO: 2), and a loop sequence. In some embodiments, the shRNA comprises a sense strand that comprises a nucleotide sequence that is one, two, or three nucleotides different from the sequence of SEQ ID NO: 1, and an antisense strand that comprises a nucleotide sequence that is one, two, or three nucleotides different from the sequence of SEQ ID NO: 2. In some embodiments, the loop comprises a sequence having a length of 5 to 10 nucleotides. In certain embodiments, the loop comprises a sequence having a length of 9 nucleotides. In some embodiments, the loop comprises UUCAAGAGA (SEQ ID NO: 3). In certain embodiments, the loop is SEQ ID NO: 3. In certain embodiments, the loop comprises a nucleotide sequence that is one or two nucleotides different from the sequence of SEQ ID NO: 3.

In some embodiments, the shRNA comprises a sense strand comprising the nucleotide sequence GUGGCAUUCUACAUCUUCA (SEQ ID NO: 1), an antisense strand comprising the nucleotide sequence UGAAGAUGUAGAAUGCCAC (SEQ ID NO: 2), and a loop comprising the nucleotide sequence UUCAAGAGA (SEQ ID NO: 3). In some embodiments, the shRNA comprises a sense strand comprising the nucleotide sequence GUGGCAUUCUACAUCUUCA (SEQ ID NO: 1), an antisense strand comprising the nucleotide sequence UGAAGAUGUAGAAUGCCACUU (SEQ ID NO: 10), and a loop comprising the nucleotide sequence UUCAAGAGA (SEQ ID NO: 3). In some embodiments, the shRNA comprises a sense strand that comprises a nucleotide sequence that is one, two, or three nucleotides different from the sequence of SEQ ID NO: 1; an antisense strand that comprises a nucleotide sequence that is one, two, or three nucleotides different from the sequence of SEQ ID NO: 10; and a loop that comprises a nucleotide sequence that is one or two nucleotides different from the sequence of SEQ ID NO: 3.

In some embodiments, the shRNA comprises or consists of the sequence of SEQ ID NO: 4 shown below. shRNA820 Sequence:

(SEQ ID NO: 4)
GUGGCAUUCUACAUCUUCAUUCAAGAGAUGAAGAUGUAGAAUGCCAC

In some embodiments, the shRNA comprises a nucleotide sequence that is one, two, or three nucleotides different from the sequence of SEQ ID NO: 4.

In certain embodiments, the shRNA comprises a sense and antisense strand comprising one of the following sets of sequences: i) a sense strand comprising the nucleotide sequence CUGCCUACAUGUUUCUGCU (SEQ ID NO: 21) and an antisense strand comprising the nucleotide sequence AGCAGAAACAUGUAGGCAG (SEQ ID NO: 22); ii) a sense strand comprising the nucleotide sequence CCUACAUGUUUCUGCUGAU (SEQ ID NO: 23) and an antisense strand comprising the nucleotide sequence AUCAGCAGAAACAUGUAGG (SEQ ID NO: 24); iii) a sense strand comprising the nucleotide sequence GCAUGUCAUCAUCAUGGU (SEQ ID NO: 25) and an antisense strand comprising the nucleotide sequence ACCAUGAUGAUGACCAUGC (SEQ ID NO: 26).

In other embodiments, the shRNA comprises: i) a sense strand comprising a nucleotide sequence that is one, two, or three nucleotides different from SEQ ID NO: 21, and an antisense strand comprising a nucleotide sequence that is one, two, or three nucleotides different from SEQ ID NO: 22; ii) a sense strand comprising a nucleotide sequence that is one, two, or three nucleotides different from SEQ ID NO: 23, and an antisense strand comprising a nucleotide sequence that is one, two, or three nucleotides different from SEQ ID NO: 24; or iii) a sense strand comprising a nucleotide sequence that is one, two, or three nucleotides different from SEQ ID NO: 25, and an antisense strand comprising a nucleotide sequence that is one, two, or three nucleotides different from SEQ ID NO: 26.

In some embodiments, the shRNA can be delivered using a vector as an shRNA driven by a promoter (e.g., a human H1 RNA promoter). In some embodiments, the vector is a plasmid. In some embodiments, the vector is a viral vector, such as an adeno-associated virus (AAV) vector. In some embodiments, the vector sequence encoding the shRNA comprises the sequence GTGGCATTCTACATCTTCATTCAAGAGATGAAGATGTAGAATGCCAC (SEQ ID NO: 9). In some embodiments, the promoter driving shRNA expression comprises a sequence that is at least 90%, at least 91%, at least 92%, at least 93%, at least 94%, at least 95%, at least 96%, at least 97%, at least 98%, at least 99%, or 100% identical to the sequence: TAAAACGACGGCCAGTGAATTCATATTTGCATGTCGCTATGTGTTCTGGGAAATCAC CATAAACGTGAAATGTCTTTGGATTTGGGAATCTTATAAGTTCTGTATGAGACCACT CGGATCC (SEQ ID NO: 8). In some embodiments, the same vector comprises a coding sequence that encodes normal (e.g., wild-type) rhodopsin protein but is resistant to the action of the shRNA expressed by the vector.

In some embodiments, a normal (e.g., wild-type) rhodopsin (RHO) coding sequence that is hardened to an shRNA as described herein can have a sequence based on the human RHO gene (e.g., having a sequence shown in Accession No. NG_009115.1). In some embodiments, the normal RHO coding sequence is modified to include one or more (e.g., 2, 3, 4, 5, 6, 7, 8, 9, 10 or more) mutations that render the mRNA expressed by the coding sequence resistant to the shRNA as described herein. In some embodiments, the RHO coding sequence comprises the sequence GTGGCTTTTTATATATTCA (SEQ ID NO: 11) which may be resistant to an shRNA as described herein. In some embodiments, the RHO coding sequence comprises a sequence that is at least 90%, at least 91%, at least 92%, at least 93%, at least 94%, at least 95%, at least 96%, at least 97%, at least 98%, at least 99%, or 100% identical to SEQ ID NO: 5 below.

RHO820 Sequence:

(SEQ ID NO: 5)
ATGAATGGCACAGAAGGCCCTAACTTCTACGTGCCCTTCTCCAATGCGACGGGTGTG

GTACGCAGCCCCTTCGAGTACCCACAGTACTACCTGGCTGAGCCATGGCAGTTCTCC

ATGCTGGCCGCCTACATGTTTCTGCTGATCGTGCTGGGCTTCCCCATCAACTTCCTCA

CGCTCTACGTCACCGTCCAGCACAAGAAGCTGCGCACGCCTCTCAACTACATCCTGC

TCAACCTAGCCGTGGCTGACCTCTTCATGGTCCTAGGTGGCTTCACCAGCACCCTCT

ACACCTCTCTGCATGGATACTTCGTCTTCGGGCCCACAGGATGCAATTTGGAGGGCT

TCTTTGCCACCCTGGGCGGTGAAATTGCCCTGTGGTCCTTGGTGGTCCTGGCCATCG

AGCGGTACGTGGTGGTGTGTAAGCCCATGAGCAACTTCCGCTTCGGGGAGAACCAT

GCCATCATGGGCGTTGCCTTCACCTGGGTCATGGCGCTGGCCTGCGCCGCACCCCCA

CTCGCCGGCTGGTCCAGGTACATCCCCGAGGGCCTGCAGTGCTCGTGTGGAATCGAC

TACTACACGCTCAAGCCGGAGGTCAACAACGAGTCTTTTGTCATCTACATGTTCGTG

GTCCACTTCACCATCCCCATGATTATCATCTTTTTCTGCTATGGGCAGCTCGTCTTCA

CCGTCAAGGAGGCCGCTGCCCAGCAGCAGGAGTCAGCCACCACACAGAAGGCAGA

GAAGGAGGTCACCCGCATGGTCATCATCATGGTCATCGCTTTCCTGATCTGCTGGGT

GCCCTACGCCAGCGTGGCTTTTTATATATTCACCCACCAGGGCTCCAACTTCGGTCC

CATCTTCATGACCATCCCAGCGTTCTTTGCCAAGAGCGCCGCCATCTACAACCCTGT

CATCTATATCATGATGAACAAGCAGTTCCGGAACTGCATGCTCACCACCATCTGCTG

CGGCAAGAACCCACTGGGTGACGATGAGGCCTCTGCTACCGTGTCCAAGACGGAGA

CGAGCCAGGTGGCCCCGGCCTAA

In some embodiments, the RHO coding sequence is driven by a promoter (e.g., a human opsin proximal promoter). In some embodiments, the promoter comprises a sequence that is at least 80%, at least 85%, at least 90%, at least 91%, at least 92%, at least 93%, at least 94%, at least 95%, at least 96%, at least 97%, at least 98%, at least 99%, or 100% identical to SEQ ID NO: 7 below.

Human Opsin Proximal Promoter Sequence:

(SEQ ID NO: 7)
CCTCATGGAGCTCCTCCTGTCAGAGGAGTGTGGGGACTGGATGACTCCAGAGGTAA

CTTGTGGGGAACGAACAGGTAAGGGGCTGTGTGACGAGATGAGAGACTGGGAGA

ATAAACCAGAAAGTCTCTAGCTGTCCAGAGGACATAGCACAGAGGCCCATGGTCCC

TATTTCAAACCCAGGCCACCAGACTGAGCTGGGACCTTGGGACAGACAAGTCATGC

AGAAGTTAGGGGACCTTCTCCTCCCTTTTCCTGGATCCTGAGTACCTCTCCTCCCTGA

CCTCAGGCTTCCTCCTAGTGTCACCTTGGCCCCTCTTAGAAGCCAATTAGGCCCTCA

GTTTCTGCAGCGGGGATTAATATGATTATGAACACCCCCAATCTCCCAGATGCTGAT

TCAGCCAGGAGCTTAGGAGGGGGAGGTCACTTTATAAGGGTCTGGGGGGGTCAGAA

CCCAGAGTCATCCAGCTGGAGCCCTGAGTGGCTGAGCTCAGGCCTTCGCAGCATTCT

TGGGTGGGAGCAGCCACGGGTCAGCCACA

In some embodiments, the vector as described herein comprises a sequence that is at least 80%, at least 85%, at least 90%, at least 91%, at least 92%, at least 93%, at least 94%, at least 95%, at least 96%, at least 97%, at least 98%, at least 99%, or 100% identical to SEQ ID NO: 6 below.

scAAV2/5-hOP-RHO820-H1-shRNA820 Construct Sequence:

```
(SEQ ID NO: 6)
CGCTCGCTCGCTCACTGAGGCCGCCCGGGCAAAGCCCGGGCGTCGGGCGACCTTTG

GTCGCCCGGCCTCAGTGAGCGAGCGAGCGCGCAGAGAGGGAGTGGCCAACTCCATC

ACTAGGGGTTCCTTGTAGTTAATGATTAACCCGCCATGCTACTTATCTACGTAGCCAT

GCTCTAGGATCTGAATTCGGTACCCCTCATGGAGCTCCTCCTGTCAGAGGAGTGTGG

GGACTGGATGACTCCAGAGGTAACTTGTGGGGGAACGAACAGGTAAGGGGCTGTGT

GACGAGATGAGAGACTGGGAGAATAAACCAGAAAGTCTCTAGCTGTCCAGAGGACA

TAGCACAGAGGCCCATGGTCCCTATTTCAAACCCAGGCCACCAGACTGAGCTGGGA

CCTTGGGACAGACAAGTCATGCAGAAGTTAGGGGACCTTCTCCTCCCTTTTCCTGGA

TCCTGAGTACCTCTCCTCCCTGACCTCAGGCTTCCTCCTAGTGTCACCTTGGCCCCTC

TTAGAAGCCAATTAGGCCCTCAGTTTCTGCAGCGGGGATTAATATGATTATGAACAC

CCCCAATCTCCCAGATGCTGATTCAGCCAGGAGCTTAGGAGGGGGAGGTCACTTTAT

AAGGGTCTGGGGGGGTCAGAACCCAGAGTCATCCAGCTGGAGCCCTGAGTGGCTGA

GCTCAGGCCTTCGCAGCATTCTTGGGTGGGAGCAGCCACGGGTCAGCCACATCTAG

AGGATCCGGTACTCGAGGAACTGAAAAACCAGAAAGTTAACTGGTAAGTTTAGTCT

TTTTGTCTTTTATTTCAGGTCCCGGATCCGGTGGTGGTGCAAATCAAAGAACTGCTCC

TCAGTGGATGTTGCCTTTACTTCTAGGCCTGTACGGAAGTGTTACTTCTGCTCTAAAA

GCTGCGGAATTGTACCCGCGGCCGCCCAGCTGGAGCCCTGAGTGGCTGAGCTCAGG

CCTTCGCAGCATTCTTGGGTGGGAGCAGCCACGGGTCAGCCACAAGGGCCACAGCC

ATGAATGGCACAGAAGGCCCTAACTTCTACGTGCCCTTCTCCAATGCGACGGGTGTG

GTACGCAGCCCCTTCGAGTACCCACAGTACTACCTGGCTGAGCCATGGCAGTTCTCC

ATGCTGGCCGCCTACATGTTTCTGCTGATCGTGCTGGGCTTCCCCATCAACTTCCTCA

CGCTCTACGTCACCGTCCAGCACAAGAAGCTGCGCACGCCTCTCAACTACATCCTGC

TCAACCTAGCCGTGGCTGACCTCTTCATGGTCCTAGGTGGCTTCACCAGCACCCTCT

ACACCTCTCTGCATGGATACTTCGTCTTCGGGCCCACAGGATGCAATTTGGAGGGCT

TCTTTGCCACCCTGGGCGGTGAAATTGCCCTGTGGTCCTTGGTGGTCCTGGCCATCG

AGCGGTACGTGGTGGTGTGTAAGCCCATGAGCAACTTCCGCTTCGGGGAGAACCAT

GCCATCATGGGCGTTGCCTTCACCTGGGTCATGGCGCTGGCCTGCGCCGCACCCCCA

CTCGCCGGCTGGTCCAGGTACATCCCCGAGGGCCTGCAGTGCTCGTGTGGAATCGAC

TACTACACGCTCAAGCCGGAGGTCAACAACGAGTCTTTTGTCATCTACATGTTCGTG

GTCCACTTCACCATCCCCATGATTATCATCTTTTTCTGCTATGGGCAGCTCGTCTTCA

CCGTCAAGGAGGCCGCTGCCCAGCAGCAGGAGTCAGCCACCACACAGAAGGCAGA

GAAGGAGGTCACCCGCATGGTCATCATCATGGTCATCGCTTTCCTGATCTGCTGGGT

GCCCTACGCCAGCGTGGCTTTTTATATATTCACCCACCAGGGCTCCAACTTCGGTCC

CATCTTCATGACCATCCCAGCGTTCTTTGCCAAGAGCGCCGCCATCTACAACCCTGT

CATCTATATCATGATGAACAAGCAGTTCCGGAACTGCATGCTCACCACCATCTGCTG

CGGCAAGAACCCACTGGGTGACGATGAGGCCTCTGCTACCGTGTCCAAGACGGAGA

CGAGCCAGGTGGCCCCGGCCTAAGACCTGCCTAGGACTCTGTGGCCGACTATAGGC
```

-continued

```
GTCTCCCATCCCCTACACCTTCCCCCAGCCACAGCCATCCCACCAGGCGGCCGCGGG
GATCCAGACATGATAAGATACATTGATGAGTTTGGACAAACCACAACTAGAATGCA
GTGAAAAAAATGCTTTATTTGTGAAATTTGTGATGCTATTGCTTTATTTGTAACCATT
ATAAGCTGCAATAAACAAGTTAACAACAACAATTGCATTCATTTTATGTTTCAGGTT
CAGGGGGAGGTGTGGGAGGTTTTTTAGTCGACTAAAACGACGGCCAGTGAATTCAT
ATTTGCATGTCGCTATGTGTTCTGGGAAATCACCATAAACGTGAAATGTCTTTGGAT
TTGGGAATCTTATAAGTTCTGTATGAGACCACTCGGATCCGTGGCATTCTACATCTTC
ATTCAAGAGATGAAGATGTAGAATGCCACTTTTTAAGCTTTTTGGCGTAATCATGGT
CGACATTGGATCGGATCCCGGGCCCGTCGACTAGAGCTCGCTGATCAGCCTCGACTG
TGCCTTCTAGTTGCCAGCCATCTGTTGTTTGCCCCTCCCCCGTGCCTTCCTTGACCCT
GGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGG
AGGATTGGGAAGACAATAGCAGGAACCCCACTCCCTCTCTGCGCGCTCGCTCGCTCA
CTGAGGCCGGGCGACCAAAGGTCGCCCGACGCCCGGGCTTTGCCCGGGCGGCCTCA
GTGAGCGAGCGAGCGCGCAGCTGCTGCATTAATGAATCGGCCAACGCGCGGGGAGA
GGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCT
AACTACGGCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGCTGGTAG
CGGTGGTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
```

-continued

```
TTGGCCGCAGTGTTATCACTCATGGTTATGGCAGCACTGCATAATTCTCTTACTGTCA

TGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAA

AACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTT

CCCCGAAAAGTGCCACCTGACGTCTAAGAAACCATTATTATCATGACATTAACCTAT

AAAAATAGGCGTATCACGAGGCCCTTTCGTCTCGCGCGTTTCGGTGATGACGGTGAA

AACCTCTGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGGGGCTG

GCTTAACTATGCGGCATCAGAGCAGATTGTACTGAGAGTGCACCATATGCGGTGTGA

AATACCGCACAGATGCGTAAGGAGAAAATACCGCATCAGGAAATCCAACATCCAAT

AAATCATACAGGCAAGGCAAAGAATTAGCAAAATTAAGCAATAAAGCCTCAGAGCA

TAAAGCTAAATCGGTTGTACCAAAAACATTATGACCCTGTAATACTTTTGCGGGAGA

AGCCTTTATTTCAACGCAAGGATAAAAATTTTTAGAACCCTCATATATTTTAAATGC

AATGCCTGAGTAATGTGTAGGTAAAGATTCAAACGGGTGAGAAAGGCCGGAGACAG

TCAAATCACCATCAATATGATATTCAACCGTTCTAGCTGATAAATTCATGCCGGAGA

GGGTAGCTATTTTTGAGAGGTCTCTACAAAGGCTATCAGGTCATTGCCTGAGAGTCT

GGAGCAAACAAGAGAATCGATGAACGGTAATCGTAAAACTAGCATGTCAATCATAT

GTACCCCGGTTGATAATCAGAAAAGCCCCAAAAACAGGAAGATTGTATAAGCAAAT

ATTTAAATTGTAAACGTTAATATTTTGTTAAAATTCGCGTTAAATTTTTGTTAAATCA

GCTCATTTTTTAACCAATAGGCCGAAATCGGCAAAATCCCTTATAAATCAAAAGAAT

AGACCGAGATAGGGTTGAGTGTTGTTCCAGTTTGGAACAAGAGTCCACTATTAAAG

AACGTGGACTCCAACGTCAAAGGGCGAAAAACCGTCTATCAGGGCGATGGCCCACT

ACGTGAACCATCACCCTAATCAAGTTTTTTGGGGTCGAGGTGCCGTAAAGCACTAAA

TCGGAACCCTAAAGGGAGCCCCCGATTTAGAGCTTGACGGGGAAAGCCGGCGAACG

TGGCGAGAAAGGAAGGGAAGAAAGCGAAAGGAGCGGGCGCTAGGGCGCTGGCAAG

TGTAGCGGTCACGCTGCGCGTAACCACCACACCCGCCGCGCTTAATGCGCCGCTACA

GGGCGCGTACTATGGTTGCTTTGACGAGCACGTATAACGTGCTTTCCTCGTTAGAAT

CAGAGCGGGAGCTAAACAGGAGGCCGATTAAAGGGATTTTAGACAGGAACGGTAC

GCCAGAATCCTGAGAAGTGTTTTTATAATCAGTGAGGCCACCGAGTAAAAGAGTCT

GTCCATCACGCAAATTAACCGTTGTCGCAATACTTCTTTGATTAGTAATAACATCACT

TGCCTGAGTAGAAGAACTCAAACTATCGGCCTTGCTGGTAATATCCAGAACAATATT

ACCGCCAGCCATTGCAACAGGAAAAACGCTCATGGAAATACCTACATTTTGACGCT

CAATCGTCTGGAAATCCATTCGCCATTCAGGCTGCGCAACTGTTGGGAAGGGCGATC

GGTGCGGGCCTCTTCGCTATTACGCCAGCTGGCG
```

Aspects of the disclosure relate to recombinant adeno-associated virus (rAAV) particles for delivery of an rAAV vector as described herein (e.g., encoding an shRNA and/or a replacement RHO) into various tissues, organs, and/or cells. In some embodiments, the rAAV particles comprise a capsid protein as described herein, e.g., an AAV5 capsid protein. In some embodiments, the vector contained within the rAAV particle encodes an RNA of interest (e.g., an shRNA comprising the sequence of SEQ ID NO: 4) and comprises a replacement RHO coding sequence (e.g., comprising the sequence of SEQ ID NO: 5).

Recombinant AAV (rAAV) vectors contained within an rAAV particle may comprise at a minimum (a) one or more heterologous nucleic acid regions (e.g., encoding an shRNA and/or a RHO protein) and (b) one or more regions comprising inverted terminal repeat (ITR) sequences (e.g., wild-type ITR sequences or engineered ITR sequences) flanking the one or more heterologous nucleic acid regions. In some embodiments, the heterologous nucleic acid region encodes an RNA of interest (e.g., an shRNA comprising the sequence of SEQ ID NO: 4) and comprises a replacement RHO coding sequence (e.g., comprising the sequence of SEQ ID NO: 5). In some embodiments, the rAAV vector is between 4 kb and 5 kb in size (e.g., 4.2 to 4.7 kb in size). This rAAV vector may be encapsidated by a viral capsid, such as an AAV5 capsid. In some embodiments, the rAAV vector is single-stranded. In some embodiments, the rAAV vector is double-stranded. In some embodiments, a double-stranded rAAV vector may be, for example, a self-complementary vector that contains a region of the vector that is complementary to another region of the vector, initiating the formation of the double-strandedness of the vector.

The rAAV particle may be of any AAV serotype, including any derivative or pseudotype (e.g., 1, 2, 3, 4, 5, 6, 7, 8, 9, 10, 2/1, 2/5, 2/8, or 2/9). As used herein, the serotype of an rAAV particle refers to the serotype of the capsid proteins. In some embodiments, the rAAV particle is AAV5. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV218, AAV-HSC15/17, AAVM41, AAV9.45, AAV6 (Y445F/Y731F), AAV2.5T, AAV-HAE1/2, AAV clone 32/83, AAVShH10, AAV2 (Y->F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20 (4): 699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV5). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and rAAV vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US 2007/0015238 and US20120322861, which are incorporated herein by reference; and plasmids and kits available from ATCC and Cell Biolabs, Inc.). For example, a plasmid containing the rAAV vector may be combined with one or more helper plasmids, e.g., that contain a rep gene (e.g., encoding Rep78, Rep68, Rep52 and Rep40) and a cap gene (e.g., encoding VP1, VP2, and VP3, including a modified VP3 region as described herein), and transfected into a producer cell line such that the rAAV particle can be packaged and subsequently purified.

In some embodiments, the one or more helper plasmids include a first helper plasmid comprising a rep gene and a cap gene (e.g., encoding a rAAV capsid protein as described herein) and a second helper plasmid comprising a E1a gene, a E1b gene, a E4 gene, a E2a gene, and a VA gene. In some embodiments, the rep gene is a rep gene derived from AAV2 or AAV5 and the cap gene is derived from AAV2 or AAV5 and may include modifications to the gene in order to produce the modified capsid protein described herein. Helper plasmids, and methods of making such plasmids, are known in the art and commercially available (see, e.g., pDM, PDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, *Human Gene Therapy*, Vol. 9, 2745-2760; Kern, A. et al. (2003), Identification of a Heparin-Binding Motif on Adeno-Associated Virus Type 2 Capsids, *Journal of Virology*, Vol. 77, 11072-11081.; Grimm et al. (2003), Helper Virus-Free, Optically Controllable, and Two-Plasmid-Based Production of Adeno-associated Virus Vectors of Serotypes 1 to 6, *Molecular Therapy*, Vol. 7, 839-850; Kronenberg et al. (2005), A Conformational Change in the Adeno-Associated Virus Type 2 Capsid Leads to the Exposure of Hidden VP1 N Termini, *Journal of Virology*, Vol. 79, 5296-5303; and Moullier, P. and Snyder, R. O. (2008), International efforts for recombinant adeno-associated viral vector reference standards, *Molecular Therapy*, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise an shRNA, a vector, or an rAAV particle as described herein. Such host cells include mammalian host cells, with human host cells being preferred, and may be isolated, e.g., in cell or tissue culture. In some embodiments, the host cell is a cell of the eye.

The disclosure also contemplates host cells that comprise an shRNA, a vector, an rAAV particle, and the mRNA expressed after infection of the host cell by the rAAV particles described herein or transfection by the constructs described herein. In certain embodiments, the host cells provided herein comprise short mRNA sequences that are different from those found in nature. In certain embodiments, the host cells comprise short mRNA sequences having at least 95% or 99.5% sequence identity with any one of SEQ ID NOs: 40-46. The host cells may comprise short mRNA sequences comprising the sequence of any one of SEQ ID NOs: 40-46. Such host cells include mammalian host cells, with human host cells being preferred, and may be isolated, e.g., in cell or tissue culture. In some embodiments, the host cell is a cell of the eye.

Exemplary mammalian cells include human cells, rodent cells and canine cells. In some embodiments, the mammalian cells are derived from a human (e.g., a human having or known to have, for example diagnosed as having, retinitis pigmentosa, for example dominant retinitis pigmentosa).

In some embodiments, a composition is provided which comprises an shRNA, a vector, or an rAAV particle as described herein and optionally a pharmaceutically acceptable carrier. In some embodiments, the compositions described herein can be administered to a subject in need of treatment. In some embodiments, the subject has or is suspected of having one or more conditions, diseases, or disorders of the brain and/or eye (e.g., retinitis pigmentosa such as dominant retinitis pigmentosa). In some embodiments, the subject has or is suspected of having one or more of the conditions, diseases, and disorders disclosed herein (e.g., retinitis pigmentosa such as dominant retinitis pigmentosa). In some embodiments, the subject has one or more endogenous mutant rho alleles (e.g., associated with or that cause a disease or disorder of the eye or retina). In some embodiments, the subject has at least one dominant mutant rho allele (e.g., that causes dominant retinitis pigmentosa). In some embodiments, the subject is a human. In some embodiments, the subject is a non-human primate. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. Other exemplary subjects include domesticated animals such as dogs and cats; livestock such as horses, cattle, pigs, sheep, goats, and chickens; and other animals such as mice, rats, guinea pigs, and hamsters.

In some embodiments, the dose of rAAV particles administered to a cell or a subject may be on the order ranging from $10^6$ to $10^{14}$ particles/mL or $10^3$ to $10^{15}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are be administered. In some embodiments, the dose of rAAV particles administered to a subject may be on the order ranging from $10^6$ to $10^{14}$ vector genomes (vgs)/mL or $10^3$ to $10^{15}$ vgs/mL, or any values therebetween for either range, such as for example, about $10^6$, $10^7$, $10^8$, $10^9$, $10^{10}$, $10^{11}$, $10^{12}$, $10^{13}$, or $10^{14}$ vgs/mL. In one embodiment, rAAV particles of higher than $10^{13}$ vgs/mL are be administered. The rAAV particles can be administered as a single dose, or divided into two or more administrations as may be required to achieve therapy of the particular disease or disorder being treated. In some embodiments, 0.0001 mL to 10 mLs (e.g., 0.0001 mL, 0.001 mL, 0.01 mL, 0.1 mL, 1 mL, 10 mLs) are delivered to a subject in a dose.

In some embodiments, rAAV particle titers range from $1\times10^{10}$-$5\times10^{13}$ vg/ml. In some embodiments, rAAV particle titers can be $1\times10^{10}$, $2.5\times10^{10}$, $5\times10^{10}$, $1\times10^{11}$, $2.5\times10^{11}$, $5\times10^{11}$, $1\times10^{12}$, $2.5\times10^{12}$, $5\times10^{12}$, $1\times10^{13}$, $2.5\times10^{13}$, or $5\times10^{13}$ vg/mL. In some embodiments, particle titers are less than $1\times10^{10}$ vg/mL. In some embodiments, rAAV particle titers are greater than $1\times10^{15}$ vg/mL. In one embodiment, rAAV particle titers are greater than $5\times10^{13}$ vgs/mL. In some embodiments, rAAV particles are administered via methods further described herein (e.g., subretinally or intravitreally).

The rAAV particles can be administered as a single dose, or divided into two or more administrations as may be required to achieve therapy of the particular disease or disorder being treated. In some embodiments, the rAAV particles are administered over a period of days or weeks. In some embodiments, from 1 to 500 microliters of a composition (e.g., comprising an rAAV particle) described in this application is administered to one or both eyes of a subject. For example, in some embodiments, about 1, about 10, about 50, about 100, about 200, about 300, about 400, or about 500 microliters can be administered to each eye. However, it should be appreciated that smaller or larger volumes could be administered in some embodiments.

In some embodiments, the rAAV particles, compositions and methods of treatment disclosed herein preserve the integrity of the structure of rod photoreceptors in the subject, preserve ONL thickness and/or confer protection from degeneration of at least about 12 weeks, at least about 18 weeks, at least about 24 weeks, at least about 30 weeks, at least about 36 weeks, at least about 42 weeks, at least about 48 weeks, at least about 54 weeks, or at least about 60 weeks for retinal structure and function in the subject following a single administration to the eye.

In some embodiments, the disclosure provides formulations of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particle or nucleic acid vectors may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, and intramuscular administration and formulation.

Typically, these formulations may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver an shRNA, a vector, or an rAAV particle as described herein in suitably formulated pharmaceutical compositions disclosed herein either subcutaneously, intraocularly, intravitreally, parenterally, subcutaneously, intravenously, intracerebroventricularly, intramuscularly, intrathecally, orally, intraperitoneally, by oral or nasal inhalation, or by direct injection to one or more cells, tissues, or organs by direct injection.

The pharmaceutical forms of compositions (e.g., comprising an shRNA, a vector, or an rAAV particle as described herein) suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the shRNA, vector, or rAAV particle as described herein is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be delivered to the eye through a variety of routes. They may be delivered intraocularly, by topical application to the eye or by intraocular injection into, for example the vitreous (intravitreal injection) or subretinal (subretinal injection) interphotoreceptor space. In some embodiments, they are delivered to rod photoreceptor cells. Alternatively, they may be delivered locally by insertion or injection into the tissue surrounding the eye. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. They can be administered prior to the onset of the condition, to prevent its occurrence, for example, during surgery on the eye, or immediately after the onset of the pathological condition or during the occurrence of an acute or protracted condition.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions may be prepared by incorporating an shRNA, a vector, or an rAAV particle as described herein in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of composition (e.g., comprising an shRNA, a vector, or an rAAV particle as described herein) and time of administration of such composition will be within the purview of the skilled artisan having benefit of the present teachings. It is likely, however, that the administration of therapeutically-effective amounts of the disclosed compositions may be achieved by a single administration, such as for example, a single injection of sufficient numbers of rAAV particles to provide therapeutic benefit to the patient undergoing such treatment. Alternatively, in some circumstances, it may be desirable to provide multiple, or successive administrations of the composition, either over a relatively short, or a relatively prolonged period of time, as may be determined by the medical practitioner overseeing the administration of such compositions.

In some embodiments, rod cells remain structurally intact and/or viable upon silencing of cellular rhodopsin gene expression. In some embodiments, rods cells in which cellular rhodopsin gene expression is silenced have shortened outer segments which would normally contain rhodopsin. In some embodiments, the length of the outer segments can be maintained or restored (e.g., partially or completely) using the exogenously added (hardened) rhodopsin gene, the expression of which is resistant to silencing using the compositions described in this application. In some embodiments, administration of a composition described herein to a subject having retinitis pigmentosa (e.g., dominant retinitis pigmentosa) preserves the integrity of the structure of rod photoreceptors in the subject, preserves ONL thickness and/or confers protection from degeneration of at least about 12 weeks, at least about 18 weeks, at least about 24 weeks, at least about 30 weeks, at least about 36 weeks, at least about 42 weeks or at least about 48 weeks, at least about 54 weeks, or at least about 60 weeks for retinal structure and function in the subject.

To "treat" a disease as the term is used herein, means to reduce the frequency or severity of at least one sign or symptom of a disease or disorder experienced by a subject (e.g., retinitis pigmentosa). The compositions described above are typically administered to a subject in an effective amount, that is, an amount capable of producing a desirable result. The desirable result will depend upon the active agent being administered. For example, an effective amount of a rAAV particle may be an amount of the particle that is capable of transferring a heterologous nucleic acid to a host organ, tissue, or cell.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Figure 6:
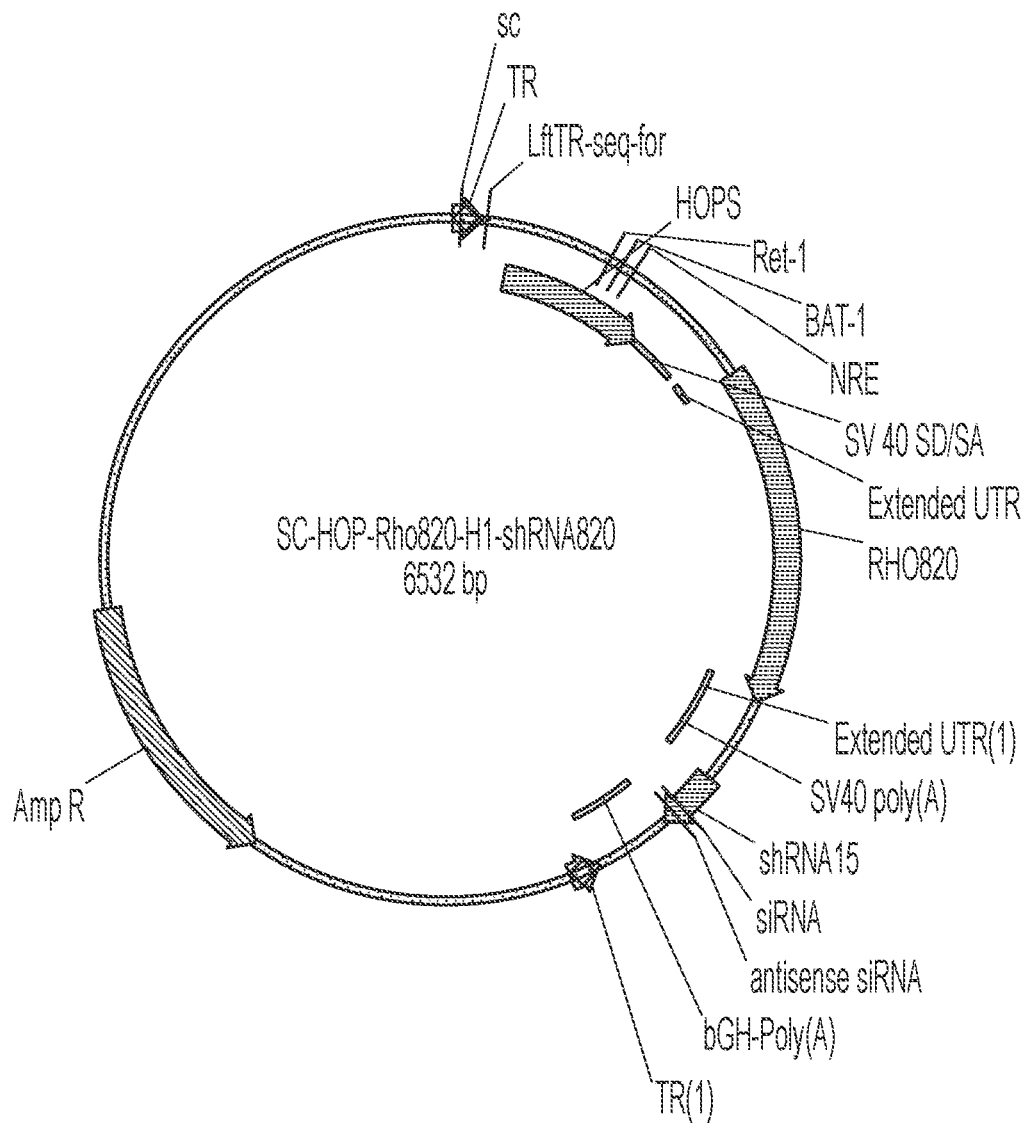
FIG. 6 shows a diagram of the transgene plasmid AAV-shRNA$_{820}$-RHO$_{820}$.

Inherited retinal degenerations are caused by mutations in >250 genes that affect photoreceptor cells or the retinal pigment epithelium and cause vision loss. For autosomal recessive and X-linked retinal degenerations, significant progress has been achieved in the field of gene therapy as evidenced by the growing number of clinical trials, and the recent commercialization of the first gene therapy for a form of congenital blindness. However, in spite of significant efforts to develop a treatment for the most common form of autosomal dominant retinitis pigmentosa (adRP) caused by >150 mutations in the rhodopsin (RHO) gene, translation to the clinic has stalled. Here, a highly efficient novel short hairpin RNA (shRNA) was first identified that targets human (and canine) RHO in a mutation-independent manner. In a single adeno-associated viral (AAV) vector, this shRNA was combined with a human RHO replacement cDNA made resistant to RNA interference, and this construct (referred to hereafter as "scAAV2/5-RHO$_{820}$-shRNA$_{820}$", see FIG. 6) was tested in a naturally-occurring canine model of RHO-adRP. Subretinal vector injections led to near complete suppression of endogenous canine RHO RNA while the human RHO replacement cDNA resulted in up to 30% of normal RHO protein levels. Non-invasive retinal imaging showed complete protection of photoreceptors from retinal degeneration in treated areas. Histopathology confirmed retention of normal photoreceptor structure and RHO expression in rod outer segments. Long-term (>8 months) follow-up by retinal imaging and electroretinography indicated stable structural and functional preservation. Efficacy of this gene therapy in a clinically relevant large animal model paves the way for treating patients with RHO-adRP.

The past two decades have seen a steep rise in the number of gene therapies entering clinical trials (1, 2) and in recent years a small number of them have received marketing approval by regulatory authorities in China, Europe and the US.(3) The vast majority of these trials have targeted cancer, cardiovascular, and inherited monogenic diseases.(1) Strategies for inherited monogenic diseases are by necessity based on the mechanism of disease. For the vast majority of loss of function mutations, the strategy is gene augmentation.(4) For mutations that cause a dominant-negative effect, gene augmentation may also provide some therapeutic benefit by diluting the deleterious effect of the mutant product. (5, 6) However, in the case of mutations that confer a toxic gain-of-function, strategies that are being investigated include ablation of the gene or correction of the defect at the DNA level (e.g. CRISPR/Cas9 gene editing), transcriptional repression, and RNA knockdown/suppression.(7, 8)

Mutations in more than 250 genes are known to cause inherited retinal diseases (sph.uth.edu/retnet/), and considerable advances have been made in gene therapy approaches because of the accessibility of the retina. Clinical trials of gene augmentation are currently ongoing for at least six autosomal recessive, three X-linked, and one maternally-inherited mitochondrial retinal diseases.(9) There are no trials for autosomal dominant retinal diseases, the most common of which is autosomal dominant retinitis pigmentosa (adRP) caused by mutations in the rhodopsin (RHO) gene.(10-14) For the more than 150 identified RHO mutations, several putative pathogenic mechanisms based mostly on in vitro findings have been proposed (for reviews see 15, 16), yet detailed characterization of RHO-adRP patient phenotype is consistent with two major categories.(17-19) Class A mutant patients have severe loss of rods from early life, and realistic therapeutic approaches should be directed at prolonging cone survival. On the other hand, patients with Class B mutants can have rods that survive for decades into late adult life in some retinal regions or throughout the retina, and could benefit from a gene therapy aimed at rescuing the remaining rods and preventing secondary cone cell loss.(20)

Over the past 20 years, efforts on gene therapy for RHO-adRP have focused on either reducing expression of specific mutant alleles (21-28), or developing a mutation-independent strategy. The latter strategy combines knocking down the expression of both the mutant and wild type (WT) RHO proteins (29-39) while providing as replacement a resistant RHO cDNA that encodes the WT protein.(40-43) Resistance is conferred by codon modification at degenerate/wobble nucleotides within the target site, which prevents hybridization with the knockdown reagent. Such mutation-independent "knockdown and replacement" strategy aims at addressing the high allelic heterogeneity in RHO-adRP, while circumventing the technical and financial challenges that would be inherent in developing multiple gene therapies for individual RHO mutations. The retinal co-delivery of the two components using either two separate (42), or a single AAV vector (41, 43) have been explored in transgenic mice by separate research groups. However complete prevention or arrest of the ongoing rod degeneration was not achieved.

Here, a highly effective short hairpin RNA, shRNA$_{820}$, was identified that targets human RHO in a mutation-independent manner. When combined with a resistant form of human RHO, and co-packaged in a single recombinant adeno-associated viral (AAV) particle, this construct with dual knockdown and replacement functions provided long-term protection against retinal degeneration in a naturally-occurring canine model of RHO-adRP.

Results

Optimal Suppression of Wild-Type Rhodopsin with shRNA$_{820}$

Figure 1F:
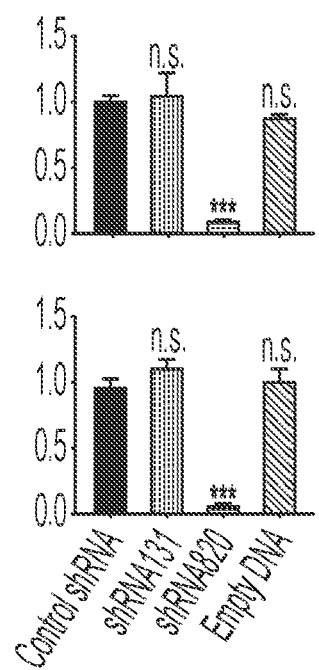
Figure 7:
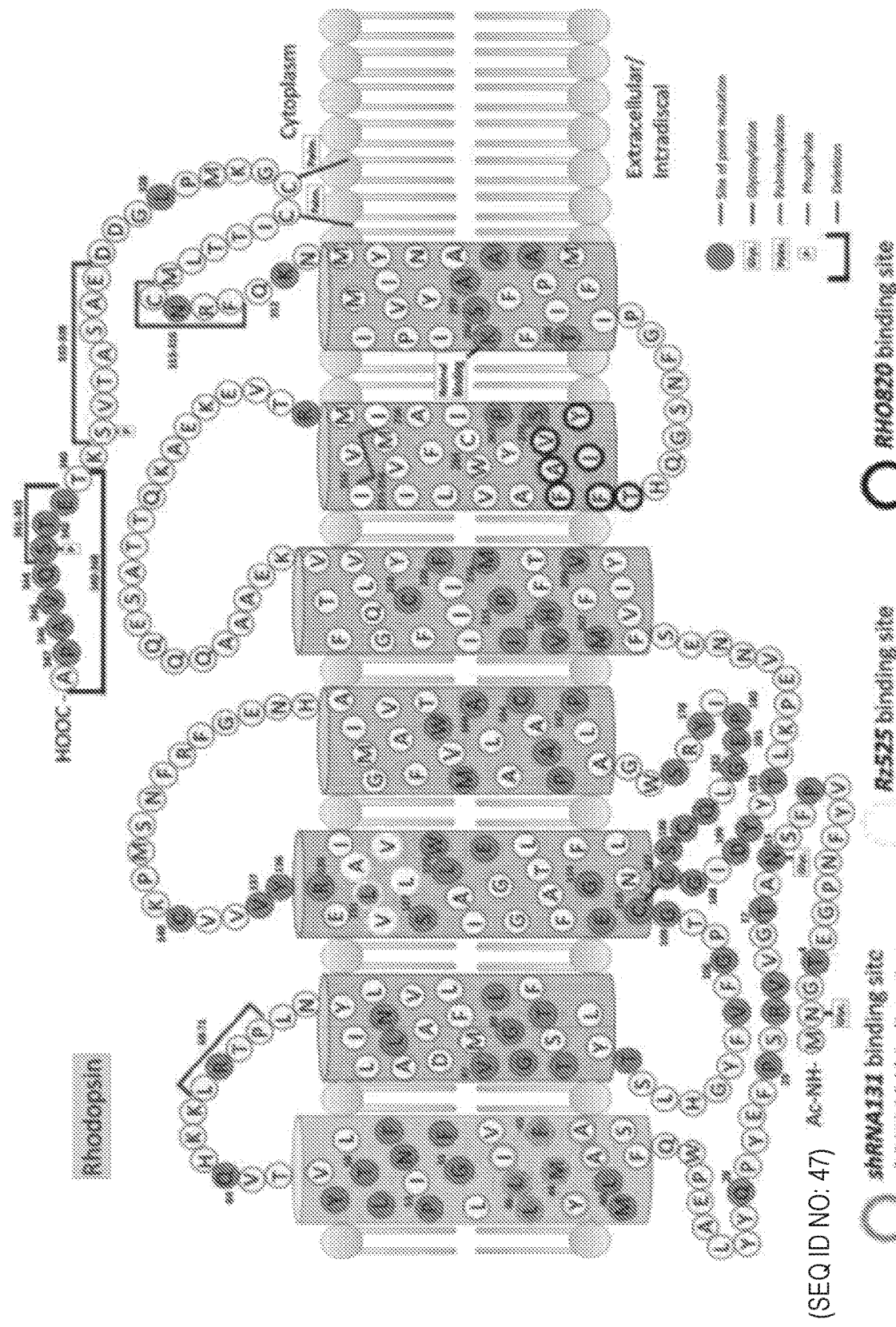
FIG. 7 shows an amino acid sequence of human rhodopsin illustrating sites of known mutations and deletions (based on review from Athanasiou et al. (15)) and target sites of shRNAs and ribozyme knock down reagents evaluated in this current study.
Figure 8:
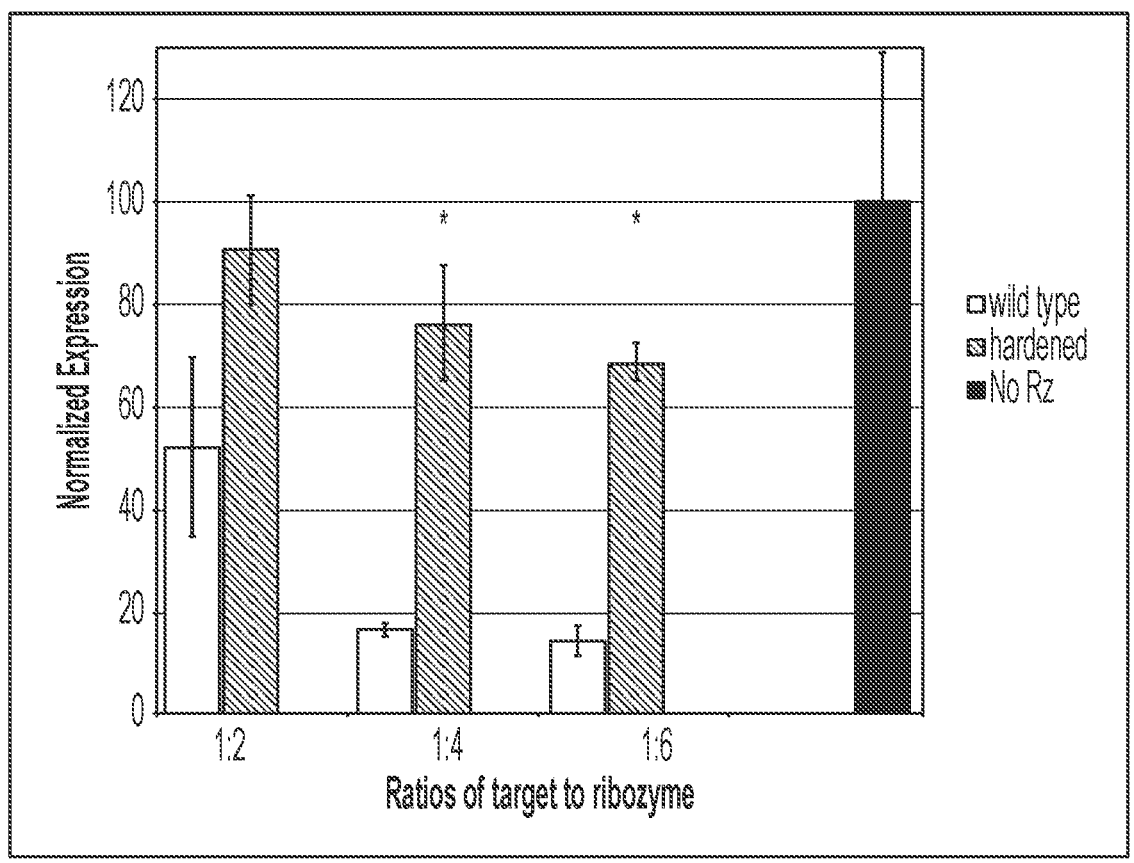
FIG. 8 shows the digestion of human rhodopsin mRNA by hammerhead ribozyme 525 (Rz525). Levels of wild type (white bar) or resistant/hardened (diagonal line shaded bar) RHO transcripts measured by luciferase assay in HEK293 cells co-transfected with a plasmid expressing Rz525. Results were normalized to the same fusion transcript measured following co-transfection with a plasmid lacking ribozyme (black bar). Error bars represent standard error of the mean. *=P<0.05 for resistant/hardened RHO relative to wild type RHO by Student's t test.

Four knockdown reagents, including a previously identified (33) hammerhead ribozyme (Rz525), and three novel shRNAs (shRNA$_{131}$, shRNA$_{134}$, shRNA$_{820}$) that target distinct homologous regions of canine and human RHO (FIG. 7), were screened initially using in vitro assays. Silencing of RHO expression was very effective with Rz525 both in vitro (FIG. 8), and in WT (FIGS. 9A-9C; Table 1, group C) and RHO-mutant canine eyes (FIGS. 10A-10C; Table 1, group F). However, due to severe retinal complications associated with the high viral titers of AAV2/5-Rz525 needed to achieve near complete suppression of RHO expression (Results below and FIGS. 10D-10E), further development of Rz525 was discontinued. In vitro screening of shRNAs showed that shRNA$_{131}$ resulted in only ~50% reduction of WT human RHO protein (FIGS. 1A, 1B), and failed to suppress mutant human RHO P23H (FIGS. 1C, 1D) and T17M (FIGS. 1E, 1F). Moreover, there was limited suppression of RHO expression in injected canine WT eyes (Results below, FIGS. 11A-11C, Table 1, group B).

Figure 1G:
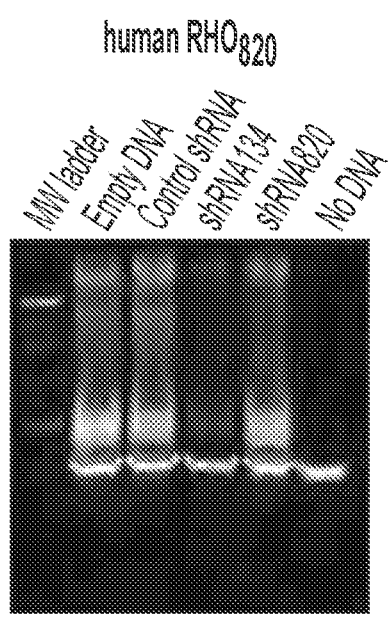
Figure 1H:
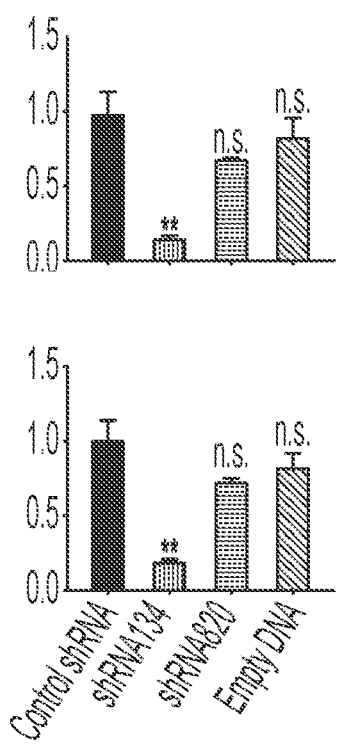

The most potent shRNA to suppress expression of both WT and mutant (P23H and T17M) human RHO protein in vitro was shRNA$_{820}$ (FIGS. 1A-1F). In parallel, codon-modified form of human RHO, RHO$_{820}$, that contained four altered nucleotides at degenerate/wobble positions within the target site of shRNA$_{820}$ was confirmed to be resistant to shRNA$_{820}$ suppression (FIGS. 1G, 1H). Once confirmed that shRNA$_{820}$ targeted RHO in a mutation-independent manner, it was selected as the lead knockdown reagent for further evaluation in WT and RHO-mutant dogs.

Figure 2A:
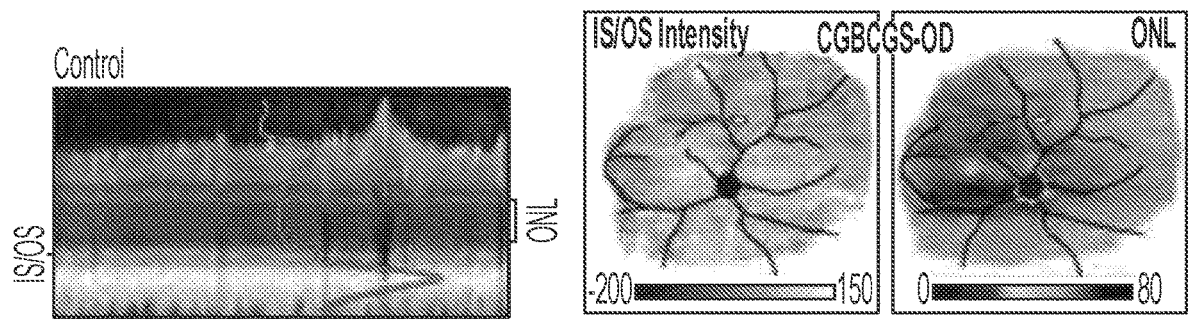
Figure 2B:
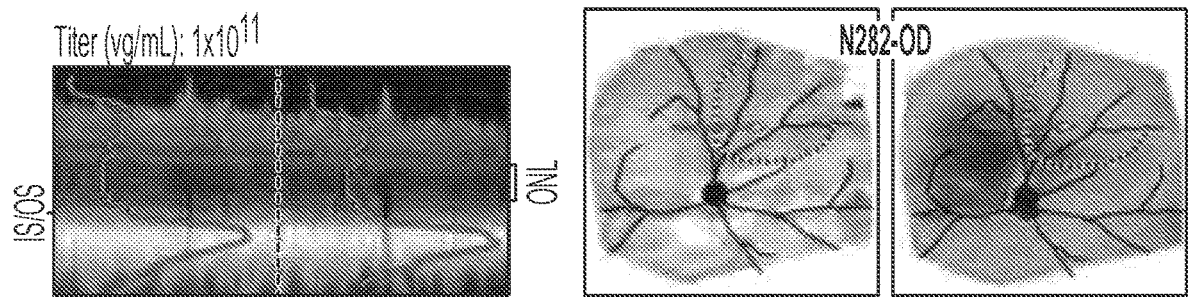
Figure 2C:
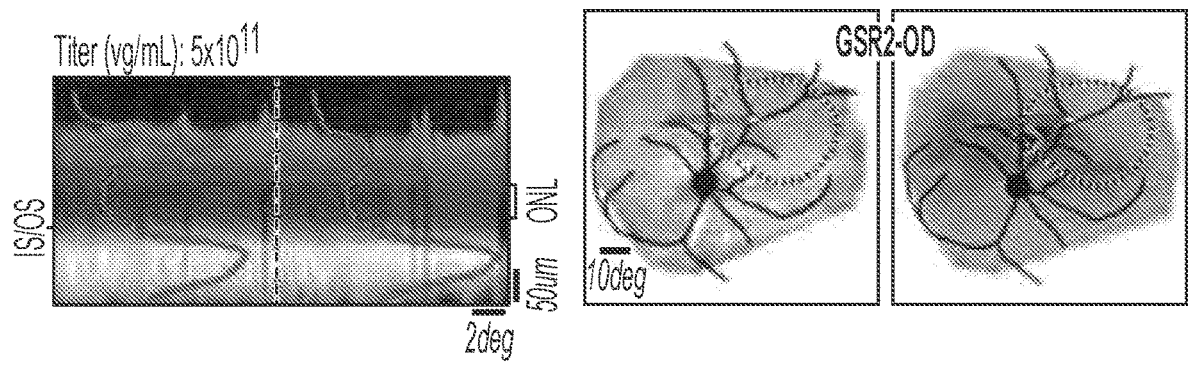

Validation of shRNA$_{820}$ was performed first in WT dogs to determine the titer at which RHO expression can be substantially reduced with expected changes occurring only in outer segments, where RHO is a major signaling and structural protein, but without major stress or degeneration of the remaining cellular compartments of rod photoreceptors. Subretinal injections were performed in ten WT canine eyes with AAV-shRNA820 titers ranging from 1× to 50×10$^{11}$ vg/mL (Table 1, group A). Treated eyes were evaluated at 7-8 weeks post-injection by in-life spectral-domain optical coherence tomography (OCT) imaging of the retinal structure and compared to uninjected control eyes. In a representative uninjected WT eye, cross-sectional imaging in the superior retina with OCT revealed hypo- and hyper-scattering layers corresponding to different retinal lamina (FIG. 2A, left). (44) The thickness of the outer nuclear layer (ONL) where the photoreceptor nuclei reside, and the backscatter intensity originating near the inner segment-outer segment (IS/OS) junction were of primary interest to this study (FIG. 2A, left). IS/OS intensity is expected to be sensitive to changes in outer segment length, alignment and spatial density, and thus can be used as a non-invasive surrogate measure of outer segment health. The normalized IS/OS intensity topography of the uninjected WT tends to be uniform (FIG. 2A, middle column). ONL thickness topography in the uninjected WT eye was also relatively homogeneous with incrementally greater values in the central retina superotemporal to the optic nerve head (ONH), and incrementally smaller values in the non-tapetal areas of superior and inferior retina (FIG. 2A, right column). Lower and intermediate titer injections represented by eyes injected with vector at 1×10$^{11}$ vg/mL (FIG. 2B), or 5×10$^{11}$ vg/mL (FIG. 2C) showed no qualitative structural changes between the injected and neighboring uninjected regions.

Figure 12:
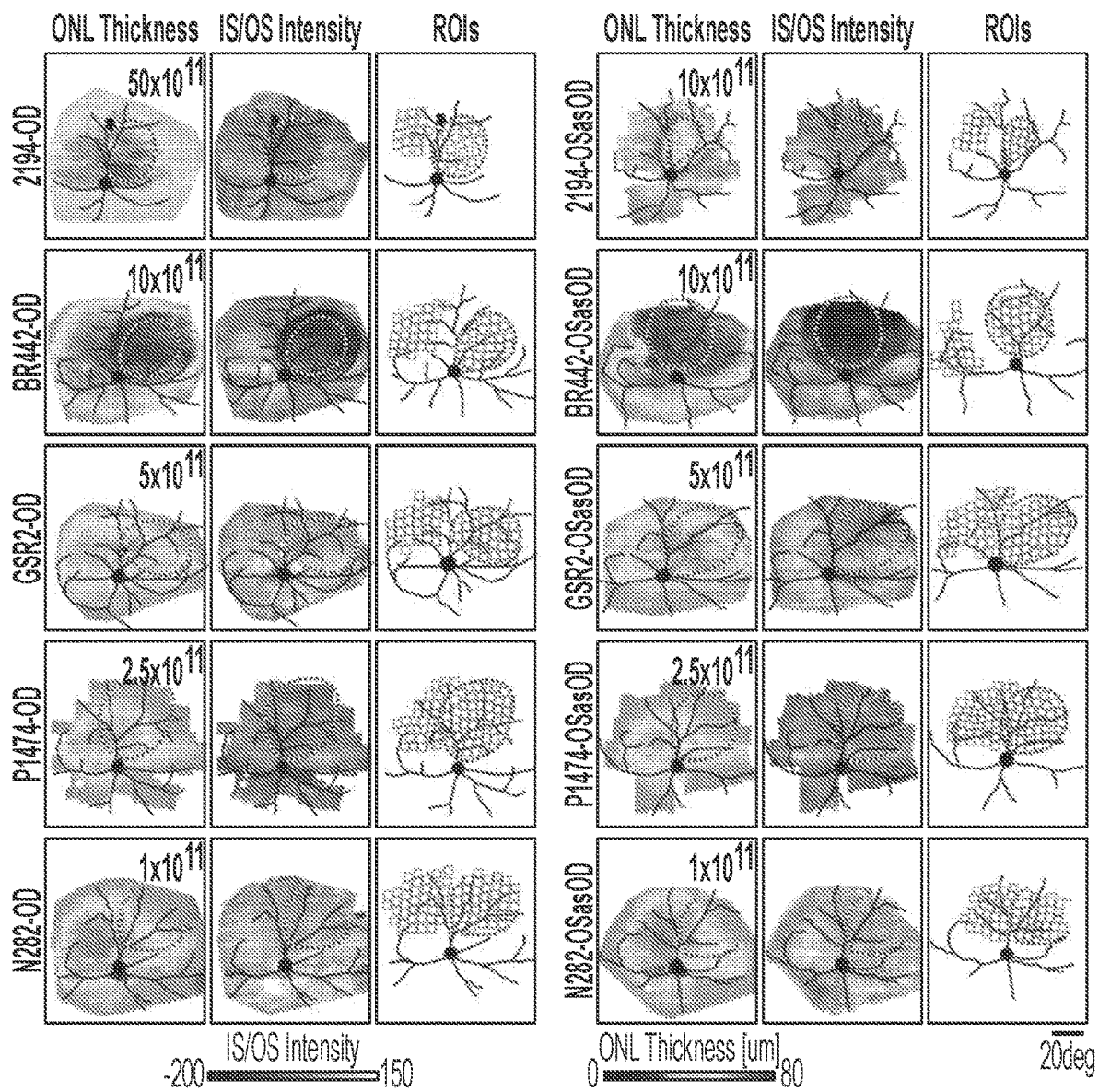
FIG. 12 shows individual topographic results of all 10 RHO WT eyes injected with scAAV2/5-shRNA$_{820}$ over a range of titers from 1× to 50×10$^{11}$ vg/mL. ONL thickness (left), normalized IS/OS intensity (middle) and loci chosen within (squares on the right with surrounding dotted line) and outside (squares on the left) the bleb (right) for quantitation. 2194-OD and similar labels designate the individual animal and eye. All eyes are shown as equivalent right eyes to allow easier comparison. OSasOD designation refers to left eye being displayed as right eye for comparability.

To define the optimal titer at which structural consequences of RHO knockdown are detectable but mild, retinal locations were systematically sampled (FIG. 12). A great majority of the injected locations for the two lowest titers (1× and 2.5×10$^{11}$ vg/mL) were comparable to uninjected control eyes with respect to IS/OS intensity and ONL thickness (FIGS. 2D, 2E, upper panels). In contrast, a great majority of the injected locations for the two highest titers (10×10$^{11}$ and 50×10$^{11}$ vg/mL) showed reduced IS/OS intensity expected from RHO knockdown (FIG. 2D) and some ONL thickening suggesting photoreceptor stress (FIG. 2E). Transition to detectable changes occurred between 5×10$^{11}$ and 8×10$^{11}$ vg/mL (FIGS. 2D, 2E, arrows) suggesting a range of potentially optimal titer. The great majority of the loci at uninjected sites in the treated eyes at all titers were consistent with results expected from uninjected eyes confirming the localization of the effects of RHO knockdown to the area of the subretinal injection (FIGS. 2D, 2E lower panels).

Figure 2G:
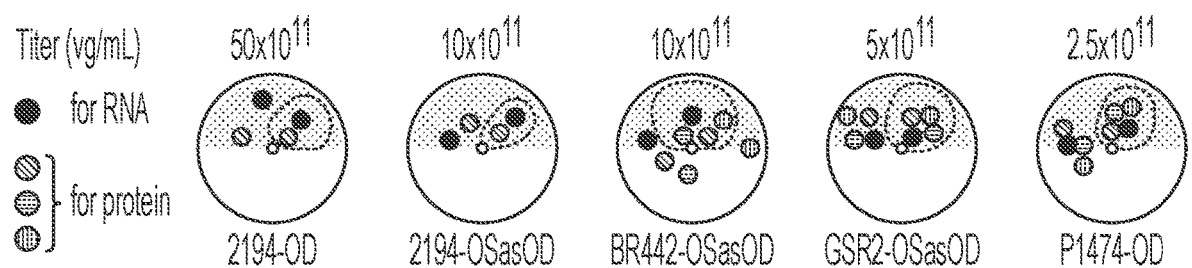
Figure 2H:
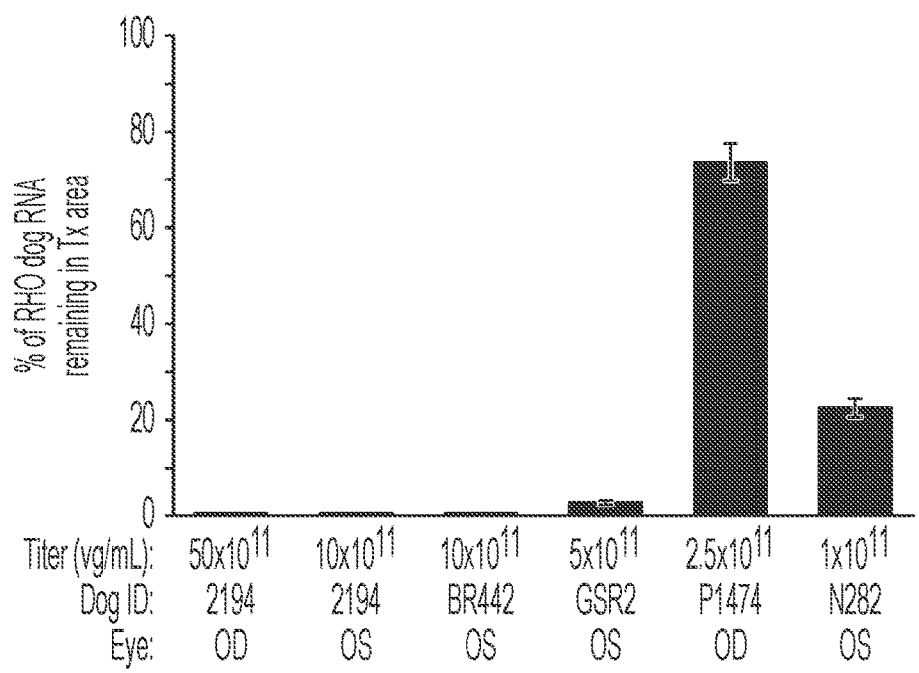

Animals were humanely euthanized at 7 to 8 weeks post-injection, and four eyes that had been treated with titers ranging from 1× to 10×10$^{11}$ vg/mL were processed for histology and rhodopsin immunohistochemistry (FIG. 2F). No obvious qualitative differences in ONL thickness were seen between treated and untreated areas of each eye suggesting that the thickening of the ONL seen by OCT imaging with high viral titers was likely the result of inter or intra cellular swelling (undetectable after tissue fixation) but not cell proliferation. Loss of outer segment structure associated with a prominent reduction of rod opsin immunolabeling was seen in the area treated with the 10×10$^{11}$ vg/mL titer vector. At 5×10$^{11}$ vg/mL some shortening of outer segments and reduction of rod opsin immunolabeling was found in the treated area when compared to the untreated area of the same eye. At the two lowest titers (1× and 2.5×10$^{11}$ vg/mL), outer segments were preserved and rod opsin immunolabeling was comparable between treated and untreated areas. The remaining six eyes injected with titers ranging from 1×10$^{11}$ to 50×10$^{11}$ vg/mL (FIG. 2G) were used to assess the efficiency of AAV-shRNA$_{820}$ in reducing expression of endogenous canine RHO both at the RNA and protein level. Absolute RNA quantification (FIG. 2H) showed very low levels of RHO transcripts (0-3% of that found in untreated areas) in the treated areas of eyes injected with titers ranging from 50×10$^{11}$ down to 5×10$^{11}$ vg/mL. At lower titers (1×10$^{11}$ to 2.5×10$^{11}$ vg/mL) knockdown efficiency was reduced with 22 to 74% of normal RHO RNA levels still remaining in the treated areas. Quantification of RHO protein persisting in the treated areas on immunoblots revealed a dose-dependent effect (FIG. 2H), with undetectable levels in eyes treated with the two highest titers (50×10$^{11}$ and 10×10$^{11}$ vg/mL), 15% in the eye treated with 5×10$^{11}$ vg/mL, and >47% with the two lowest titers.

These studies showed that subretinal AAV vector delivery of shRNA$_{820}$ can achieve very efficient silencing of WT canine RHO, and suggested that the 5×10$^{11}$ vg/mL titer may provide the optimal balance between knockdown of a highly-expressed structural protein in rod photoreceptors without causing major photoreceptor stress or degeneration.

TABLE 1

Summary of the experimental procedures performed in dogs.

| Study/group | Dog ID-eye | Sex | Treatment | Titer (vg/mL) | Volume (μL) |
|---|---|---|---|---|---|
| \multicolumn{6}{c}{RHO Knockdown alone in Normal eyes} | | | | | |
| A | 2194-OD | F | shRNA820 | $50 \times 10^{11}$ | 200 (50 IVit) |
|  | 2194-OS | F | shRNA820 | $10 \times 10^{11}$ | 300 (250 IVit) |
|  | BR442-OD | F | shRNA820 | $10 \times 10^{11}$ | 200 (50 IVit) |
|  | BR442-OS | F | shRNA820 | $10 \times 10^{11}$ | 150 |
|  | GSR2-OD | F | shRNA820 | $5 \times 10^{11}$ | 300 (150 IVit) |
|  | GSR2-OS | F | shRNA820 | $5 \times 10^{11}$ | 150 (40 IVit) |
|  | P1474-OD | M | shRNA820 | $2.5 \times 10^{11}$ | 200 (50 IVit) |
|  | P1474-OS | M | shRNA820 | $2.5 \times 10^{11}$ | 150 |
|  | N282-OD | M | shRNA820 | $1 \times 10^{11}$ | 150 |
|  | N282-OS | M | shRNA820 | $1 \times 10^{11}$ | 160 |
| B | 2190-OD | M | shRNA131 | $50 \times 10^{11}$ | 150 |
|  | 2190-OS | M | shRNA131 | $10 \times 10^{11}$ | 150 |
| C | D345-OD | F | Rz525 | $50 \times 10^{11}$ | 150 |
|  | AS355-OS | F | Rz525 | $20 \times 10^{11}$ | 150 |
|  | AS357-OS | F | Rz525 | $20 \times 10^{11}$ | 150 |
| \multicolumn{6}{c}{RHO Knockdown alone in $RHO^{T4R/+}$ mutant eyes} | | | | | |
| D | EM408-OD | F | shRNA820 | $10 \times 10^{11}$ | 200 (50 IVit) |
|  | EM409-OD | F | shRNA820 | $10 \times 10^{11}$ | 150 |
|  | EM411-OD | F | shRNA820 | $5 \times 10^{11}$ | 160 |
|  | EM413-OD | F | shRNA820 | $2.5 \times 10^{11}$ | 150 |
|  | EM412-OD | F | shRNA820 | $1 \times 10^{11}$ | 220 (70 IVit) |
| E | EM408-OS | F | shRNA820 | $10 \times 10^{11}$ | 150 |
|  | EM409-OS | F | shRNA820 | $10 \times 10^{11}$ | 150 |
|  | EM411-OS | F | shRNA820 | $5 \times 10^{11}$ | 150 |
|  | EM413-OS | F | shRNA820 | $2.5 \times 10^{11}$ | 150 |
|  | EM412-OS | F | shRNA820 | $1 \times 10^{11}$ | 150 |
| F | EM396-OD | M | Rz525 | $100 \times 10^{11}$ | 150 |
|  | EM375-OD | M | Rz525 | $20 \times 10^{11}$ | 300 (150 IVit) |
|  | EM400-OD | F | Rz525 | $20 \times 10^{11}$ | 150 (40 subRPE) |
|  | EM400-OS | F | BSS | / | 150 |
|  | EM396-OS | M | Rz525 | $100 \times 10^{11}$ | 150 |
|  | EM375-OS | M | Rz525 | $20 \times 10^{11}$ | 450 (300 IVit) |
| \multicolumn{6}{c}{RHO Knockdown and Replacement: two vector strategy in $RHO^{T4R/+}$ mutant eyes} | | | | | |
| G | EM422-OD | M | (shRNA820) + (RHO820) | $5 \times 10^{11} + 5 \times 10^{11}$ | 150 |
|  | EM423-OD | M | (shRNA820) + (RHO820) | $5 \times 10^{11} + 10 \times 10^{11}$ | 150 |
|  | EM422-OS | M | (shRNA820) + (RHO820) | $5 \times 10^{11} + 5 \times 10^{11}$ | 150 |
|  | EM423-OS | M | (shRNA820) + (RHO820) | $5 \times 10^{11} + 10 \times 10^{11}$ | 150 |
| \multicolumn{6}{c}{RHO Knockdown and Replacement: single vector strategy in $RHO^{T4R/+}$ mutant eyes} | | | | | |
| H | EM418-OD | M | (shRNA820 + RHO820) | $5 \times 10^{11}$ | 150 |
|  | EM420-OD | F | (shRNA820 + RHO820) | $5 \times 10^{11}$ | 150 |
|  | EM424-OD | M | (shRNA820 + RHO820) | $5 \times 10^{11}$ | 150 |
|  | EM425-OD | M | (shRNA820 + RHO820) | $5 \times 10^{11}$ | 150 |
|  | EM418-OS | M | (shRNA820 + RHO820) | $5 \times 10^{11}$ | 150 |
|  | EM420-OS | F | (shRNA820 + RHO820) | $5 \times 10^{11}$ | 150 |
|  | EM424-OS | M | (shRNA820 + RHO820) | $5 \times 10^{11}$ | 150 |
|  | EM425-OS | M | (shRNA820 + RHO820) | $5 \times 10^{11}$ | 150 |
| \multicolumn{6}{c}{RHO Knockdown and Replacement: single vector strategy in $RHO^{T4R/+}$ mutant eyes (Long-term follow-up after multiple LD exposures)} | | | | | |
| I | EM426-OD | M | (shRNA820 + RHO820) | $5 \times 10^{11}$ | 150 |
|  | EM428-OD | F | (shRNA820 + RHO820) | $5 \times 10^{11}$ | 150 |
|  | EM426-OS | M | BSS | / | 150 |
|  | EM428-OS | F | BSS | / | 150 |
| \multicolumn{6}{c}{Natural history in $RHO^{T4R/+}$ mutant eyes (uninjected eyes or pre-injection time points)} | | | | | |
| J | EM414-OD | M | None | / | / |
|  | EM392-OD | M | None | / | / |
|  | EM392-OS | M | None | / | / |
|  | EM393-OD | F | None | / | / |
|  | EM393-OS | F | None | / | / |
|  | EM354-OD | F | None | / | / |
|  | EM191-OD | M | None | / | / |
|  | EM191-OS | M | None | / | / |
| \multicolumn{6}{c}{WT Control eyes} | | | | | |
| K | CGBCAN-OD | M | None | / | / |
|  | CGBCDI-OD | M | None | / | / |
|  | CGBCGS-OD | M | None | / | / |

TABLE 1-continued

Summary of the experimental procedures performed in dogs.

| | N292-OS | M | None | / | / |
|---|---|---|---|---|---|
| | N293-OS | F | None | / | / |
| | N294-OS | F | None | / | / |

| Study/group | Dose (vg/eye) | Lights | LE | Analysis | FIG. |
|---|---|---|---|---|---|
| *RHO Knockdown alone in Normal eyes* | | | | | |
| A | $100 \times 10^{10}$ | white | No | cSLO/OCT; RNA/protein | FIGS. 2A-2H; 12 |
| | $30 \times 10^{10}$ | white | No | cSLO/OCT; RNA/protein | FIGS. 2A-2H; 12 |
| | $20 \times 10^{10}$ | white | No | cSLO/OCT;H&E/IHC | FIGS. 2A-2H; 12 |
| | $15 \times 10^{10}$ | white | No | cSLO/OCT; RNA/protein | FIGS. 2A-2H; 12 |
| | $15 \times 10^{10}$ | white | No | cSLO/OCT;H&E/IHC | FIGS. 2A-2H; 12 |
| | $7.5 \times 10^{10}$ | white | No | cSLO/OCT; RNA/protein | FIGS. 2A-2H; 12 |
| | $5 \times 10^{10}$ | white | No | cSLO/OCT; RNA/protein | FIGS. 2A-2H; 12 |
| | $3.7 \times 10^{10}$ | white | No | cSLO/OCT;H&E/IHC | FIGS. 2A-2H; 12 |
| | $1.5 \times 10^{10}$ | white | No | cSLO/OCT;H&E/IHC | FIGS. 2A-2H; 12 |
| | $1.6 \times 10^{10}$ | white | No | cSLO/OCT; RNA/protein | FIGS. 2A-2H; 12 |
| | | white | | | |
| B | $75 \times 10^{10}$ | white | No | RNA/protein | FIGS. 11A-11C |
| | $15 \times 10^{10}$ | white | No | RNA/protein | FIGS. 11A-11C |
| | | white | | | |
| C | $75 \times 10^{10}$ | white | No | RNA/protein | FIGS. 9A-9C |
| | $30 \times 10^{10}$ | white | No | RNA/protein | FIGS. 9A-9C |
| | $30 \times 10^{10}$ | white | No | RNA/protein | FIGS. 9A-9C |
| *RHO Knockdown alone in $RHO^{T4R/+}$ mutant eyes* | | | | | |
| D | $20 \times 10^{10}$ | red | No | cSLO/OCT | |
| | $15 \times 10^{10}$ | red | No | cSLO/OCT; RNA/protein | FIGS. 3A-3D |
| | $8 \times 10^{10}$ | red | No | cSLO/OCT; RNA/protein | FIGS. 3A-3D |
| | $3.7 \times 10^{10}$ | red | No | cSLO/OCT; RNA/protein | FIGS. 3A-3D |
| | $2.2 \times 10^{10}$ | red | No | cSLO/OCT; RNA/protein | FIGS. 3A-3D |
| E | $15 \times 10^{10}$ | red | Yes | cSLO/OCT | FIGS. 15A-15C |
| | $15 \times 10^{10}$ | red | Yes | cSLO/OCT;H&E/IHC | FIGS. 3A-3D; 15A-15C |
| | $7.5 \times 10^{10}$ | red | Yes | cSLO/OCT;H&E/IHC | FIGS. 3A-3D; 15A-15C |
| | $3.7 \times 10^{10}$ | red | Yes | cSLO/OCT;H&E/IHC | FIGS. 3A-3D; 15A-15C |
| | $1.5 \times 10^{10}$ | red | Yes | cSLO/OCT;H&E/IHC | FIGS. 3A-3D; 15A-15C |
| F | $150 \times 10^{10}$ | white | No | cSLO/OCT; RNA/protein | FIGS. 10A-10E |
| | $60 \times 10^{10}$ | white | No | cSLO/OCT; RNA/protein | FIGS. 10A-10E |
| | $30 \times 10^{10}$ | white | No | RNA/protein | FIGS. 10A-10E |
| | / | white | No | RNA/protein | FIGS. 10A-10E |
| | $150 \times 10^{10}$ | white | Yes | cSLO/OCT; H&E | FIGS. 10A-10E |
| | $90 \times 10^{10}$ | white | Yes | cSLO/OCT | |
| *RHO Knockdown and Replacement: two vector strategy in $RHO^{T4R/+}$ mutant eyes* | | | | | |
| G | $15 \times 10^{10}$ | red | No | cSLO/OCT | |
| | $22.5 \times 10^{10}$ | red | No | cSLO/OCT | FIGS. 13A-13G |
| | $15 \times 10^{10}$ | red | Yes | cSLO/OCT; H&E/IHC | FIGS. 13A-13G; 15A-15C |
| | $22.5 \times 10^{10}$ | red | Yes | cSLO/OCT; H&E/IHC | FIGS. 13A-13G |
| H | $7.5 \times 10^{10}$ | red | No | RNA/protein | FIGS. 4A-4G |
| | $7.5 \times 10^{10}$ | red | No | RNA/protein | FIGS. 4A-4G |
| | $7.5 \times 10^{10}$ | red | No | RNA/protein | FIGS. 4A-4G |
| | $7.5 \times 10^{10}$ | red | No | RNA/protein | FIGS. 4A-4G |
| | $7.5 \times 10^{10}$ | red | Yes | cSLO/OCT; IHC | FIGS. 4A-4G; 15A-15C |
| | $7.5 \times 10^{10}$ | red | Yes | cSLO/OCT; IHC | FIGS. 14A-14D; 15A-15C |
| | $7.5 \times 10^{10}$ | red | Yes | cSLO/OCT; IHC | FIGS. 14A-14D; 15A-15C |
| | $7.5 \times 10^{10}$ | red | Yes | cSLO/OCT; IHC | FIGS. 4A-4G |
| *RHO Knockdown and Replacement: single vector strategy in $RHO^{T4R/+}$ mutant eyes (Long-term follow-up after multiple LD exposures)* | | | | | |
| I | $7.5 \times 10^{10}$ | red | Yes | CSLO/OCT; ERG | FIGS. 5A-5D |
| | $7.5 \times 10^{10}$ | red | Yes | cSLO/OCT; ERG | FIGS. 5A-5D |
| | | red | Yes | ERG | FIGS. 5A-5D |
| | | red | Yes | ERG | FIGS. 5A-5D |
| *Natural history in $RHO^{T4R/+}$ mutant eyes (uninjected eyes or pre-injection time points)* | | | | | |
| J | / | red | No | cSLO/OCT | FIGS. 15A-15C |
| | / | white | No | cSLO/OCT | FIGS. 15A-15C |
| | / | white | No | cSLO/OCT | FIGS. 15A-15C |
| | / | white | No | cSLO/OCT | FIGS. 15A-15C |
| | / | white | No | cSLO/OCT | FIGS. 15A-15C |
| | / | white | No | cSLO/OCT | FIGS. 15A-15C |
| | / | white | No | cSLO/OCT | FIGS. 15A-15C |
| | | white | No | cSLO/OCT | FIGS. 15A-15C |

TABLE 1-continued

Summary of the experimental procedures performed in dogs.

WT Control eyes

Figure 15A:
FIGS. 15A-15C show the natural history of disease in RHO mutant (RHO$^{T4R/+}$) dogs housed under different conditions of ambient illumination.
Figure 15B:
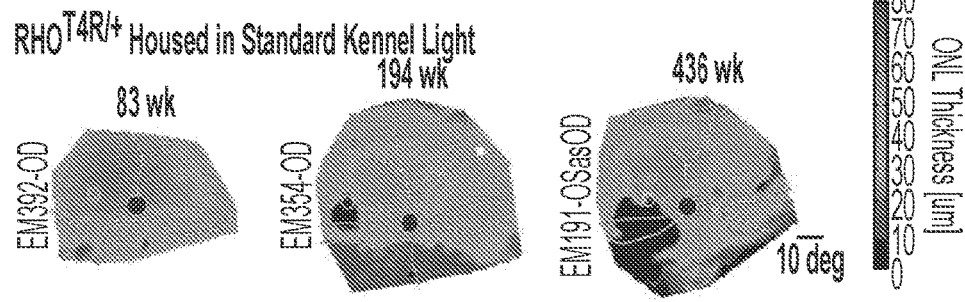
Figure 15C:
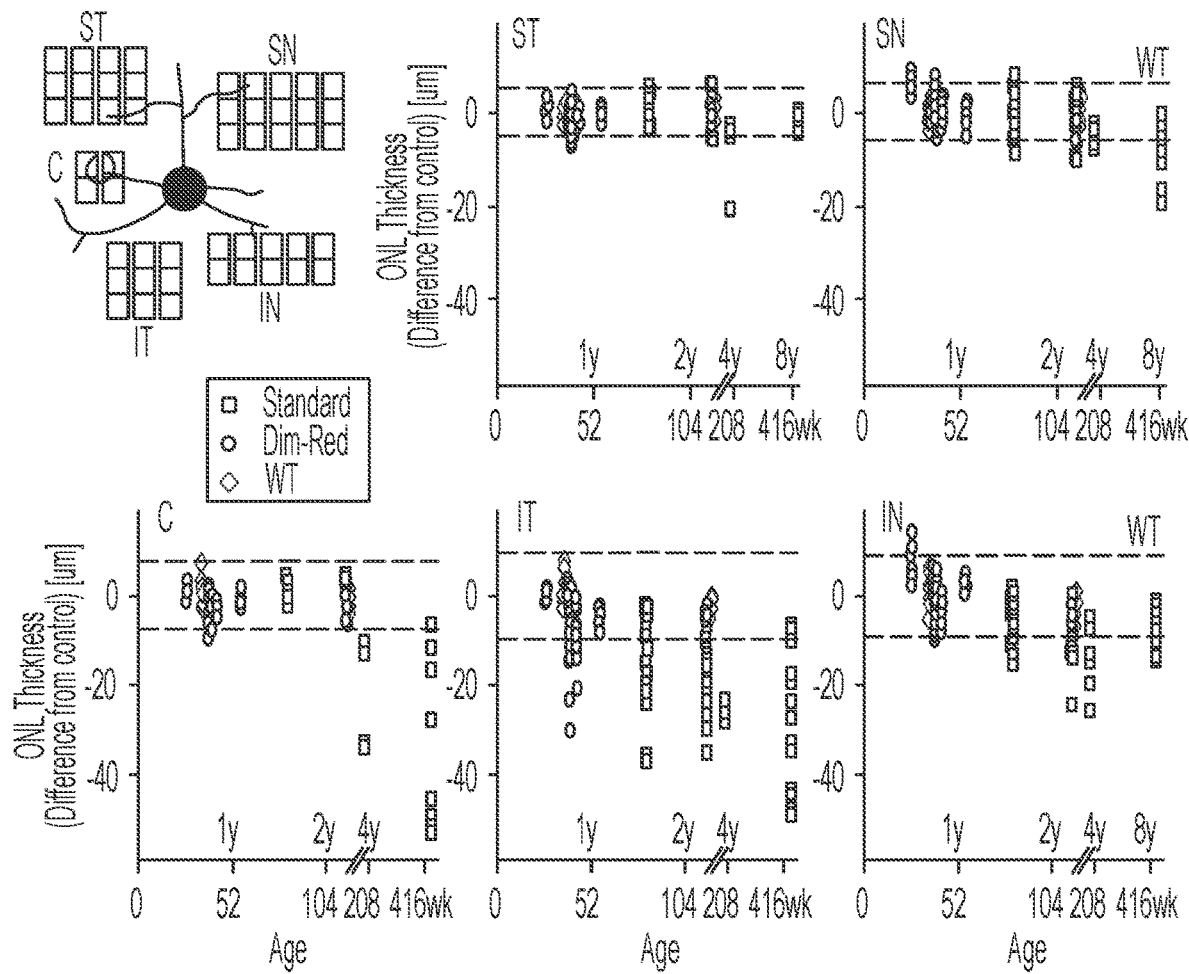
Figure 16A:
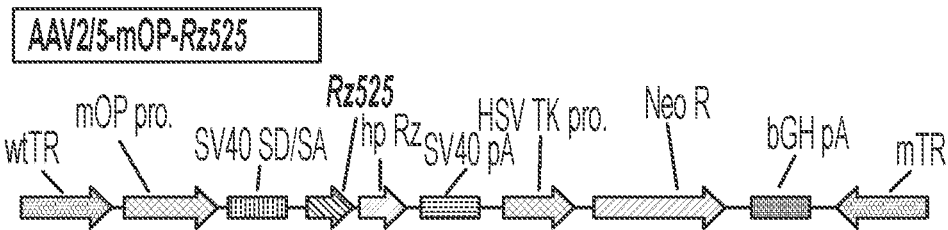
FIGS. 16A-16E show recombinant AAV2/5 vector constructs used in the study.
Figure 16B:
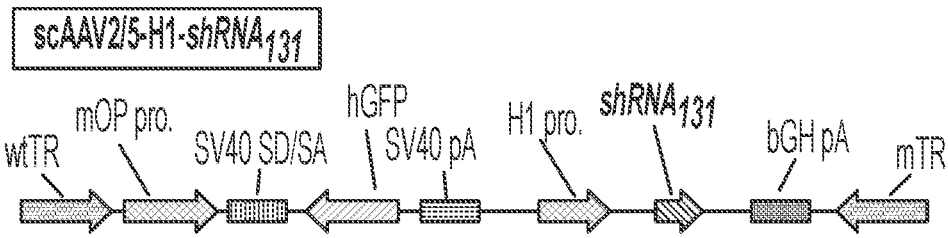
Figure 16C:
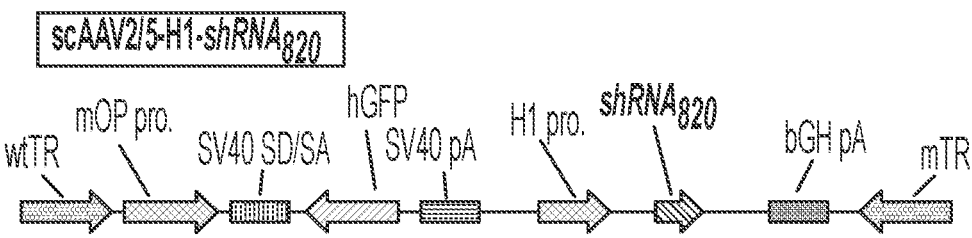
Figure 16D:
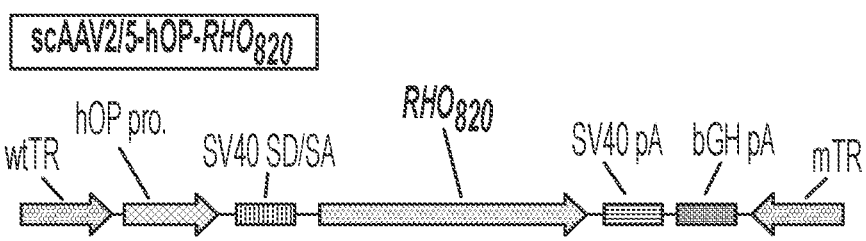
Figure 16E:
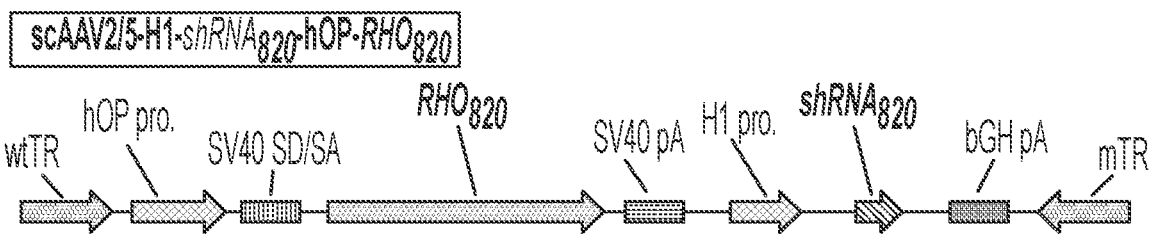

| K | / | white | No | cSLO/OCT | FIGS. 15A-15C |
|---|---|-------|----|----------|---------------|
|   | / | white | No | cSLO/OCT | FIGS. 15A-15C |
|   | / | white | No | cSLO/OCT | FIGS. 15A-15C |
|   | / | white | No | cSLO/OCT | FIGS. 15A-15C |
|   | / | white | No | cSLO/OCT | FIGS. 15A-15C |
|   | / | white | No | cSLO/OCT | FIGS. 15A-15C |

Lights: cyclic environmental (12 hours ON, 12 hours OFF) dim red or white illumination; LE: light exposure protocol; OD: right eye; OS: left eye; F: female; M: male; IVit: intravitreal; subRPE: under the retinal pigment epithelium; cSLO: confocal scanning laser ophthalmoscopy; OCT: optical coherence tomography; RNA/Protein: Quantification of rhodopsin RNA and protein levels; ERG: electroretinography; H&E: histology with hematoxylin & eosin staining; IHC: immunohistochemistry.

Suppression of mutant RHO with shRNA$_{820}$

Figure 3A:
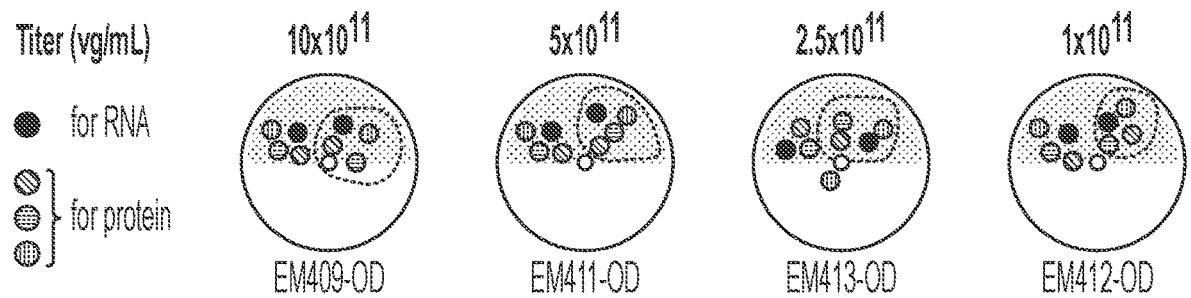
FIGS. 3A-3D show suppression of rhodopsin with shRNA$_{820}$ in RHO-mutant retinas.
Figure 3B:
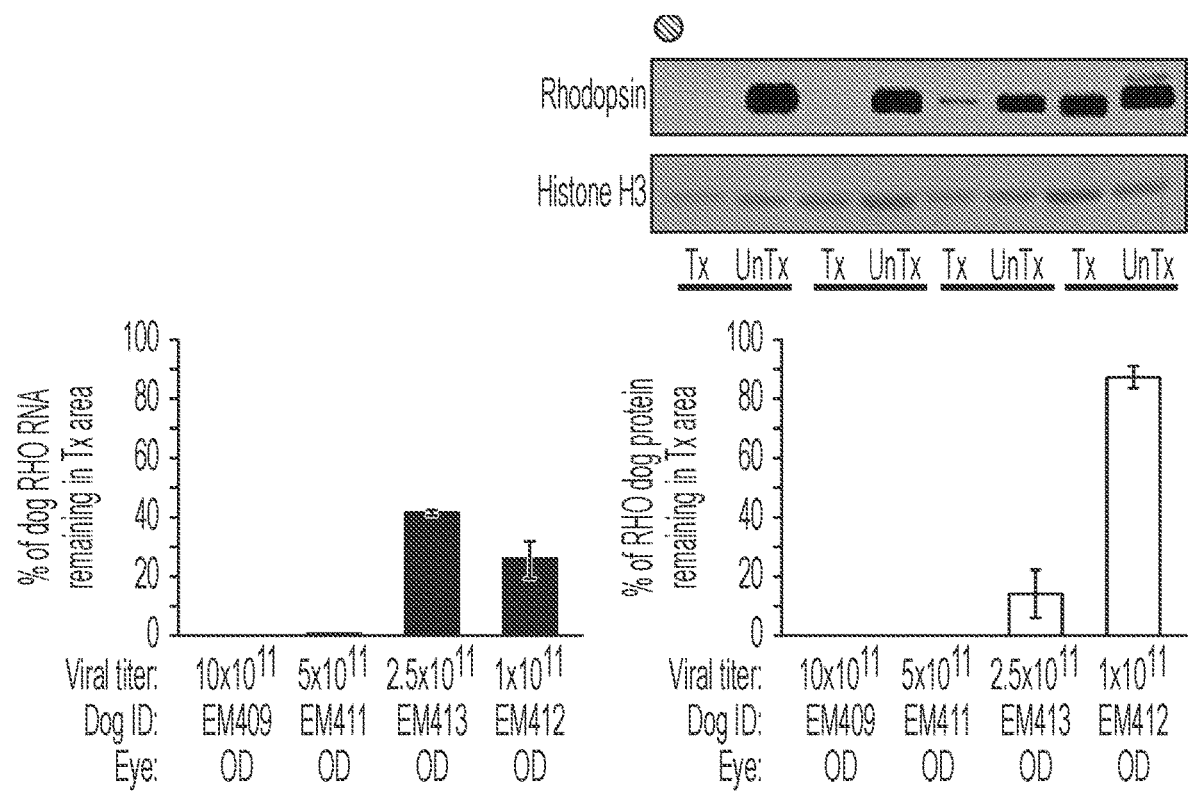

To verify the efficiency of shRNA$_{820}$ in heterozygous mutant retinas that express both WT and mutant RHO alleles, subretinal injections of AAV-shRNA820 were performed over a range of titers ($1 \times 10^{11}$ to $10 \times 10^{11}$ vg/mL) in ten RHO-mutant eyes that were followed for 8 to 10 weeks post-injection (Table 1, groups D, E) Since the RHO-mutant dog retinas are highly sensitive to light (45-48), the animals were housed under dim red light from birth until the end of the study, and the surgical intervention was performed under infrared illumination (49). Four eyes were used for quantification of RHO knockdown efficiency at the RNA and protein levels (FIG. 3A; Table 1, group D). As in the WT animals, at a titer of $10 \times 10^{11}$ vg/mL there was complete silencing of RHO RNA and protein expression in the treated area (FIG. 3B). A similar absence of RHO expression was achieved with the lower ($5 \times 10^{11}$ vg/mL) titer. However, interpretation of this result was confounded by OCT imaging revealing partial loss of ONL thickness restricted to the treated area in this eye. Persistent expression of RHO was seen with the lower ($1 \times 10^{11}$ and $2.5 \times 10^{11}$ vg/mL) titers.

Figure 3C:
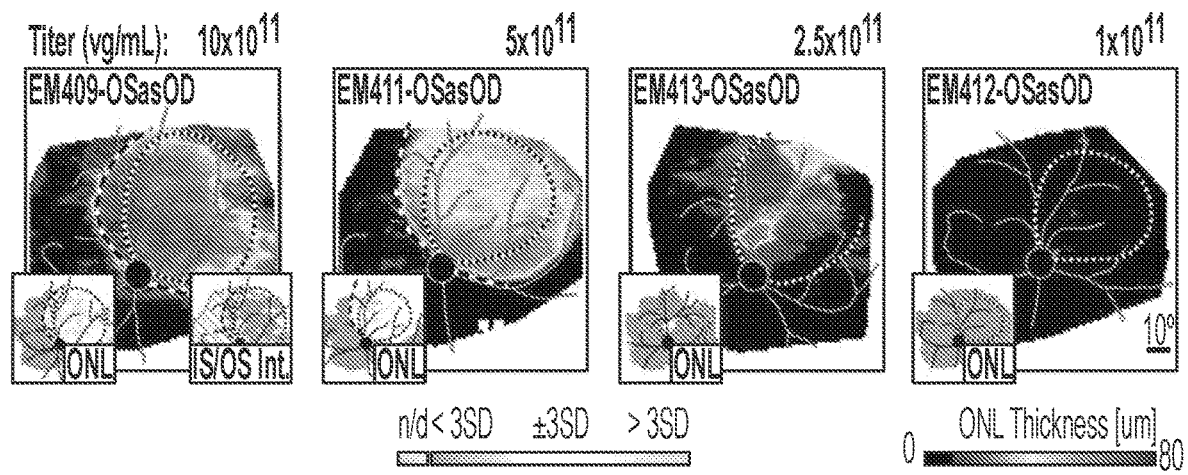

Next, it was evaluated whether knockdown alone could arrest photoreceptor degeneration. Another set of four RHO-mutant eyes (Table 1, group E) were also injected with the same range of titers of AAV-shRNA$_{820}$ but at 6 to 8 weeks post-injection they were exposed for one minute to a moderate intensity white light known to cause acute retinal degeneration in this canine model (46-48). Two weeks after light exposure, the eye injected with the titers of $10 \times 10^{11}$ and $5 \times 10^{11}$ vg/mL showed a distinct region of ONL retention corresponding to the treatment area (FIG. 3C). Outside the treatment area, there was severe retinal degeneration demonstrating the substantial rescue of photoreceptors achieved by knockdown alone. There were abnormalities with IS/OS intensity expected from knockdown of RHO. Also, the eye injected with the highest ($10 \times 10^{11}$ vg/mL) titer showed some ONL thickening implying mild photoreceptor stress. Eyes injected with the two lowest titers ($2.5 \times 10^{11}$ vg/mL and $1 \times 10^{11}$ vg/mL) had limited to no ONL retention in the treated area (FIG. 3C). Histological analysis of these eyes (FIG. 3D) confirmed the results of in vivo retinal imaging. There was ONL retention with shortened inner segments, loss of outer segment structure, and reduction in rod opsin immunolabeling following injection with the two highest titers. With the $2.5 \times 10^{11}$ vg/mL titer severe ONL thinning was found within the treated area with the exception of a small island of ONL retention. The lowest ($1 \times 10^{11}$ vg/mL) titer did not confer any protection against light exposure. In this eye, the ONL in the treated area resembled that of the untreated region; it was limited to a single row of cone somata with rare residual rod somata and rod opsin-positive debris.

Taken together these findings confirm that shRNA$_{820}$ can suppress both WT and T4R alleles in vivo, and AAV2/5-shRNA$_{820}$ titers in the $5 \times 10^{11}$ to $10 \times 10^{11}$ vg/mL range confer protection of photoreceptor cells (but not their outer segments) from retinal degeneration in RHO-mutant retinas. This partial protective effect likely results from efficient RHO suppression which leads to deconstruction of rod outer segments while keeping the inner segments and rod photoreceptor cell bodies intact. The need to protect the retina from mutant-RHO driven degeneration, while retaining functional rods that have preserved light-sensing outer segments, led to exploring whether the suppression of endogenous canine RHO (WT and mutant) could be supplemented with the expression a human RHO cDNA (RHO$_{820}$) made resistant to shRHA$_{820}$.

Combined Suppression and Replacement

Dual Vector-Dual Function Strategy

Figure 13A:
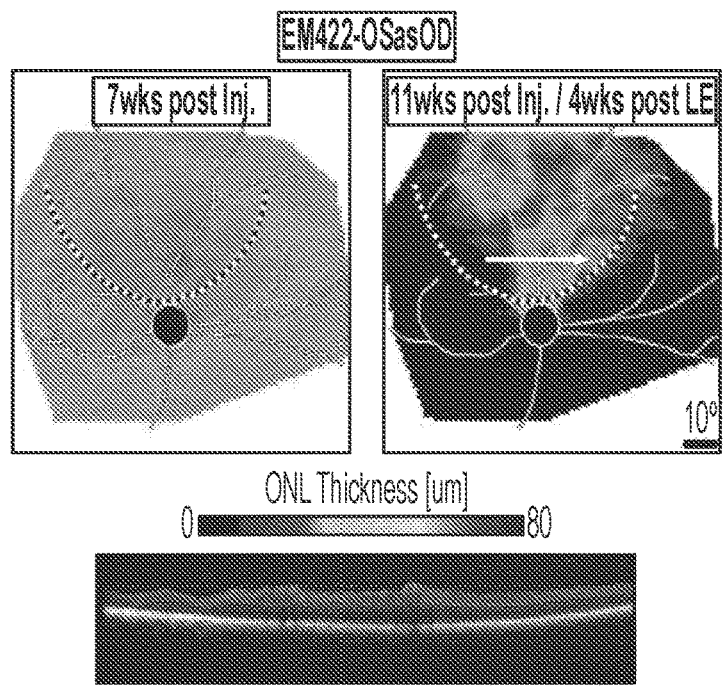
Figure 13B:
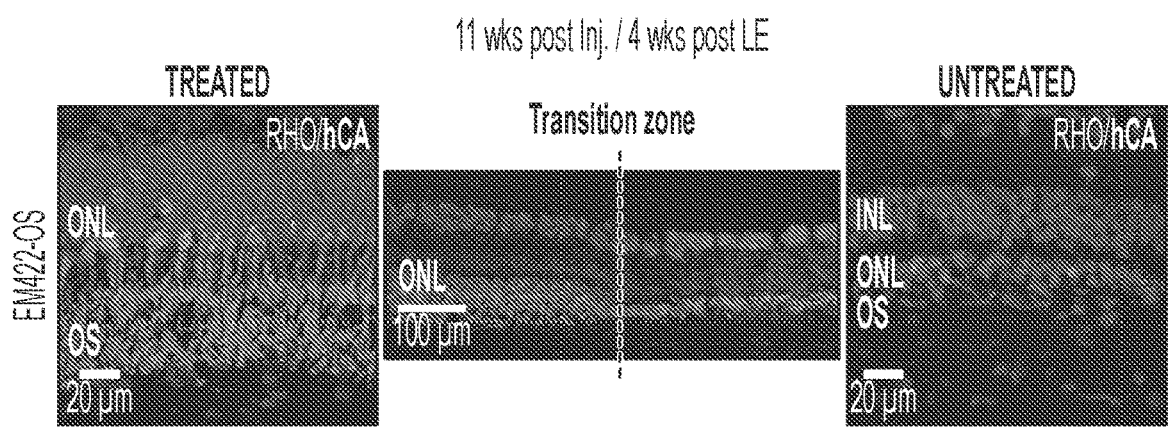
Figure 13C:
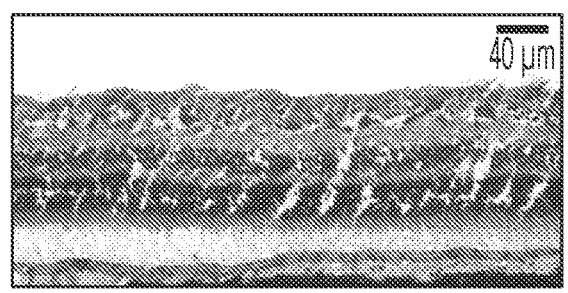
Figure 13D:
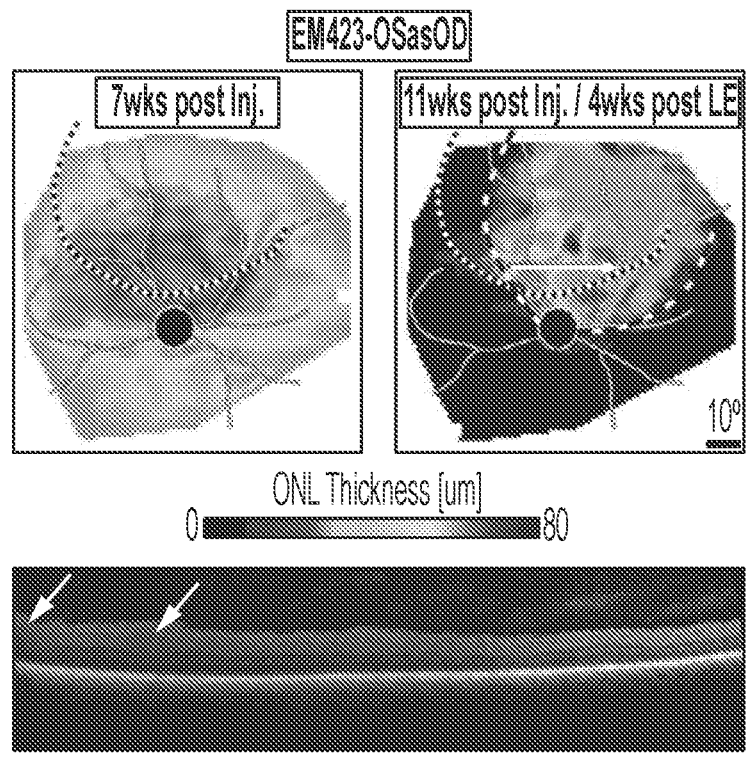
Figure 13E:
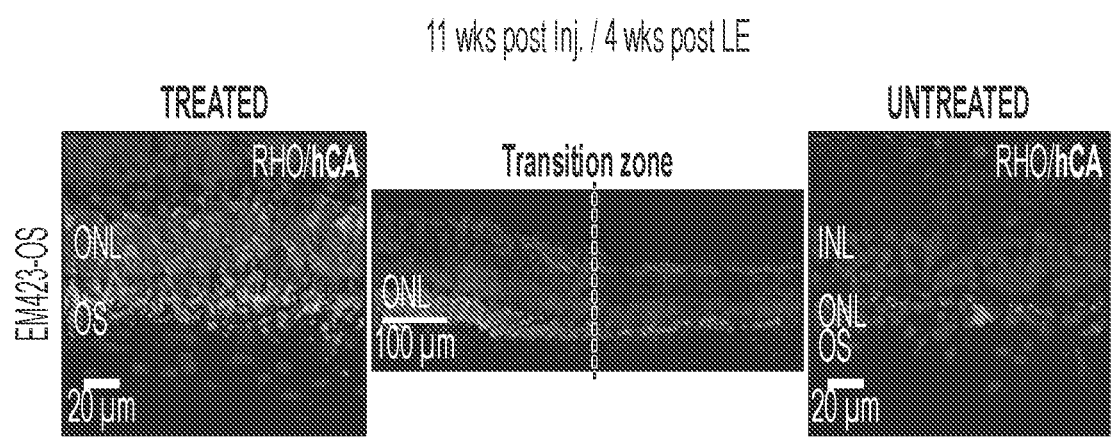

Initially, a two-vector strategy was tested by co-injecting the AAV-shRNA$_{820}$ used above with a similar AAV2/5 serotype carrying the resistant human RHO cDNA (RHO$_{820}$) under the control of the human opsin promoter (AAV-RHO$_{820}$). Two RHO-mutant eyes were co-injected with a similar titer ($5 \times 10^{11}$ vg/mL) of both vectors (Treatment 1:1), and two other mutant eyes were co-injected with AAV-shRNA$_{820}$ at $5 \times 10^{11}$ vg/mL and AAV-RHO$_{820}$ at $10 \times 10^{11}$ vg/mL (Treatment 1:2) (Table 1, group G). One eye from each treatment group was exposed at 7 weeks post-injection to the light exposure protocol, and all four eyes were imaged 4 weeks later by OCT. In the light exposed eye receiving Treatment 1:1, there was some ONL retention, but it did not reach normal thickness in most of the treated area (FIG. 13A). In the region with the greatest ONL retention, there was some rod outer segment preservation suggesting a beneficial outcome conferred by replacement with RHO$_{820}$ (FIGS. 13B, 13C). Partial ONL protection also occurred in the light exposed eye that had received Treatment 1:2; however, abnormally increased thickness of the inner retina was seen in the treated region (FIG. 13D) resulting from severe perivascular and inner retinal infiltration of mononuclear inflammatory cells (FIG. 13F). In addition, rod outer segment disruption was present (FIG. 13E). Similar findings were observed by OCT in the contralateral shielded eye (Treatment 1:2), that included focal retinal detachment, and signs of perivascular, and subretinal cellular infiltration (FIG. 13G). The results of this two-vector strategy pointed towards a beneficial effect of the combination of knockdown and replacement function. Nevertheless, there was incomplete rod protection, and treatment resulted in severe retinal complications. To circumvent these limitations, a single AAV vector was developed that combined the knockdown (shRNA$_{820}$) and resistant replacement (RHO$_{820}$) elements. It was hypothesized that this alternative strategy would ensure co-transduction of photoreceptors at a lower viral load, and thus achieve better protection from retinal degeneration and improved safety.

Single Vector-Dual Function Strategy

Figure 4A:
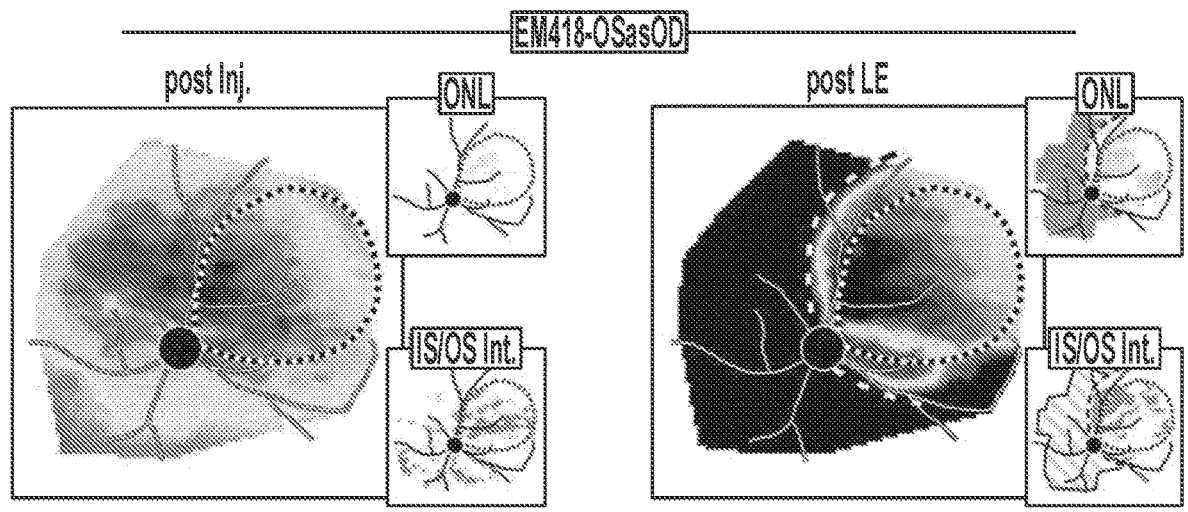
FIGS. 4A-4G show suppression and replacement of rhodopsin with single vector prevents retinal degeneration in RHO-mutant retinas.
Figure 4B:
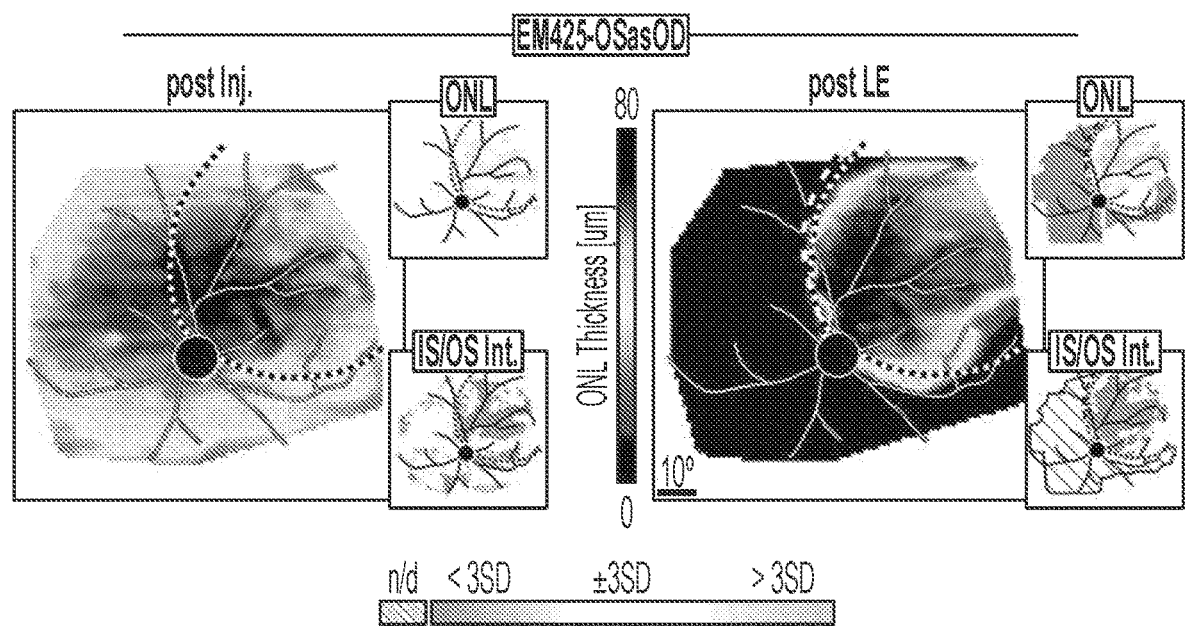
Figure 4C:
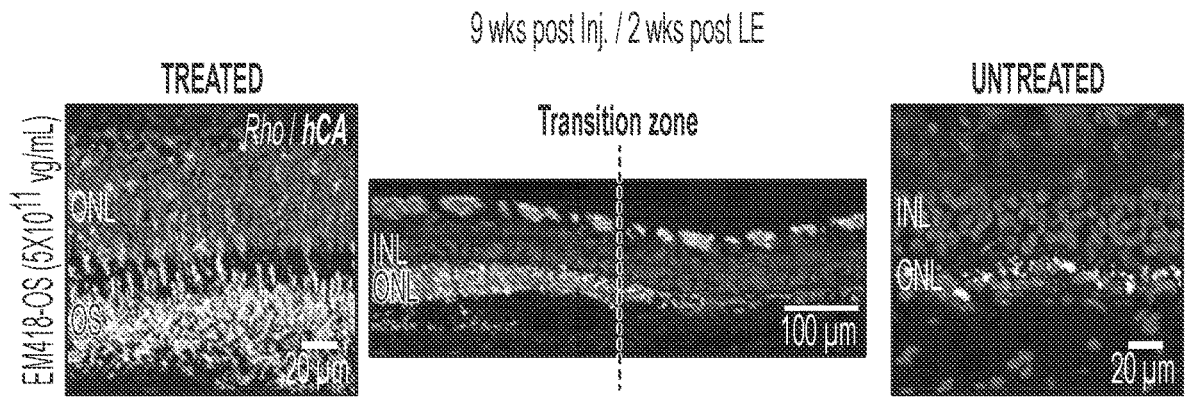
Figure 4D:
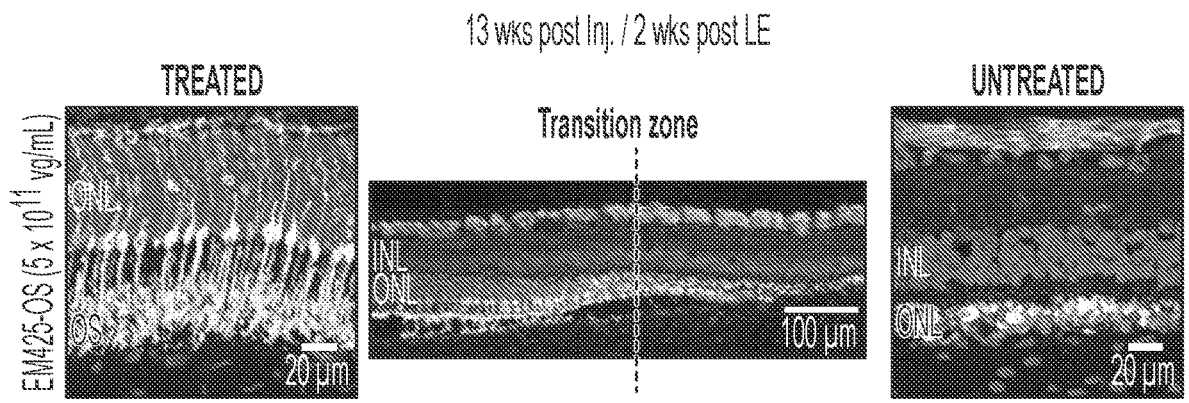
Figure 4E:
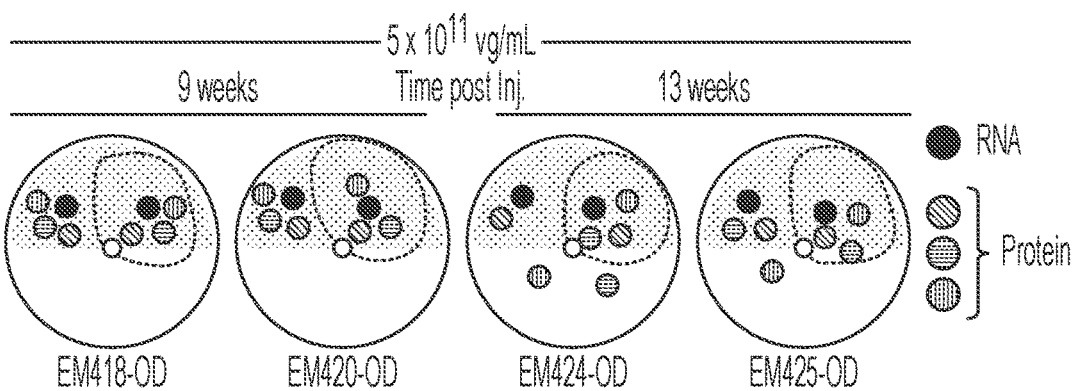
Figure 14A:
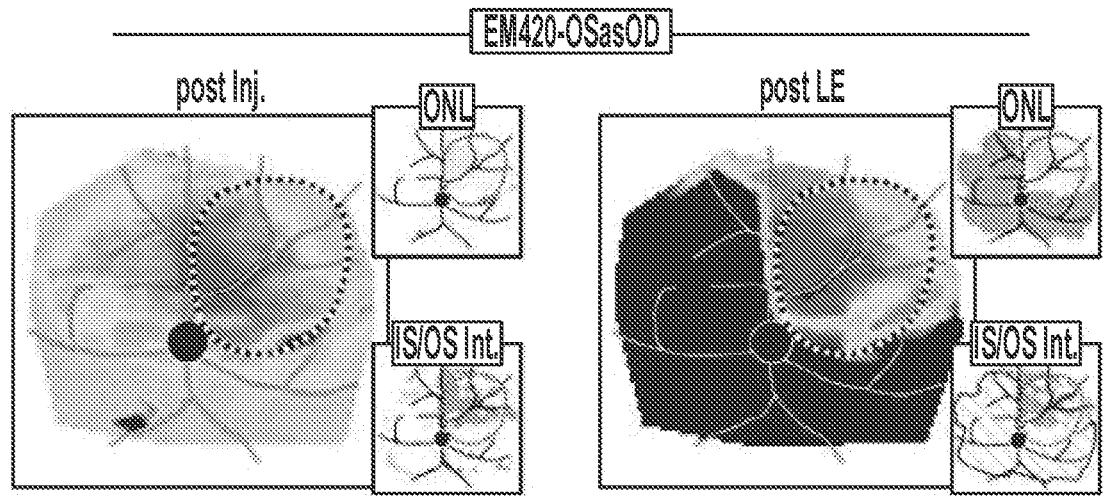
FIGS. 14A-14D show suppression and replacement of rhodopsin with single vector prevents retinal degeneration in RHO mutant retinas (additional data to FIGS. 4A-4H).
Figure 14B:
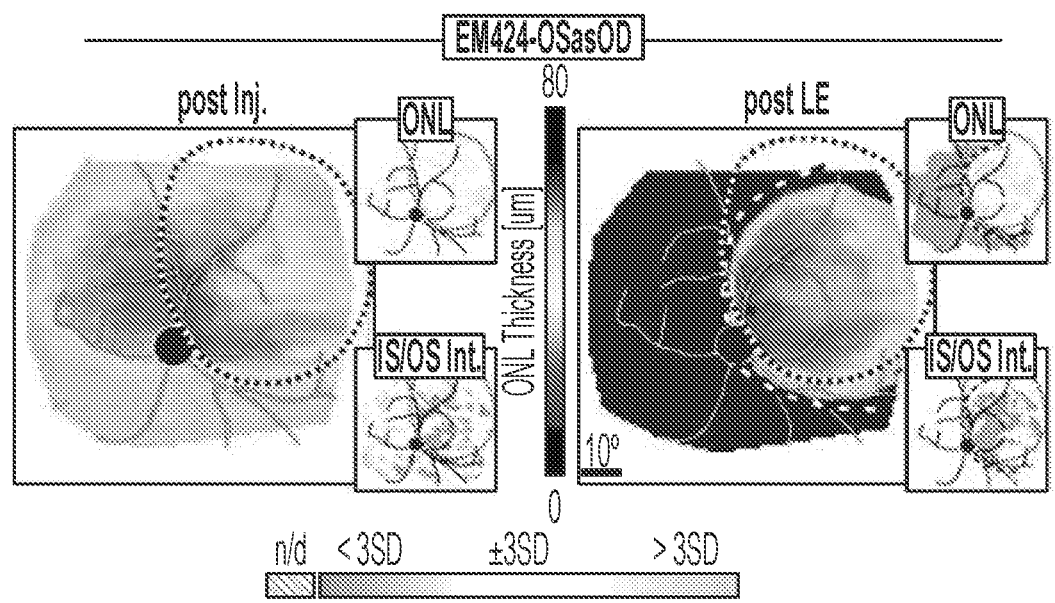
Figure 14C:
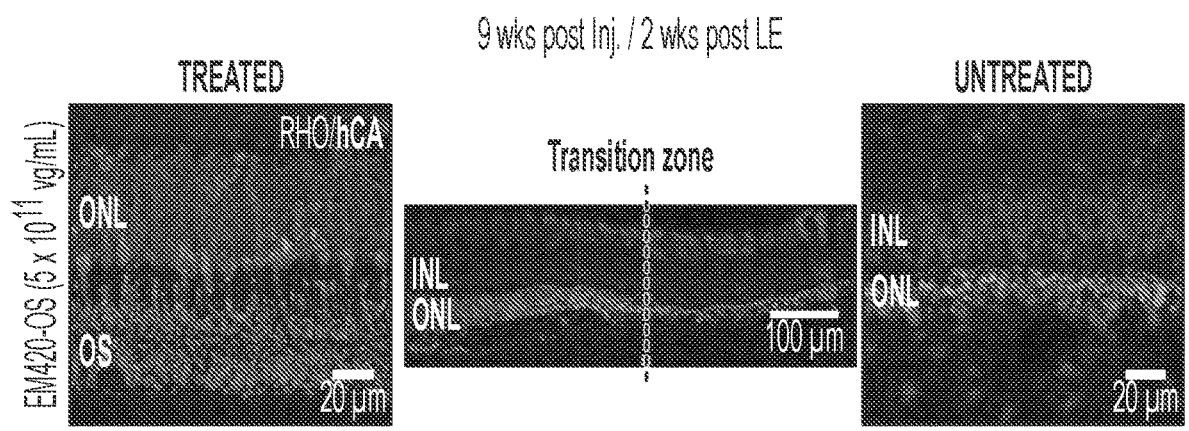
Figure 14D:
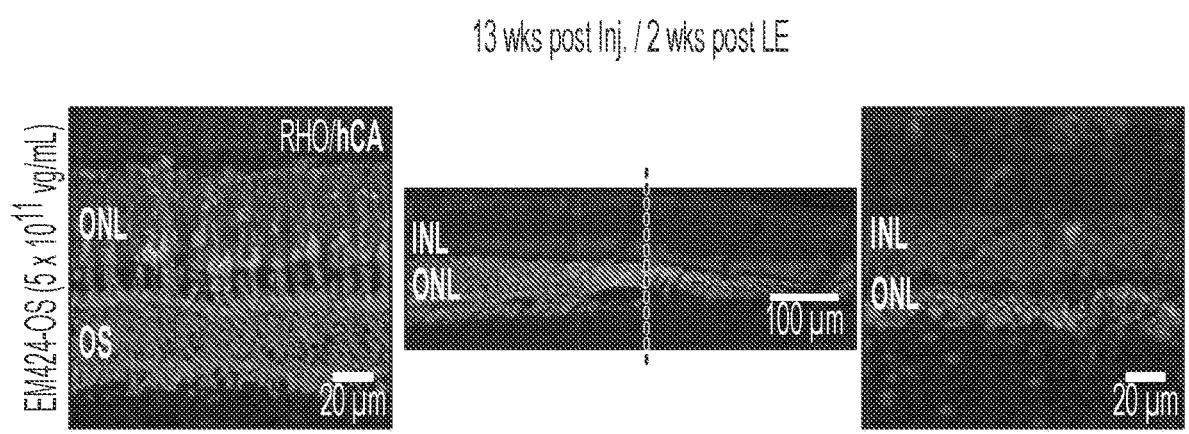

Subretinal injections of AAV-shRNA$_{820}$-RHO$_{820}$ were performed in eight RHO-mutant eyes at the previously determined optimal titer of $5 \times 10^{11}$ vg/mL (Table 1, group H). Treated animals were subjected to the light exposure protocol at 7 weeks (n=2 eyes) or at 13 weeks (n=2 eyes) post-injection to determine the efficacy of the single vector approach in preventing acute retinal degeneration. In all four eyes there was substantial retention of ONL thickness 2 weeks after light exposure (FIGS. 4A, 4B; FIGS. 14A, 14B). Most significantly, all four eyes had in the treated area a detectable IS/OS signal. Structural analysis of photoreceptors by IHC (FIGS. 4C, 4D; FIGS. 14C, 14D) confirmed the in vivo results: in treated areas a normal number of photoreceptor cell bodies was retained in the ONL, and rod outer segments were detected. Preservation of elongated rod outer segments was associated with improved morphology of cone inner and outer segments. Four contralateral eyes that had been injected with a similar dose of AAV-shRNA$_{820}$-RHO$_{820}$ but not light exposed were collected at similar time-points (9 and 13 weeks post-injection), and processed for RHO RNA and protein quantification in treated and untreated areas (FIG. 4E). As anticipated, canine RHO RNA (FIG. 4F) at 9 weeks post-injection was considerably reduced in the treated areas (15-16% of that found in untreated areas) of the two eyes. In the two eyes that were processed at 13 weeks post-injection, the levels of remaining canine RHO RNA were further reduced (1-2% of untreated areas). The human RHO$_{820}$ transgene transcript levels (FIG. 4G) in the two eyes collected at 9 weeks post-injection were at 5-9% of canine RHO levels measured in untreated areas. At a later time point, 13 weeks post-injection, the levels of human RHO$_{820}$ RNA were considerably higher (118% to 132% of canine RHO levels measured in untreated areas). At the protein level (FIG. 4G), measurements of total (endogenous canine and human) RHO protein showed a similar temporal trend, with higher RHO protein levels (31-33% of canine RHO levels in untreated areas) at 13 weeks than at 9 weeks post-injection (18-19%). Taken together, these results confirm that a single viral vector that combines both a RHO knockdown and RHO replacement function can effectively preserve the integrity of the entire structure of the rod photoreceptors including their inner and outer segments, and that the levels of expression of the resistant RHO transgene continue to rise several weeks after delivery of the vector.

Figure 5A:
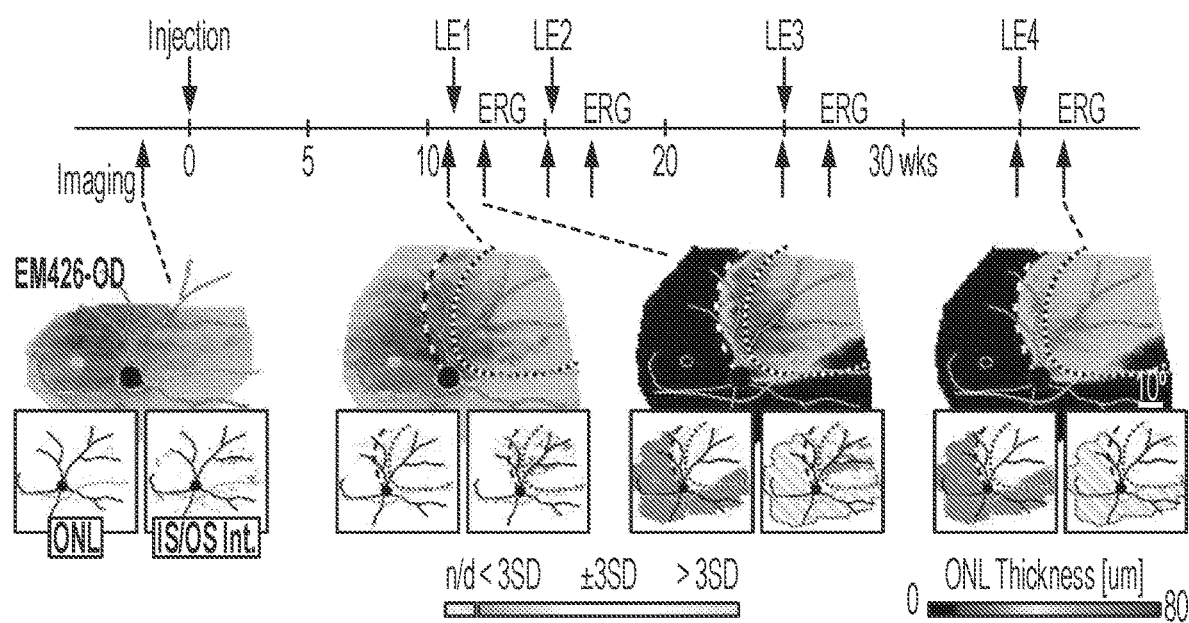
FIGS. 5A-5D show protection of retinal structure and function in RHO-mutant retinas treated with single vector that combines suppression and replacement of rhodopsin of up to 5 weeks.
Figure 5B:
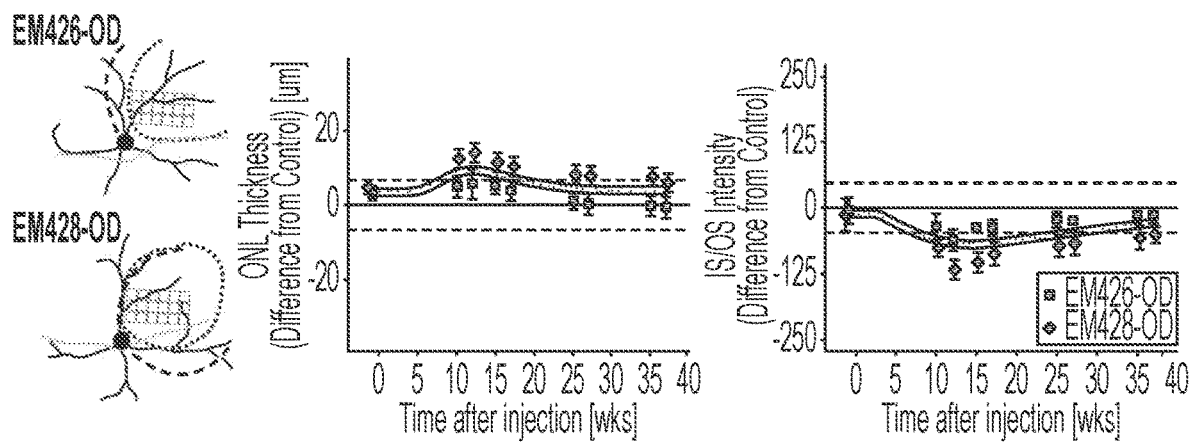

Thirty-Seven Week Preservation of Retinal Structure and Function with Single Vector Treatment To assess the long-term stability of the single vector strategy and its ability to protect RHO-mutant eyes from degeneration, two RHO-mutant dogs were subretinally injected in one eye with AAV-shRNA$_{820}$-RHO$_{820}$ at the previously determined optimal titer of $5 \times 10^{11}$ vg/mL, while the contralateral eyes received a similar volume of balanced salt solution (BSS) (Table 1, group I). All four eyes were repeatedly light exposed at 11, 15, 25 and 35 weeks post-injection. OCT imaging was performed pre-injection, as well as immediately prior, and ~2 weeks after each light exposure (FIG. 5A, upper row, timeline). After the first light exposure, there was complete preservation of photoreceptors within the treated area and this dramatic treatment effect persisted for 37 weeks post injection even after three additional light exposures (FIG. 5A, lower rows). Quantitative analysis performed in sampled retinal locations (FIG. 5B, left) from the treated area of the two AAV-shRNA$_{820}$-RHO$_{820}$ injected eyes showed a small increase in ONL thickness after injection that peaked near 12 weeks before gradually returning to normal levels by 37 weeks (FIG. 5B, middle). IS/OS signal remained detectable at all time-points within the treated areas. There was, a slight decrease in IS/OS intensity that also peaked near 12 weeks followed by a gradual return to normal levels by 37 weeks post injection (FIG. 5B, right).

Figure 5C:
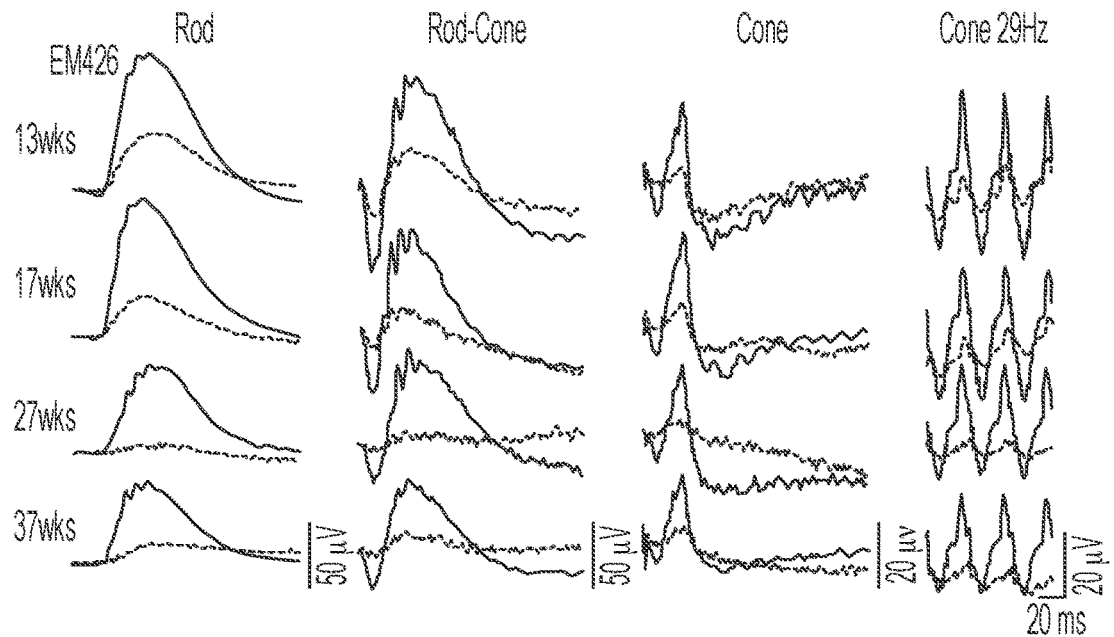
Figure 5D:
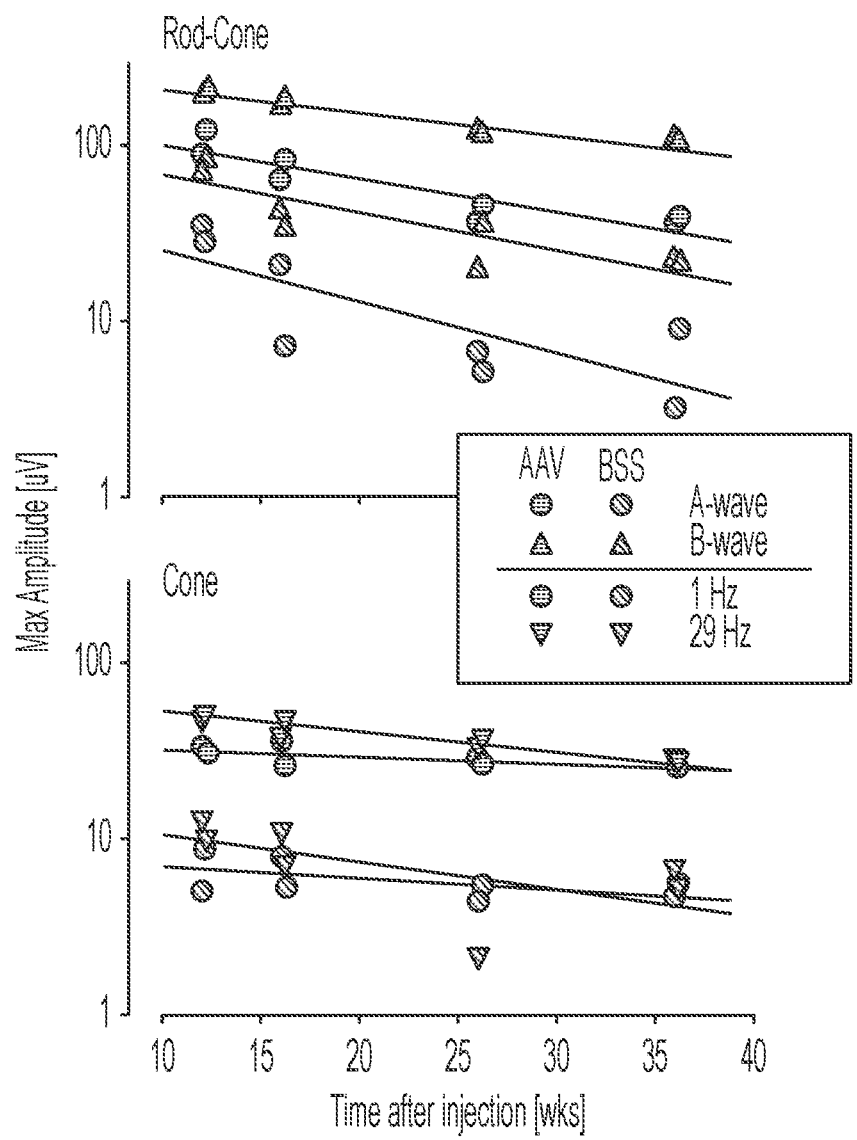

Electroretinography (ERG) measurements were performed 2.1-2.4 weeks after each light exposure to assess retinal function (FIG. 5A, upper row, timeline). Qualitatively, ERGs showed consistently better rod- and cone-mediated function in the AAV-shRNA$_{820}$-RHO$_{820}$ treated eye FIG. 5C, solid line traces) versus the contralateral BSS-injected eye (FIG. 5C, dashed line traces) of a RHO-mutant dog; substantial ERG asymmetry was present between vector and BSS-treated eyes, and the asymmetry increased after each light exposure (FIG. 5C). Quantitatively, amplitudes of rod-dominated ERG traces showed a tendency to decrease over time in both the AAV and BSS injected eyes, likely due to continued photoreceptor degeneration occurring in the peripheral retina outside treatment areas (FIG. 5D, upper panel). Cone function appeared overall to be more stable throughout the 37 week post-injection period with four intervening light exposures (FIG. 5D, lower panel). Importantly, at each time point, there were substantially greater rod and cone responses in treated eyes.

These results demonstrate that AAV-shRNA$_{820}$-RHO$_{820}$ preserves the integrity of the entire structure of rod photoreceptors, and confers protection of up to 37 weeks of retinal structure and function from the degeneration that otherwise rapidly occurs in untreated RHO-mutant eyes.

Suppression of Canine RHO with Rz525

Figure 9A:
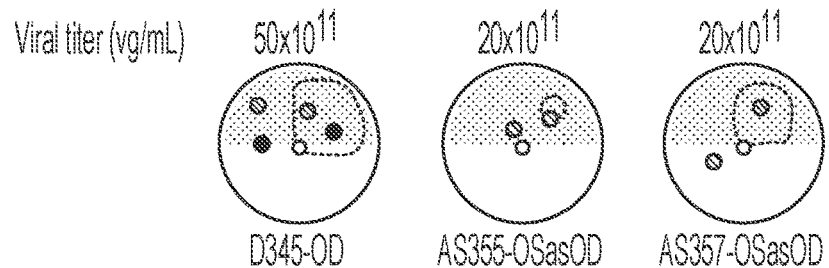
FIGS. 9A-9C show the suppression of RHO expression with Rz525 in WT canine retinas.
Figure 9B:
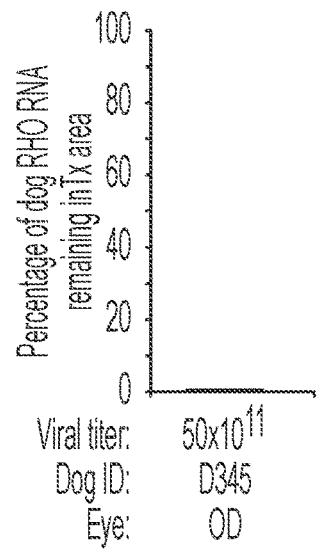
Figure 9C:
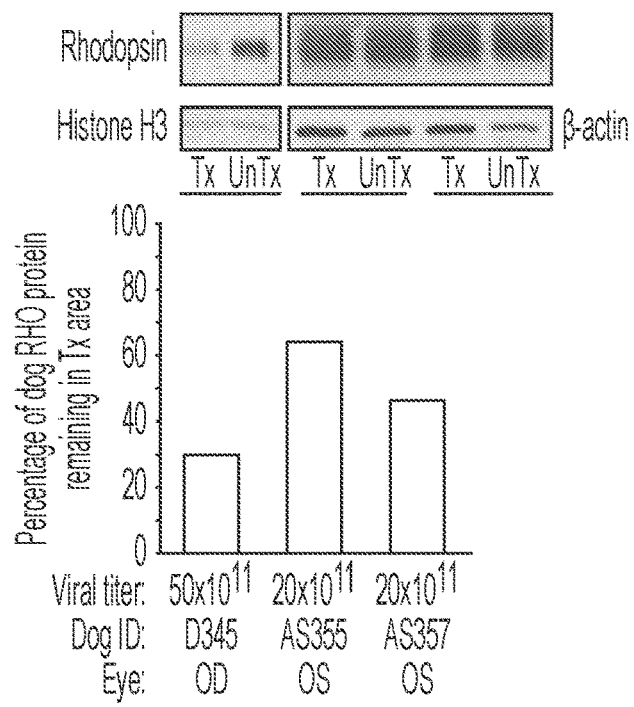

A hammerhead ribozyme (Rz525) that was shown in an in vitro assay (FIG. 8) to reduce the expression of WT human RHO, was packaged in an AAV2/5 vector and subretinally injected in three WT canine eyes at 20 and $50 \times 10^{11}$ vg/mL titers (FIG. 9A). The efficiency of AAV2/5-Rz525 at reducing expression of endogenous canine RHO at the RNA level was measured only in the eye injected with the highest titer ($50 \times 10^{11}$ vg/mL). In the treated area there was complete silencing of RHO expression at the RNA level (FIG. 9B) while RHO protein levels were reduced to ~30% (FIG. 9C). The two eyes injected with a $20 \times 10^{11}$ vg/ml had higher (47 and 64%) levels of endogenous canine RHO protein remaining in the treated areas (FIG. 9C).

Figure 10D:
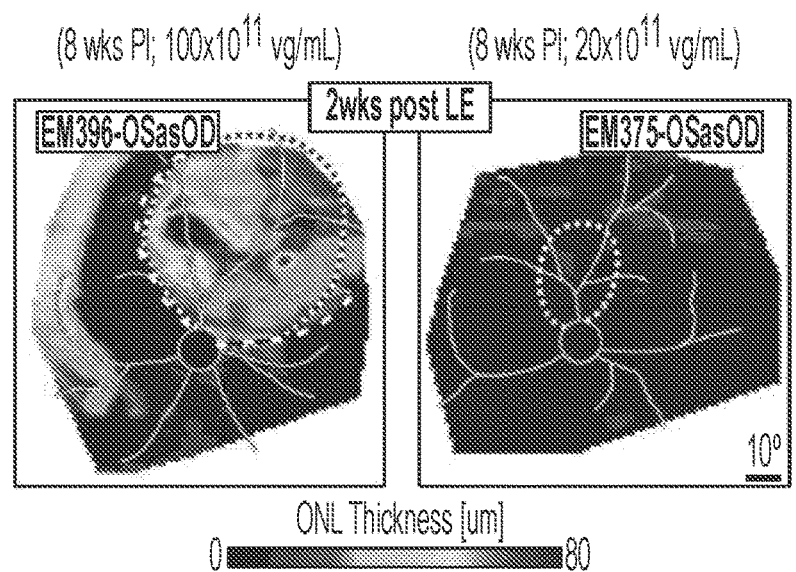
Figure 10E:
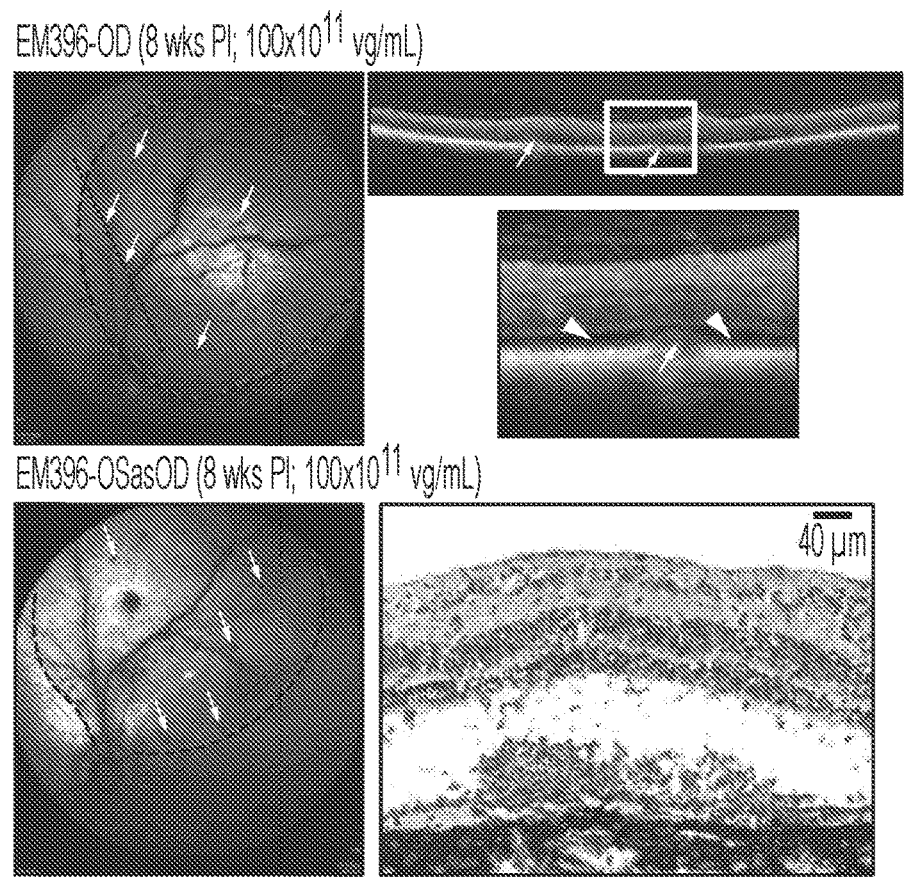

Rz525 was subsequently tested in five heterozygous RHO-mutant eyes (Table 1, group F) that were subretinally-injected with AAV2/5-Rz525 at either $20 \times 10^{11}$ (3 eyes) or $100 \times 10^{11}$ vg/mL (2 eyes). An additional mutant eye was injected with BSS and served as a negative control. At 8 weeks post injection, prominent silencing of RHO expression was seen with the highest titer ($100 \times 10^{11}$ vg/mL) both at RNA (13% remaining) and protein (0.1% remaining) levels in the treated area of EM396-OD (FIGS. 10A-10C). However, this treatment was associated with signs of retinal detachment and cellular infiltration in the subretinal space detected by OCT imaging (FIG. 10E, upper row), and confirmed by histology in the fellow eye (EM396-OS) injected with a similar titer (FIG. 10E, lower row). Two eyes injected with the lower $20 \times 10^{11}$ vg/mL titer had more endogenous canine RHO remaining within the treated area both at the RNA (39 and 66%) and protein (36 and 67%) levels (FIGS. 10A-10C). To evaluate whether these levels of RHO suppression were sufficient to confer protection from light-induced retinal degeneration, two mutant-RHO eyes injected with AAV2/5-Rz525 at 20 and 100×10$^{11}$ vg/mL were exposed to light at 6 weeks post-injection and imaged by OCT. Two weeks after the light exposure, the eye injected with a titer of 100×10$^{11}$ vg/mL had some regions of ONL retention within the treated area; however, no such recue was seen in the eye injected with the lower (20×10$^{11}$ vg/mL) titer (FIG. 10D).

These results showed that near complete knockdown of RHO could be achieved with Rz525, and that reduction of RHO protein expression was associated with some degree of protection against light-induced retinal degeneration in the canine model of RHO-adRP. Yet, protection could be achieved only when injecting high viral loads that were associated with severe signs of retinitis/chorioretinitis.

TABLE 2

Condon frequency (per thousand) at target site of WT RHO and at condon-modified resistant site of hRHO820 (based on Codon Usage Database, kazusa.or.jp/codon/).

| Species | WT RHO | Resistant hRHO$_{820}$ |
|---|---|---|
| | GCA | GCU |
| Dog | 13.7 | 17.2 |
| Human | 15.8 | 18.4 |
| | UUC | UUU |
| Dog | 17.1 | 24.4 |
| Human | 17.6 | 20.3 |
| | UAC | UAU |
| Dog | 17.5 | 11.5 |
| Human | 15.3 | 12.2 |
| | AUC | AUA |
| Dog | 25.7 | 7.2 |
| Human | 20.8 | 7.5 |
| | GCA + UUC + UAC + AUC | GCU + UUU + UAU + AUA |
| Dog | 74 | 60.3 |
| Human | 69.5 | 58.4 |

Limited Suppression of WT Canine RHO with shRNA$_{131}$

A knockdown reagent (shRNA$_{131}$) that had been shown to reduce expression of WT human RHO in cell culture (FIGS. 1A-1H) was packaged in an AAV2/5 vector and subretinally injected in two WT canine eyes at 10 and 50×10$^{11}$ vg/mL titers (FIG. 11A; Table 1, group B). The efficiency of AAV2/5-shRNA$_{131}$ at reducing expression of endogenous canine RHO both at the RNA and protein level was limited. Even with the highest titer (50×10$^{11}$ vg/mL) there was still 50% of normal levels of endogenous canine RHO RNA (FIG. 11B) and 70% of endogenous canine RHO protein (FIG. 11C) remaining within the treated areas 8 weeks post-injection. As a result, further investigations in dogs on the use of shRNA$_{131}$ as a potential candidate for RHO suppression were not pursued.

Figure 17:
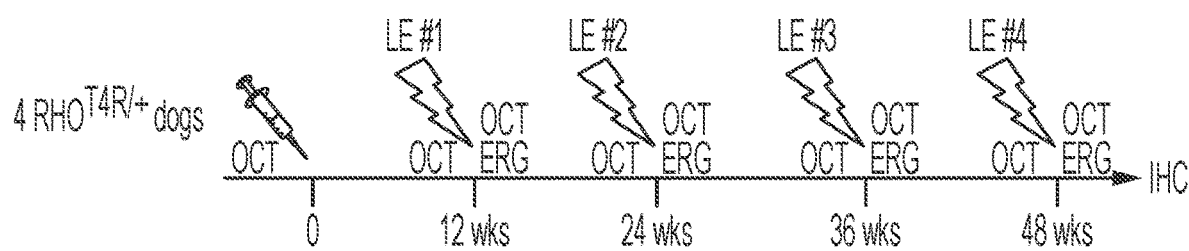
FIG. 17 is an illustration of the experimental design of the long-term study of the AAV therapy in dogs. The ability of scAAV2/5-hOP-RHO820-H1-shRNA820 to confer stable structural (assessed by OCT and IHC) and functional (assessed by ERG) protection of photoreceptors against repeated LE events that cause acute retinal degeneration in untreated RHO$^{T4R/+}$ dog retinas, in four RHO-mutant dogs was evaluated. Each dog had its right eye (OD) subretinally-injected with 150 μL of the AAV construct at a titer of 5×10$^{11}$ vg/mL, while the contralateral left eye (OS) was subretinally-injected with a similar volume of balanced salt solution (BSS). PI: Post-Injection; LE: Light Exposure; OCT: Optical Coherence Tomography; ERG: Electroretinography; IHC: Immunohistochemistry.
Figure 18A:
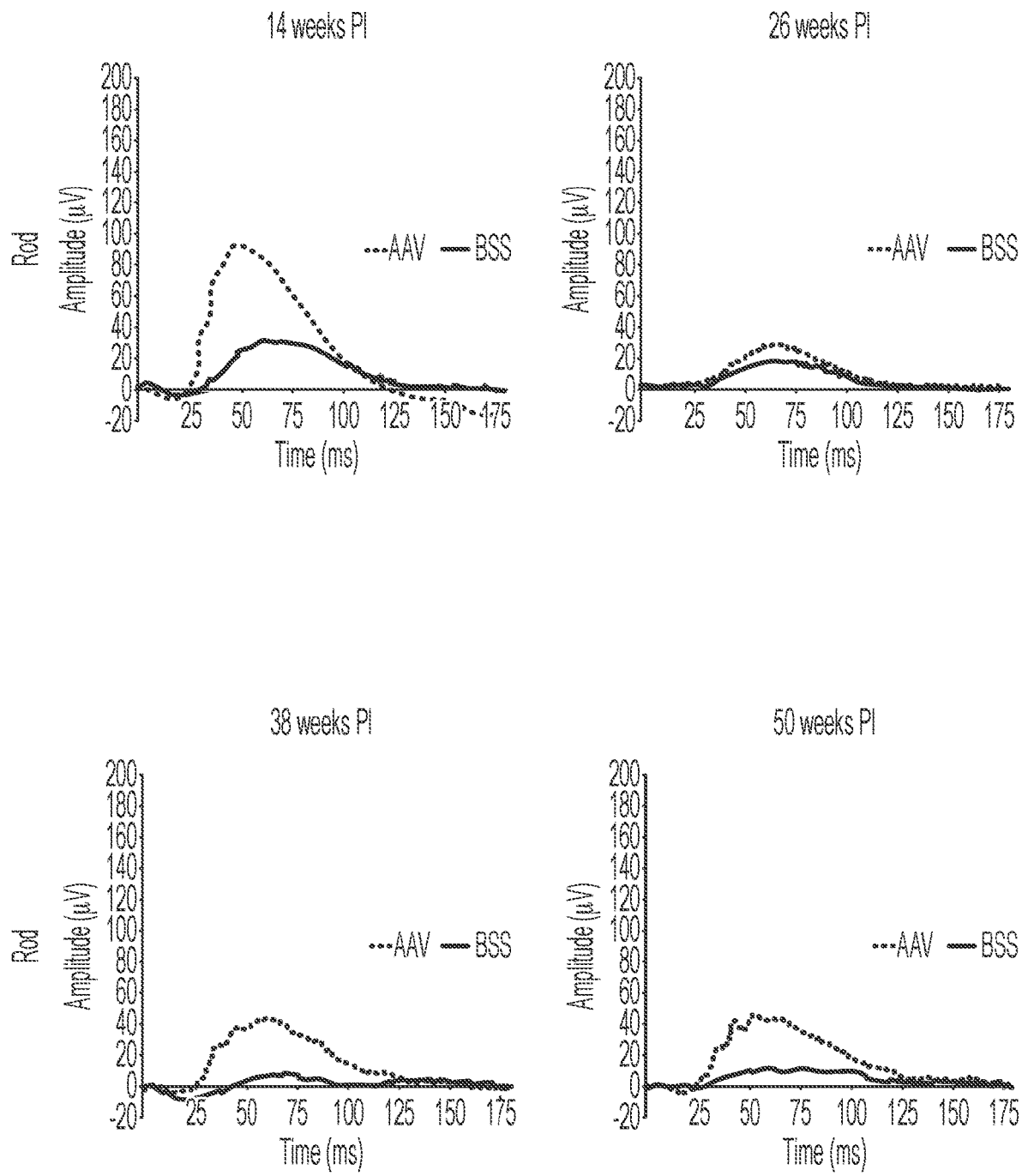
FIGS. 18A-18D show representative ERG traces of rod (−1.7 log cd·s·m$^{-2}$, FIG. 18A), mixed rod-cone (0.51 log cd·s·m$^{-2}$, FIG. 18B) recorded dark adapted, and cone responses to single stimuli (0.51 log cd·s·m$^{-2}$, FIG. 18C) or 29-Hz cone flicker (0.26 log cd·s·m$^{-2}$, FIG. 18D) recorded light adapted at ~2 weeks after each of four light exposure sessions in a RHO-mutant dog injected in one eye with scAAV2/5-hOP-RHO820-H1-shRNA820 (dotted line) and with BSS (solid line) in the contralateral eye.
Figure 18B:
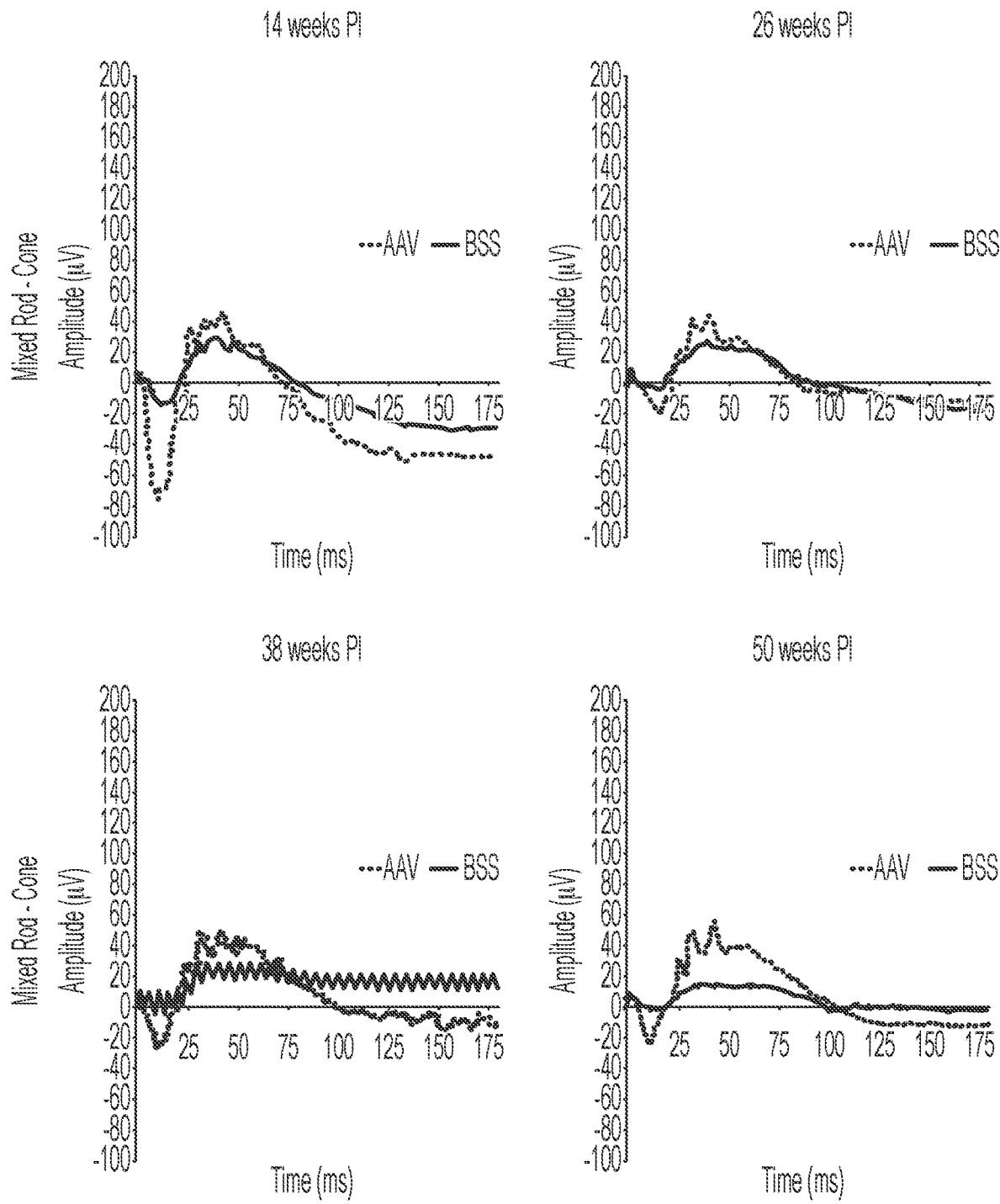
Figure 18C:
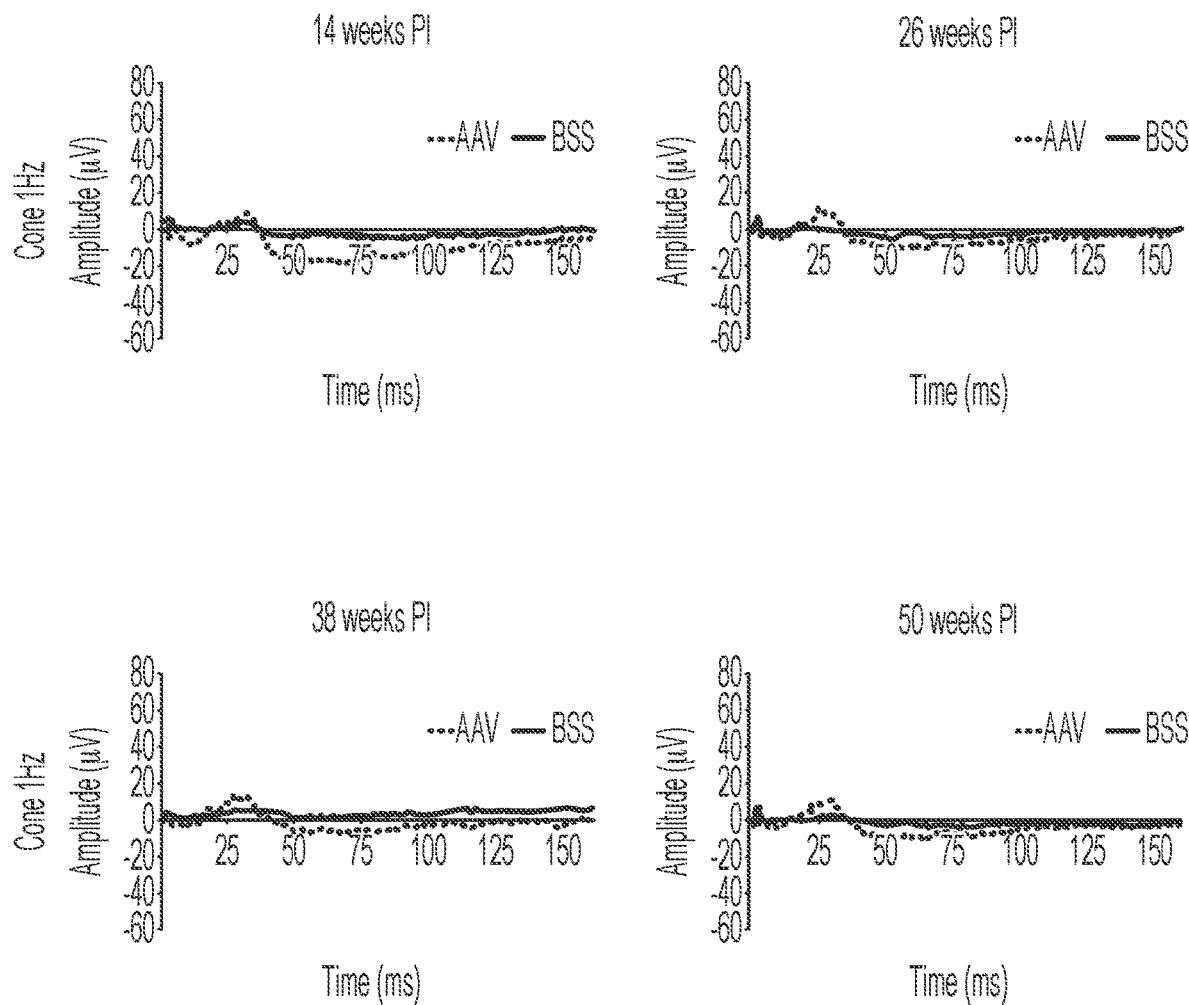
Figure 18D:
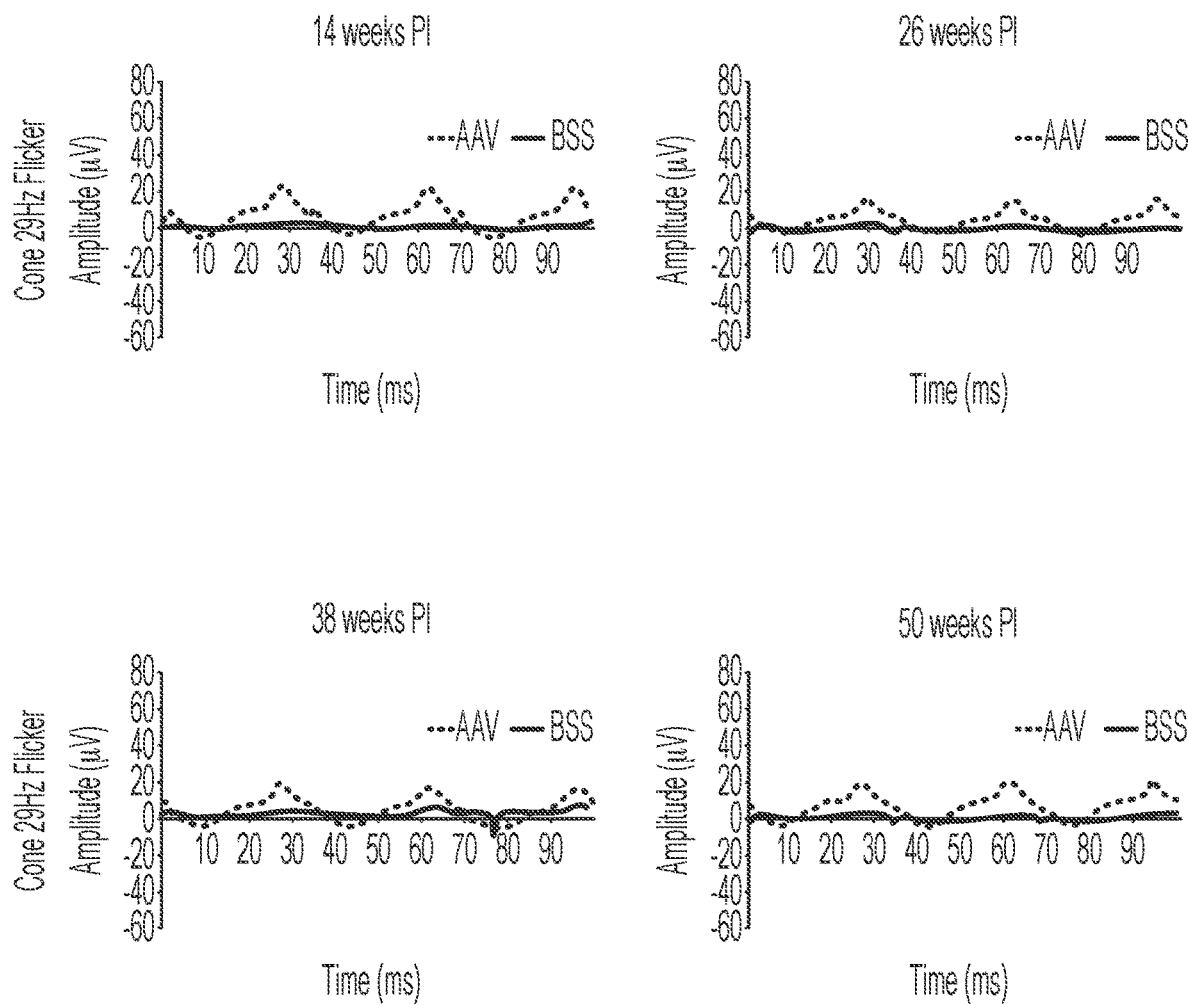

Long-Term Efficacy of AAV2/5-RHO$_{820}$-shRNA$_{820}$ in Preventing the Onset of Retinal Degeneration from Repeated Light-Exposure in Canine T4R Model of RHO-adRP The efficacy of the AAV2/5 vector over a period of fifty weeks was evaluated in mutant RHO$^{T4R/+}$ canines. Ability of the vector to confer stable protection of photoreceptors against light-induced retinal degeneration in untreated RHO$^{T4R/+}$ dog retinas was evaluated structurally by OCT and IHC and functionally by ERG. At 12, 24, 36 and 48 weeks post-injection, the retinas of these dogs were challenged by an acute light exposure event. OCT and ERG examination were conducted during the course of the study. At termination of the experiment (50 weeks post-injection), retinal tissues were processed for IHC. An illustration of the experimental design is shown in FIG. 17.

ERG measurements showed significantly better rod- and cone-mediated function in the AAV—than in the BSS-treated eyes. FIGS. 18A-18D show representative ERG traces of rod (−1.7 log cd·s·m$^{−2}$), mixed rod-cone (0.51 log cd·s·m$^{−2}$) recorded dark-adapted, and cone responses to single stimuli (0.51 log cd·s·m$^{−2}$) or 29-Hz cone flicker (0.26 log cd·s·m$^{−2}$) recorded light-adapted, at ~2 weeks after each light exposure event in a dog injected in one eye with scAAV2/5-hOP-RHO$_{820}$-H1-shRNA$_{820}$ (dotted line) and with BSS (solid line) in the contralateral eye.

Figure 19A:
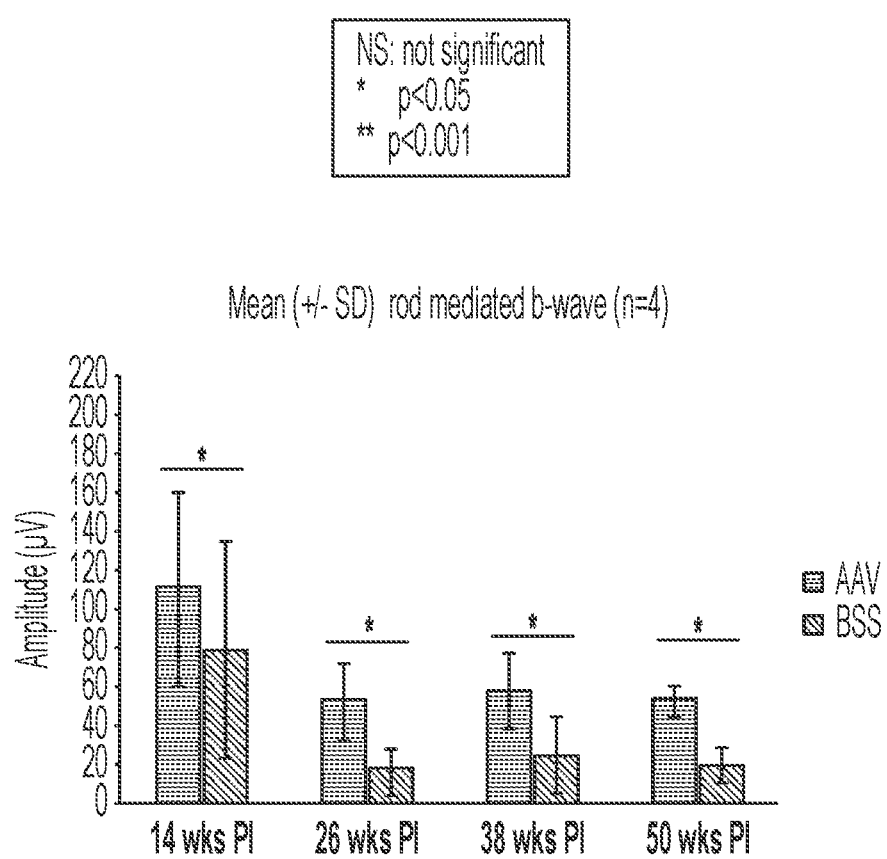
Figure 20A:
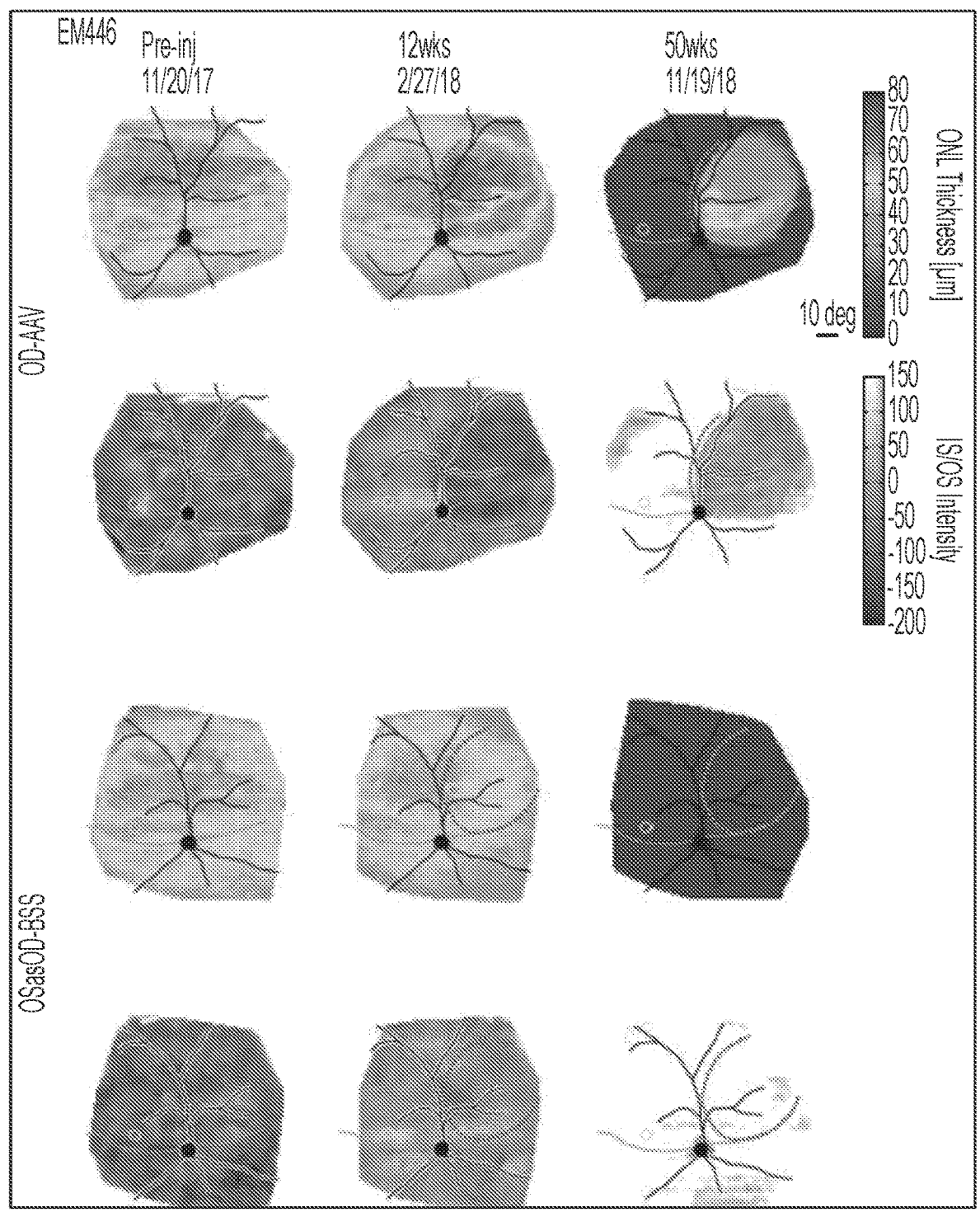
FIGS. 20A-20D show for each of the four RHO-mutant dogs outer nuclear layer (ONL) thickness maps and inner segment-outer segment (IS/OS) intensity maps prior to injection (pre-inj.), 12 weeks post-injection (before the first light exposure event), and 50 weeks post-injection (2 weeks after the fourth light exposure event).
Figure 20B:
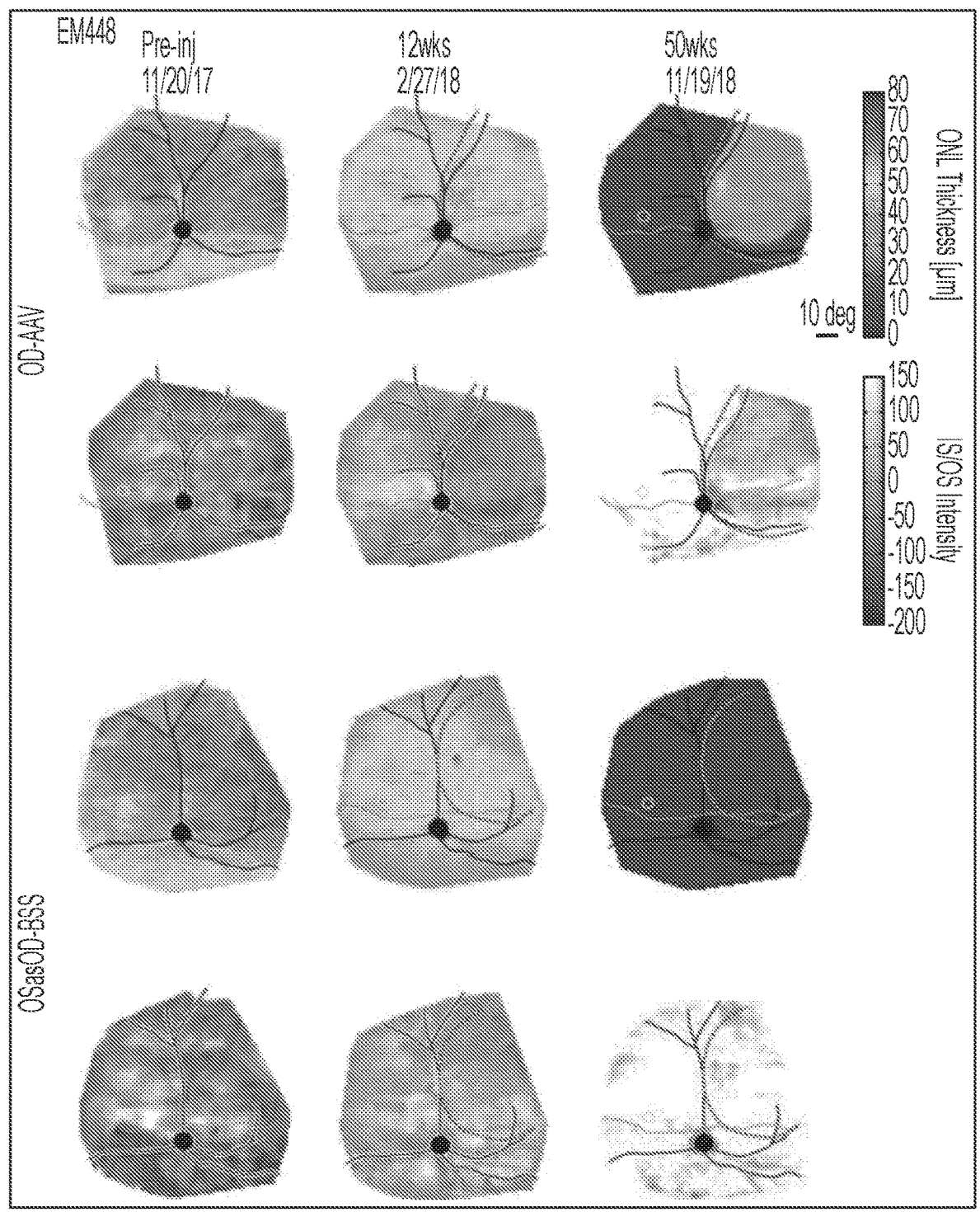
Figure 20C:
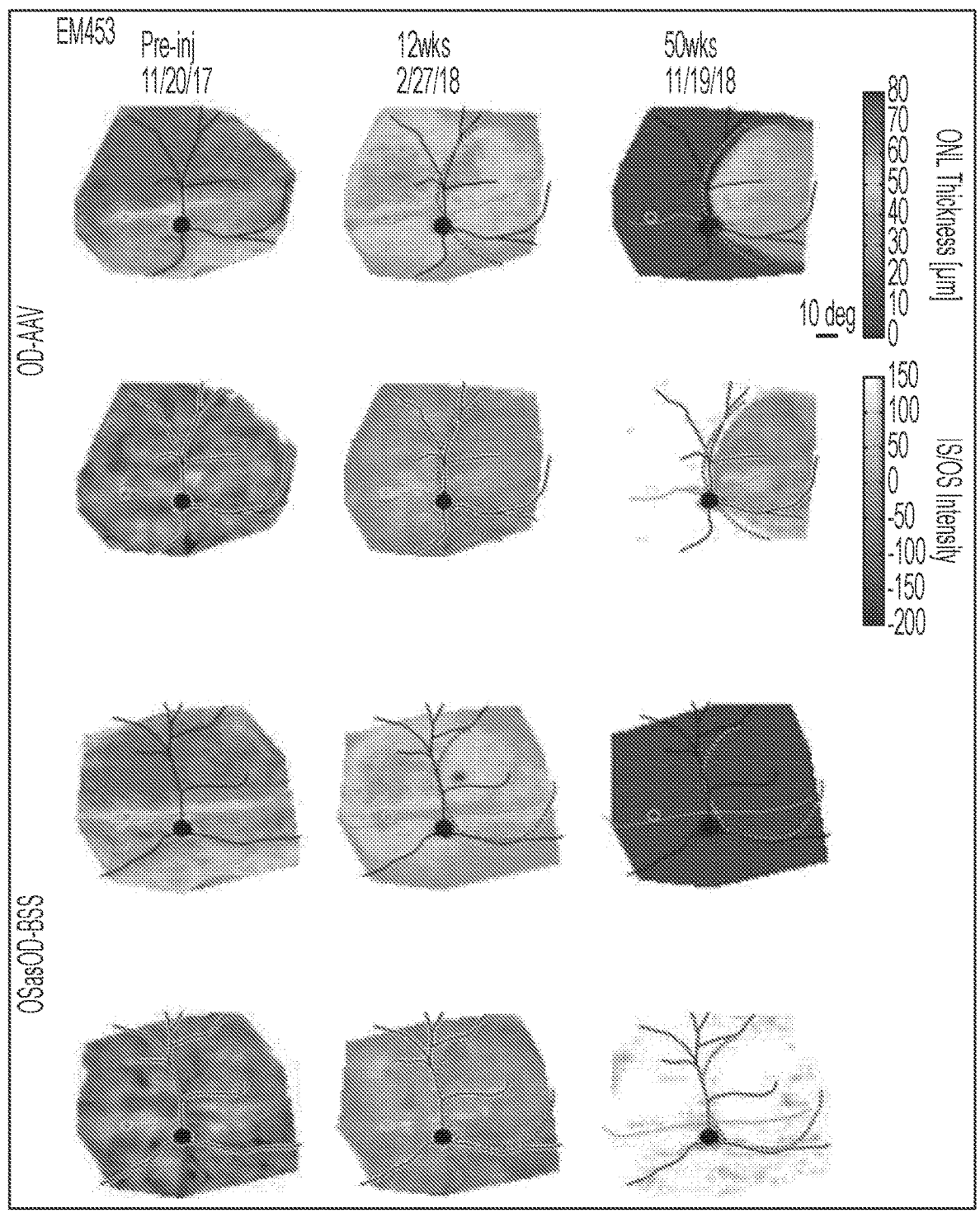
Figure 20D:
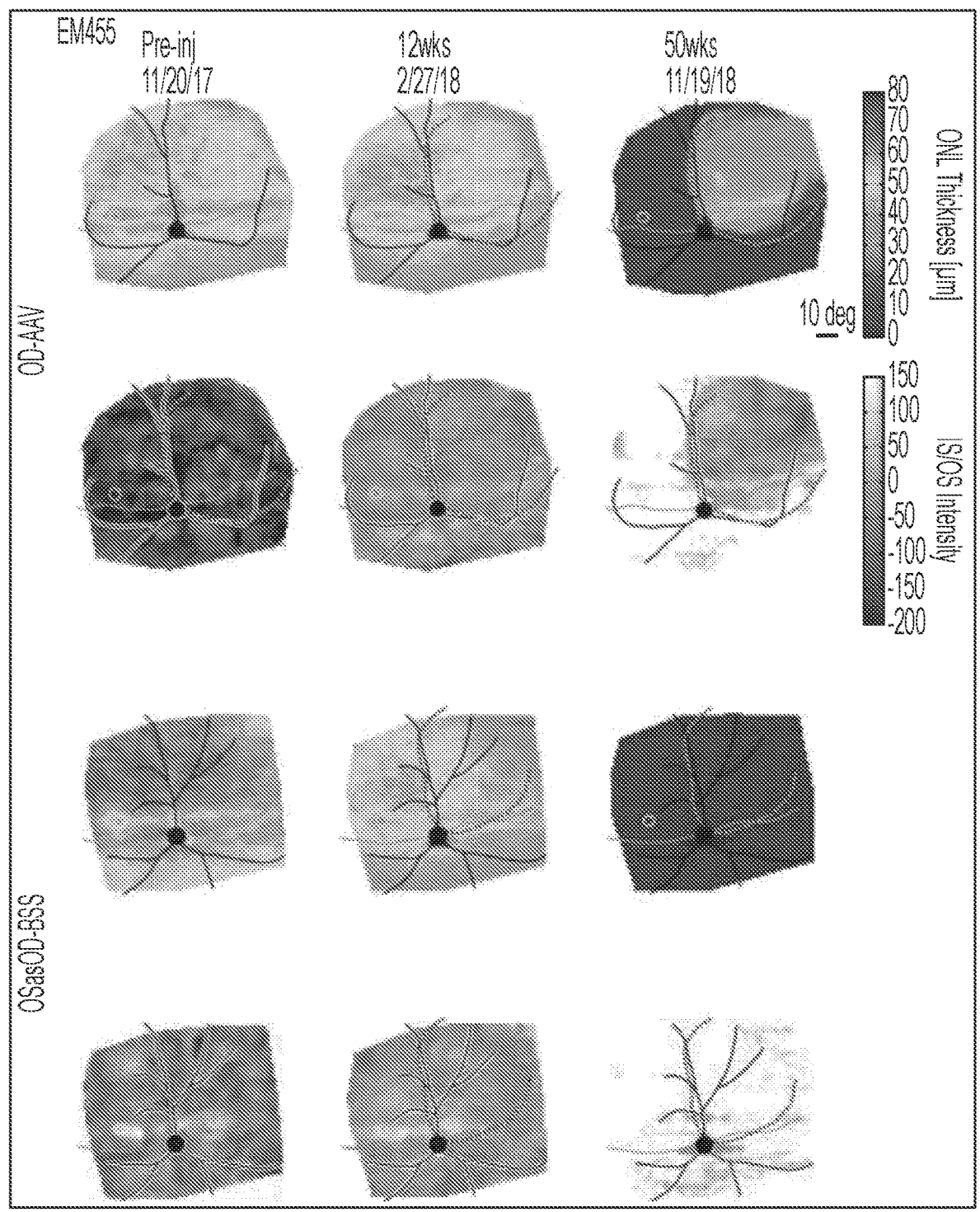

The four RHO-mutant dogs were injected in one eye with scAAV2/5-RHO$_{820}$-shRNA$_{820}$ (horizontal line shading) and in the contralateral eye with BSS (diagonal line shading) at similar time-points as shown. Longitudinal quantification of maximal amplitudes of rod b-wave, mixed rod-cone a- and b-waves, and of cone 1 Hz and 29 Hz flicker responses are displayed in FIGS. 19A-19C. The electrical response from photoreceptors is termed the a-wave and the electrical response from the bipolar cells of the retina is termed the b-wave.

OCT analysis showed preservation of outer nuclear layer (ONL) thickness in the AAV-treated areas while no protection was seen outside of the treated areas nor in the BSS-treated regions. In vivo results were confirmed by histology/IHC that showed preservation of ONL and both rods and cones inner and outer segments. For each of the RHO-mutant dogs, ONL thickness maps and inner segment-outer segment (IS/OS) intensity maps are shown in FIGS. 20A-20D prior to injection (pre-inj.), 12 weeks post-injection (before the first light exposure event), and 50 weeks post-injection (2 weeks after the fourth light exposure event).

Figure 21:
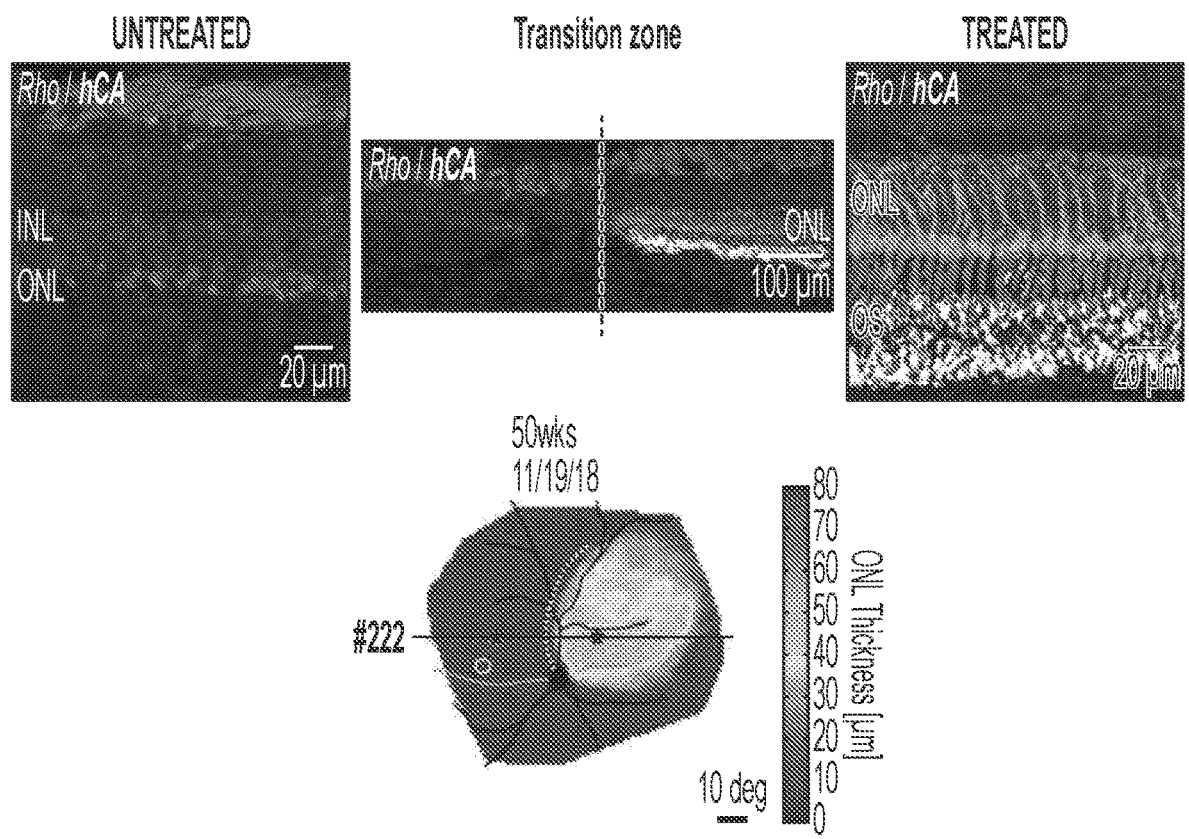
FIG. 21 shows rhodopsin (RHO)/human cone arrestin (hCA) co-immunolabeled retinal cryosection from a RHO-mutant dog illustrating the morphology of the outer nuclear layer (ONL) and outer segments (OS) in untreated and treated areas of the same eye. The ONL thickness maps (lower image) shows the approximate location (asterisk) of the retinal untreated and treated areas shown in the upper image.

A rhodopsin (RHO)/human cone arrestin (hCA) co-immunolabeled retinal cryosection from a RHO-mutant dog illustrates the morphology of the outer nuclear layer (ONL) and outer segments (OS) in untreated and treated areas of the same eye (see FIG. 21). The ONL thickness maps in the lower panel of FIG. 21 shows the approximate location (asterisk) of the retinal untreated and treated areas shown in the upper panel. The transition zone between treated and untreated areas of the eye is shown for reference.

The results show that the AAV2/5-hOP-RHO$_{820}$-H1-shRNA$_{820}$ construct confers stable structural protection of photoreceptors against light-induced retinal degeneration up to 50 weeks post-injection in a canine model of RHO-adRP. The results further show that the AAV2/5-hOP-RHO$_{820}$-H1-shRNA$_{820}$ construct confers stable functional (electroretinography) protection of photoreceptors against light-induced retinal degeneration up to 50 weeks post-injection in a canine model of RHO-adRP. These results show an extension of the above-demonstrated stability of protection by 13 weeks, and confirm structural preservation of rods and cones in the treated area.

Discussion

Despite considerable efforts at developing gene therapies for autosomal dominant diseases (50) only two involving antisense technology (ASO, siRNA) have reached the clinical trial stage, and these are for systemic diseases without a retinal phenotype (NCT01041222; NCT02363946). The development of mutation-independent gene knockdown and replacement approaches have been explored for the treatment of dominantly inherited systemic and retinal diseases that result from toxic gain-of-function mutations, and/or to circumvent high mutational heterogeneity.(40-43, 51, 52) A significant challenge, that likely has delayed the development of clinical therapies, is the need to successfully finetune the level of reduction of both mutant and WT endogenous proteins while providing sufficient resistant replacement.(53) Here, it is shown in a naturally-occurring form of RHO-adRP, and in a large animal model, that this dual-function strategy can effectively provide long-term photoreceptor rescue. In addition, it is shown that when both knockdown and replacement components are co-delivered in the same viral vector, they provide increased efficacy and a better safety profile than when delivered separately.

Rapid Assessment of Gene Therapy Efficacy in a Naturally-Occurring Large Animal Model of RHO-adRP Genetic approaches that include gene augmentation, mutation-dependent RHO suppression, and mutation-independent RHO knockdown and replacement, have been tested to date only in transgenic animal models of RHO-adRP. These include the hP23H mouse (5, 41, 43) the hP347S mouse (36, 38, 42, 54) and the mP23H (lines 1 and 3) rat (22, 23, 25, 26, 33). The use of animal models that have different ratios of mutant transgene to endogenous RHO copy numbers complicates making comparisons of photoreceptor rescue outcomes among these studies, and precludes estimating their potential efficiency in a human RHO-adRP retina. More recently, a P23H opsin knock in mouse that expresses equal levels of murine P23H and WT RHO was generated.(55) However, this model would have had no use in the current study as the target site for shRNA820 in canine and human RHO RNA is not conserved in the mouse.

To increase the predictive value of these studies in the context of a future human clinical trial, the RHO T4R mutant dog was used, which is the only naturally-occurring model of RHO-adRP (56). Besides its translational value for its human-sized eye, and its phenotypic similarities with Class B patients (56), the $RHO^{T4R/+}$ dog expresses equal amounts of mutant and WT RHO proteins (57). Both forms traffic normally to the rod outer segments (57) and sustain normal retinal structure and function until progressive areas of photoreceptor loss are detected in the inferior-temporal (FIGS. 15A-15C) and central retina (56) within the first two years of life. Sensitivity to light, which has been recognized in other models of RHO-adRP (47) and suspected in Class B patients (19, 45, 58-60), has been well characterized in the canine RHO T4R model.(45) Capitalizing on this light sensitivity, a light exposure protocol was previously developed to experimentally trigger a rapid and synchronized loss of photoreceptors and accelerate the natural disease course. (46) RHO-mutant (but not WT) dogs undergo a complete loss of rods in the central to mid-peripheral retina within two weeks following an acute (1 minute) light exposure using intensity levels encountered in clinical patient settings.(47, 48) Here, this "disease-acceleration" approach was used to obtain a rapid read-out of the effect of gene therapy intervention on preventing rod degeneration in RHO-mutants.

RHO Suppression: The Need for a Potent Knockdown Component

Figure 3D:
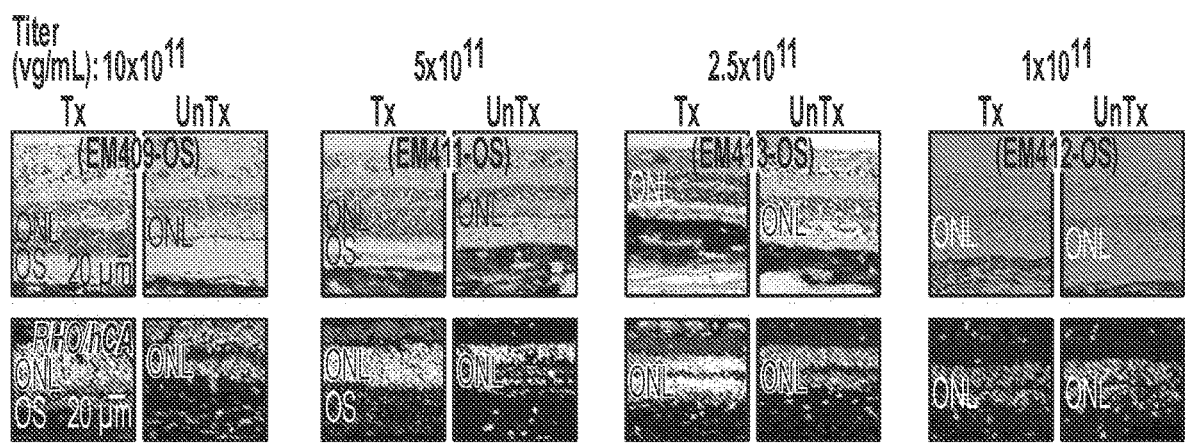

Evidence from several animal model studies suggests that a toxic gain-of-function mechanism is associated with a number of RHO mutations including P23H (55, 61, 62) T17M (63, 64) and T4R/T4K (45, 64). This toxicity may be exacerbated following exposure to light in many RHO-adRP models including the RHO-mutant dog (47). Thus, it was posited that under normal ambient illumination, the T4R mutation produces a protein that is highly toxic once bleached, but stable when bound to chromophore (57), and that efficient protection of rods would require significant knockdown of the mutant transcript. This study examined the efficiency of several RHO knockdown reagents including three shRNAs and a hammerhead ribozyme with the goal of identifying the most potent reagent capable of suppressing RHO expression. Rz525 tested in the RHO-mutant dog produced a 64% reduction in endogenous canine RHO protein that was not sufficient to confer protection from light-induced retinal degeneration (FIGS. 10C-10D). This confirmed the high toxicity of the native mutant T4R protein, since remaining amounts as low as 18% of physiological levels of RHO were sufficient to cause disease in a heterozygous mutant retina, and argued for the need to achieve more efficient suppression. When a complete suppression of RHO protein was obtained with Rz525, some ONL rescue was observed, but the need for a high viral titer ($10^{13}$ vg/mL) was associated with severe retinal inflammation (FIGS. 10C-10E). Based on these results, only the most efficient shRNA (shRNA$_{820}$) identified following in vitro and screening and testing in WT dogs, was subsequently evaluated in mutants. Results confirmed that optimal rescue occurred only when complete suppression of RHO protein expression was achieved, while 86% knockdown of RHO provided only partial protection (FIGS. 3C-3D). Some of the most efficient knockdown reagents reported to date have achieved a 90-95% suppression of human RHO RNA, but these results were obtained on FACS-sorted transduced rods.(36, 41) Here, levels of remaining RHO RNA and protein was intentionally measured from biopsy punches of neuroretina collected within the treated area rather than from an enriched population of transduced rods. The results show a complete knockdown of RHO message and product in RHO-mutant retinas (FIGS. 3B-3C), suggesting not only that shRNA$_{820}$ is extremely potent but also that rod transduction efficiency was very high. Importantly, this was achieved with an AAV2/5 titer as low as $5 \times 10^{11}$ vg/mL, which previously has been shown to be within the range of well-tolerated titers in dog retinas (44, 65, 66). The near complete suppression of RHO protein expression in WT and RHO-mutant dogs was associated with a loss of OS, similar to the collapse of rod outer segment structure reported by others.(36, 54) It is important to note that suppression of RHO was not associated with any reduction in ONL thickness suggesting that rods can survive for at least 10 weeks following administration of shRNA$_{820}$. This interval provides a window for concomitant expression of a resistant RHO replacement component to produce sufficient protein to prevent outer segment deconstruction or initiate outer segment regeneration.

RHO Replacement: How Much is Enough/Too Much?

As little as 23% overexpression of rhodopsin has been shown to cause retinotoxicity in transgenic mice, (67, 68) thus calling for tight regulation of RHO gene supplementation strategies. However, retinal degeneration was not observed when RHO gene augmentation was delivered postnatally in the hP23H $RHO^{+/-}$, $mRHO^{+/+}$ transgenic mouse. This genetic configuration led to a two-fold increase in RHO RNA and a 58% increase in RHO protein, and resulted in both structural and functional rods for up to 6 months post-treatment.(5) These apparently conflicting results suggest that mature rods may tolerate higher levels of RHO overexpression than developing photoreceptors. In the current study, gene augmentation was not considered in the RHO-mutant dog due to the highly toxic gain-of-function of the T4R mutation, but also because this strategy had failed to confer protection when tested in the hP23H RHO$^{+/-}$, mRHO$^{+/-}$ transgenic mouse that carries one mutant (hP23H) and one WT (mRHO) allele.(43) Instead, replacement with a resistant RHO cDNA (RHO$_{820}$) was evaluated together with shRNA$_{820}$-mediated RHO suppression. In the treated areas of mutant retinas injected 9 weeks prior with AAV2/5-shRNA$_{820}$-RHO$_{820}$, total RHO protein levels as low as 18% of that found in untreated regions (FIG. 4H) were sufficient to preserve rod outer segment structure (FIG. 4C, FIG. 14C). When retinas from two additional injected eyes were processed 4 weeks later (13 weeks post-injection), higher protein amounts (up to 33% of untreated areas) were measured (FIG. 4H) which also sustained outer segment formation (FIGS. 4D, 14D). These findings suggest that the kinetics of RHO replacement are slower than suppression, and that maximal levels of RHO expression may not be reached until several weeks post treatment.

Figure 4F:
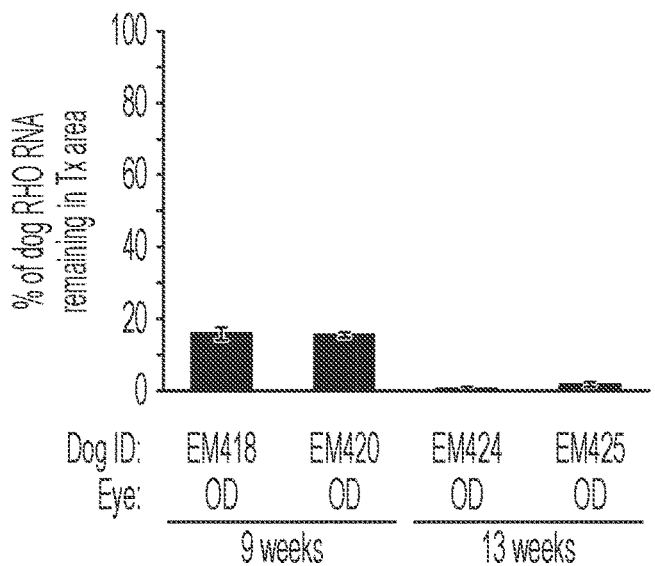
Figure 4G:
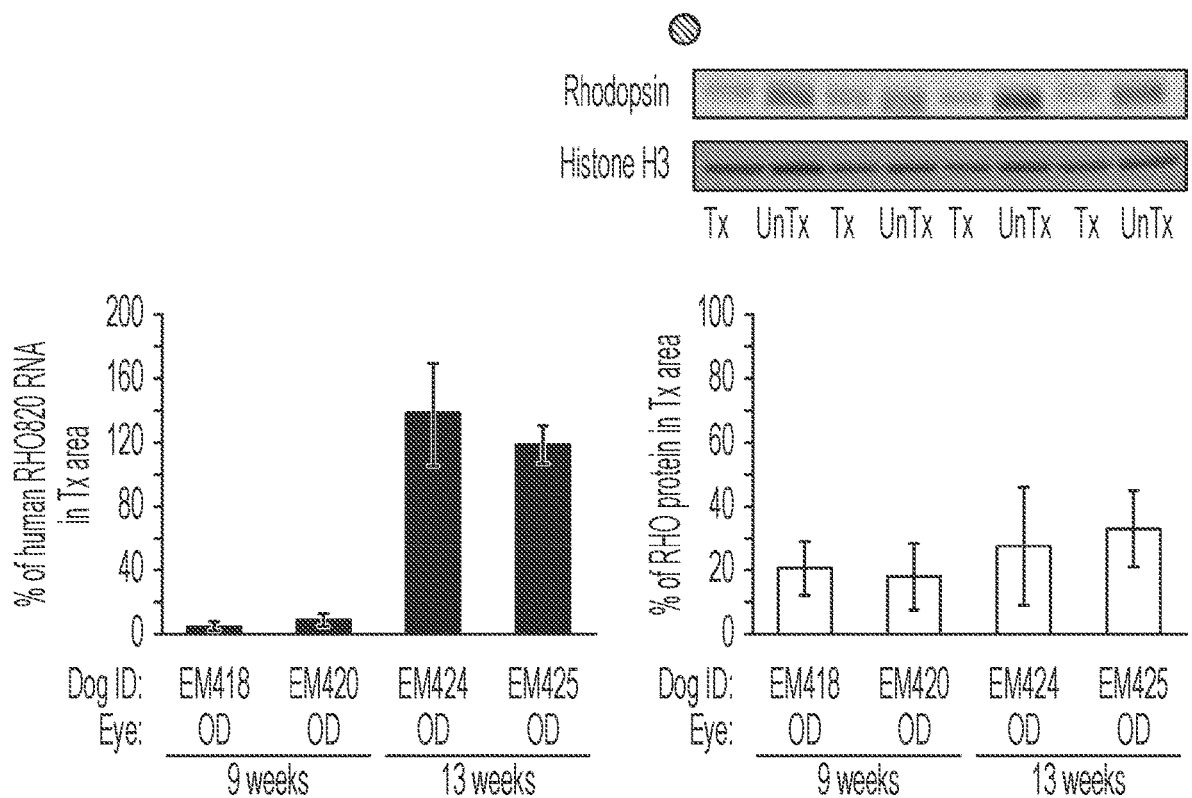

Combining Knockdown and Replacement in a Single Vector Achieves Optimal Efficiency and Improved Safety Over a Two-Vector Approach Previous efforts at co-packaging the knockdown and replacement reagents within a same viral vector provided short-term (10 days post-injection) preservation of ONL thickness, but failed to rescue rod outer segment structure in a hP23H RHO$^{+/-}$, mRHO$^{+/-}$ transgenic mouse.(41) This led to consideration of a two-vector approach whereby the knockdown and replacement reagents were packaged separately enabling co-administration of different ratios of the two vectors to better control the levels of RHO suppression and replacement. This strategy achieved preservation of ONL thickness, rod outer segment structure, and ERG function in the hP347S RHO$^{+/-}$, mRHO$^{+/-}$ transgenic mouse, but the effect was not sustained.(42) In the current study, co-injection of AAV-shRNA$_{820}$ and AAV-RHO$_{820}$ led to some degree of protection against light-exposure, yet signs of severe retinal inflammation were observed, likely because of the combined higher viral doses administered (FIGS. 13A-13G). This finding led to the pursuit of the single vector dual-function strategy that was previously successfully evaluated in a mouse model. (43) ShRNA820, and RHO$_{820}$ driven respectively by the human H1 RNA and the human opsin proximal promoters were successfully packaged within the cargo capacity limit of the recombinant AAV cassette. The efficiency of this construct remained very high, achieving suppression of ~98.5% of endogenous canine RHO RNA at 13 weeks post injection, and expression of human RHO$_{820}$ at levels comparable to normal. Yet, at the protein level, replacement resulted in only about a third of normal levels. This discrepancy between RNA and protein levels could be explained by several factors including the possibility that synonymous codon modifications introduced at wobble/degenerate sites to generate the resistant RHO$_{820}$ cDNA influenced its translation efficiency. Analysis of codon frequency of the four modified codons at the RHO target site of shRNA$_{820}$ showed for both dog and man an increase in frequency for two codons, a decrease in frequency for the two others, and an overall decrease when all four were combined (Table 2). Since a correlation has been found between codon usage and relative tRNA abundance in particular for highly expressed genes that are tissue-specific (69) the introduction of two codons with lower frequency could have led to a reduced rate of RHO$_{820}$ translation.(70) It may be possible, therefore, to improve rhodopsin expression by reducing the number of modifications in the replacement gene. A single mismatch between an siRNA and a mRNA may be sufficient to block RNA silencing, if the mismatch occurs near the RISC-mediated cleavage site.(71) Another possible explanation unrelated to codon bias maybe that the kinetics of RHO suppression are faster than that of RHO replacement. The H1 RNA polymerase III promoter used in the vector is considered safer that the more potent U6 promoter, which leads to a very high level of shRNA expression and, potentially, to saturation of the processing system for endogenous miRNAs. Nevertheless, H1 RNA is expressed abundantly, and the promoter used here functions in all cell types tested.(72, 73) This could explain why at 9 weeks post-injection there was already prominent reduction (~84%) of endogenous RHO RNA levels while RHO$_{820}$ RNA levels reached only 5-9% of normal (FIGS. 4F-4G). While immuno-histochemical analysis revealed the presence of RHO protein in structurally-preserved OS, retinal OCT imaging of the IS/OS intensity, a novel surrogate marker of IS/OS integrity, showed that the signal, although detectable, was decreased at 9 and 13 weeks post-injection (FIGS. 4A-4B, FIGS. 14A-14B). Longitudinal analysis in two RHO-mutant dogs treated with AAV-shRNA$_{820}$-RHO$_{820}$ submitted to four acute light-exposure events showed a similar decline in IS/OS intensity that peaked at ~12 weeks post-injection followed by a gradual and near complete recovery by 37 weeks. Ongoing studies aimed at examining retinal structure at earlier and later time-points after injection will inform as to whether rod outer segment undergo first a deconstruction followed by a gradual reconstruction with disc material composed of resistant RHO$_{820}$ protein, or whether sufficient levels of RHO$_{820}$ are produced early enough to prevent outer segment shortening.

Functional Assessment

Successful and complete protection of rods was achieved over the long-term (50 weeks/11.5 months) following a single subretinal injection of AAV-shRNA$_{820}$-RHO$_{820}$ in mutants that repeatedly had acute light exposures that cause complete loss of rods in the central to mid-peripheral retina after just a single event. Substantially improved ERG responses were consistently seen in AAV-treated eyes at all time points. While cone-mediated ERG response was stable, a slight decline of rod-dominated ERG function was noted. A slight increase in ONL thickness seen in other studies (74, 75) in dogs injected with AAV-mediated gene therapy was also observed here in the treated areas, and likely reflects intra- or intercellular swelling due to mild retinal stress. The transitory and mild ONL thickening was likely associated with the vector since neither the BSS injected eyes before light exposure nor the natural history of uninjected RHO-mutant dogs housed under standard or dim red cyclic illumination demonstrated evidence of abnormal thickening of the ONL (FIGS. 15A-15C). The return of ONL thickness to normal pre-injection values ruled out the hypothesis that the observed ERG decline was associated with photoreceptor loss within the treated regions. Instead, the functional decline is likely explained by the additional loss of rods located in the untreated peripheral retina following cumulative light exposure, and this hypothesis is consistent with the similar decline in rod-dominated ERG amplitudes found in the contralateral BSS-injected eyes.

In summary, a novel single vector with dual RHO knockdown and replacement functions has been developed, that provides complete and long-term protection of rods against a Class B RHO mutation with toxic gain-of-function identified in a naturally-occurring large animal model of RHO-adRP. This highly efficient mutation-independent strategy raises hope that a common gene therapy for all RHO-adRP patients with Class B mutations will be an achievable goal.

Example 2: The Construct can Protect Against Retinal Degeneration in Mice

The AAV-shRNA$_{820}$-RHO$_{820}$ construct provided long-term protection against retinal degeneration in a mouse model of RHO-adRP.

C57Bl/6 mice transgenic for human P23H RHO are subject to retinal degeneration due to the presence of the mutant rhodopsin gene, even in the presence of dim red lighting without exposure to bright light (33, 34, 43). At one month of age, mice of this genotype were treated with a subretinal injection of either AAV2/5-GFP or scAAV2/5-RHO$_{820}$-shRNA$_{820}$ into one eye. The two groups of mice were analyzed at varying intervals: a) pre-treatment, b) 1 month post-injection, c) 2 months post-injection, and d) 3 months post-injection. Subretinal injection induced temporary retinal detachment that ultimately resolved. Contralateral eyes were not treated.

Figure 22:
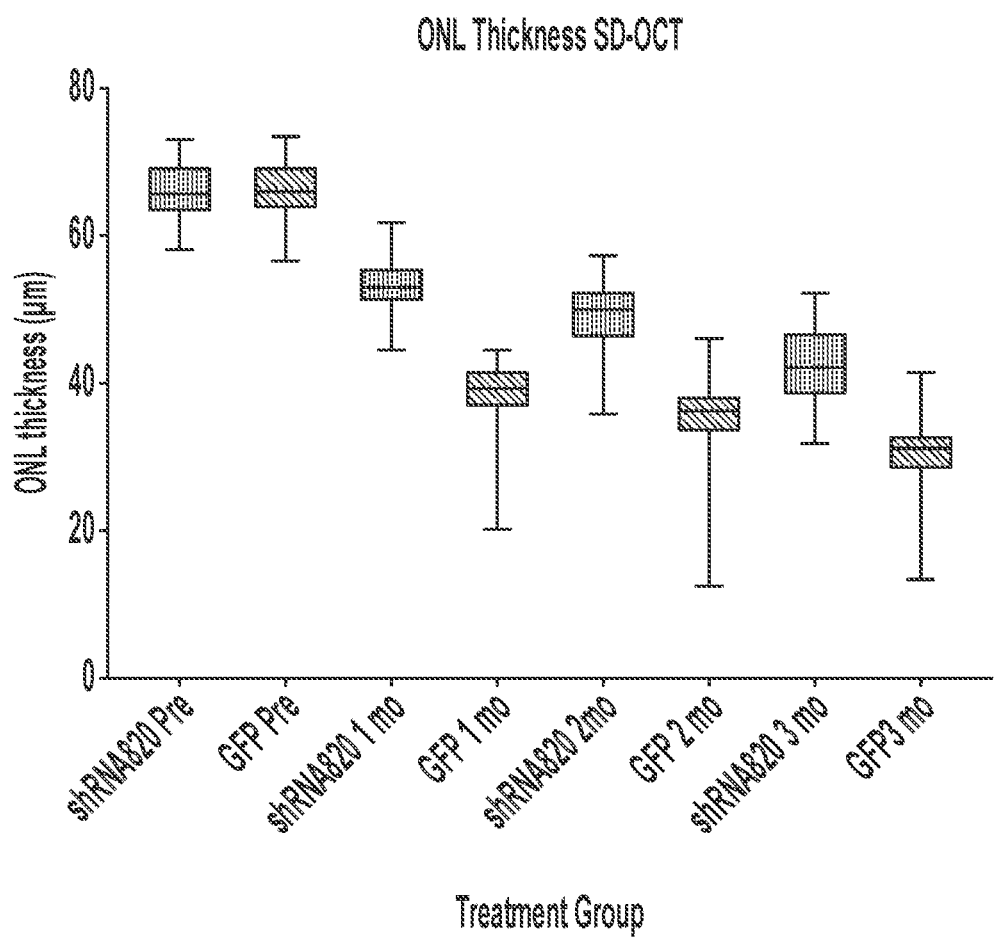
FIG. 22 shows OCT measurements of outer nuclear layer (ONL) thickness in mice treated with scAAV2/5-RHO$_{820}$-shRNA$_{820}$ or AAV2/5-GFP. P23H RHO C57Bl/6 mice were treated with either AAV2/5-GFP or scAAV2/5-RHO$_{820}$-shRNA$_{820}$ in one eye, and ONL thickness was analyzed at varying intervals: a) pre-treatment ("Pre"), b) 1 month post-injection, c) 2 months post-injection, or d) 3 months post-injection.

OCT analysis was performed in the P23H RHO mice at monthly intervals for three months to determine the effect of vector treatment on outer nuclear layer (ONL) thickness. ONL thickness was substantially reduced 2 months and 3 months post-injection relative to pre-treatment. In addition, treatment with scAAV2/5-RHO$_{820}$-shRNA$_{820}$ led to a statistically significant preservation of ONL thickness relative to AAV2/5-GFP treatment at all post-injection intervals (see FIG. 22).

Overall, thirty P23H mice were successfully treated with scAAV2/5-RHO$_{820}$-shRNA$_{820}$, while twenty-six mice were successfully treated with AAV2/5-GFP. As determined in the Tukey's multiple comparisons test illustrated in Table 3 below, scAAV2/5-RHO$_{820}$-shRNA$_{820}$ treatment led to a statistically significant degree of protection of retinal structure in P23H RHO mice relative to AAV2/5-GFP treatment.

Dark adapted electroretinography analysis was performed on the same treated groups of P23H RHO mice at monthly intervals for three months. The corneal electrical responses of these mice to brief flashes of light of varying intensities (-20 decibels, -10 decibels and 0 decibels) was measured using corneal electrodes. Longitudinal quantification of maximal amplitudes of rod a- and b-waves (in response to -20 dB and -10 dB flashes) and mixed rod and cone a- and b-waves (in response to 0 dB flashes) at each interval are displayed in FIG. 23.

As determined in the student's t test illustrated in Table 4 below, scAAV2/5-RHO$_{820}$-shRNA$_{820}$ treatment led to a statistically significant degree of protection of retinal function three months post-injection in P23H RHO mice relative to AAV2/5-GFP treatment ("ns"=not significant).

These results show that the AAV2/5-hOP-RHO$_{820}$-H1-shRNA$_{820}$ construct confers stable structural protection of photoreceptors against retinal degeneration in a mouse model of RHO-adRP. The results further show that this construct confers stable functional (electroretinography) protection of photoreceptors against retinal degeneration in this mouse model.

TABLE 3

| Tukey's multiple comparisons test | Mean Diff. | 95.00% CI of diff. | Significant? | Summary | Adjusted P Value |
|---|---|---|---|---|---|
| shRNA820 Pre vs. GFP Pre | -0.3341 | -4.624 to 3.956 | No | ns | >0.9999 |
| shRNA820 Pre vs. shRNA820 1 mo | 12.68 | 8.551 to 16.82 | Yes | **** | <0.0001 |
| shRNA820 1 mo vs. GFP 1 mo | 14.99 | 10.77 to 19.21 | Yes | **** | <0.0001 |
| shRNA820 Pre vs. shRNA820 1 mo | 12.68 | 8.551 to 16.82 | Yes | **** | <0.0001 |
| shRNA820 2mo vs. GFP 2 mo | 13.96 | 9.060 to 18.86 | Yes | **** | <0.0001 |
| shRNA820 Pre vs. shRNA820 2mo | 17.04 | 12.70 to 21.38 | Yes | | <0.0001 |
| shRNA820 3 mo vs. GFP 3mo | 13.15 | 7.966 to 18.33 | Yes | **** | <0.0001 |
| shRNA820 Pre vs. shRNA820 3 mo | 22.78 | 18.22 to 27.34 | Yes | **** | <0.0001 |

TABLE 4

| | p-values | | | | | | | | |
|---|---|---|---|---|---|---|---|---|---|
| | 1 month, N = 24 | | | 2 month, N = 20 | | | 3 month, N = 20 | | |
| | -20 dB | -10 dB | 0 dB | -20 dB | -10 dB | 0 dB | -20 dB | -10 dB | 0 dB |
| a- wave | ns | ns | ns | ns | ns | ns | ns | 0.01 | 0.003 |
| b- wave | ns | 0.005 | <0.001 | 0.05 | ns | <0.001 | <0.001 | <0.001 | <0.001 |

Example 3: Analysis of the mRNA Sequences Expressed from the Vector Construct To determine the types of short mRNA sequences that are derived from the AAV construct, HEK293T cells were transfected with the scAAV2/5-RHO$_{820}$-shRNA$_{820}$ construct. 48 hours later, total RNA was extracted. Extracted RNA was size fractionated and short RNA sequences were subjected to RNA sequencing. RNA molecules with sequences derived from shRNA$_{820}$ were analyzed to determine their sizes and 5' and 3' ends (see FIG. 24).

Figure 25:
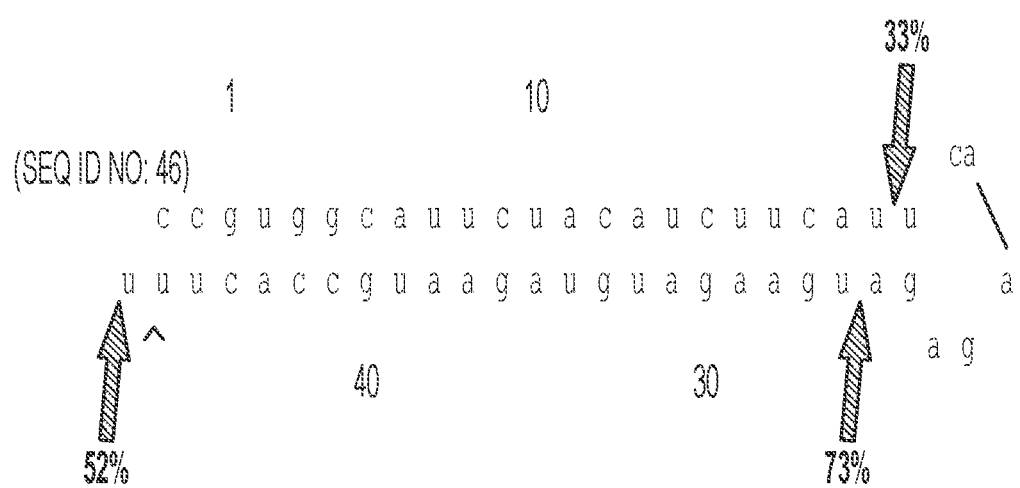
FIG. 25 shows the consensus sequence of the top "hits" of short mRNAs expressed in transfected HEK293 cells. As indicated by arrows, 52% of RNA molecules had 2 extra uridines at the 3' end. The sequence of the 5' end of the guide strand (UAG) in 73% of the RNA molecules was equivalent to what was predicted.

The summary of the sequencing reads is shown in FIG. 25. The sequence of the 5' end of the guide strand (UAG) in 73% of the RNA molecules was equivalent to the expected sequence. 13% of the molecules were shortened by one nucleotide at the 5' end. 52% had 2 extra uridines at the 3' end, while 10% had 1 extra uridine at the 3' end. 13% of molecules had an extra UUA codon at the 3' end. SEQ ID NOs: 40-46 are provided as the sequences of the most frequent short RNAs derived from shRNA$_{820}$ (top hits from both strands).

Most of the shRNA was processed as predicted at the 5' end, with some extra nucleotides present at the 3' end.

Significance

A number of gene augmentation strategies are entering clinical trials for the treatment of inherited retinal blindness. Gene therapy for autosomal dominant diseases faces significant obstacles that include allelic heterogeneity and the potential need to silence the mutated gene. Here, it is shown that a single gene therapy vector that combines knockdown of the causative gene with its replacement by a resistant wild type copy can prevent photoreceptor cell death and vision loss in canine and mouse models of autosomal dominant retinitis pigmentosa.

Materials and Methods

In vitro assays conducted in HEK293T (ATCC, Manassas, VA) cells (33) were used to screen the efficiency of a hammer-head ribozyme (Rz525) and three short hairpin RNAs (shRNA$_{131}$, shRNA$_{134}$, and shRNA$_{820}$) at suppressing WT and mutant (P23H, T17M) human RHO expression. (76) Self complementary (77) and non-self complementary AAV vectors were packaged in serotype 5 (78) by triple plasmid DNA transfection and were purified according to previously published methods.(79, 80) The titer of DNase-resistant vector genomes was measured by real-time PCR relative to a standard; purity was validated by silver-stained sodium dodecyl sulfate-polyacrylamide gel electrophoresis, sterility and absence of endotoxin were confirmed, and aliquots were stored at −80° C. before use. WT and RHO mutant dogs (45, 56) were used to evaluate the response to subretinal injections of AAV2/5 vectors carrying the most potent knockdown reagents, either alone (Rz525, shRNA820) or in combination (shRNA820) with a codon-modified resistant human RHO cDNA (RHO$_{820}$) (FIGS. 16A-16E). Assessment of the effect of RHO suppression and replacement was made by means of en face and cross sectional in vivo retinal imaging, electroretinography, quantification of RHO protein and RNA levels, and morphological evaluation on retinal histological sections.(74, 81-83) A light exposure paradigm (46-48) was used to accelerate the natural course of disease in the RHO mutant dogs and rapidly assess whether the subretinally-delivered AAV constructs prevented the onset of retinal degeneration. All dogs were bred and maintained at the University of Pennsylvania Retinal Disease Studies Facility (RDSF). The studies were carried out in strict accordance with the recommendations in the Guide for the Care and Use of Laboratory Animals of the National Institutes of Health, and the USDA's Animal Welfare Act and Animal Welfare Regulations, and complied with the ARVO Statement for the Use of Animals in Ophthalmic and Vision Research. The protocols were approved by an Institutional Animal Care and Use Committee. Methodological details are provided in below.

Ribozyme Cleavage Assay

HEK293T cells (CRL-11268, ATCC, Manassas, VA) were transfected with the dual luciferase plasmid psiCHECK™-2 (Promega, Madison, Wi) expressing a 100 nucleotide target region of either wild type or resistant (hardened) human RHO cDNA linked to the Renilla luciferase expressed by the SV40 promoter. RHO transcript levels were measured in six replicates by luciferase assay. The luciferase plasmid was co-transfected with a plasmid expressing Rz525 from the tRNAval promoter. Results were normalized to the same fusion transcript measured following co-transfection with a plasmid lacking ribozyme.

Generation of the RHO-tGFP and RHO$_{820}$-tGFP Expressing Plasmids

A plasmid containing the CMV-promoter, the human WT-RHO open reading frame (ORF) with a C-terminal turboGFP tag, and BGH-PolyA signal (also encoding ampicillin resistance and neomycin resistance genes) was used to express RHO in vitro. P23H RHO, T17M RHO, and RHO$_{820}$ versions of the CMV-hRHO-turboGFP-BGH-PolyA plasmid were created using the Q5® Site-Directed Mutagenesis Kit (New England Biosciences, Ipswich, MA., USA) according to the manufacturer's instructions, except with the PCR parameters described here. To generate the P23H RHO version, the 23$^{rd}$ codon of the hRHO ORF of the CMV-hRHO-turboGFP-BGH-PolyA plasmid was changed from CCC to CAC with the following primers: Forward—CACACCCGTCGCATTGGA (SEQ ID NO: 30), and Reverse—GTACGCAGCCACTTCGAGTAC (SEQ ID NO: 31). To produce the RHO$_{820}$ version, nucleotides 816 to 825 of the hRHO ORF in the CMV-hRHO-turboGFP-BGH-PolyA plasmid were changed from ATTCTACATC (SEQ ID NO: 32) to TTTTTATATA (SEQ ID NO: 33) with the following primers: Forward: ATATATTCACC-CACCAGGGCTCCAAC (SEQ ID NO: 34), and Reverse: AAAAAGCCA CGCTGGCGTAGGGC (SEQ ID NO: 35). The PCR reaction parameters were as follows: initial denaturation at 98° C. for 30 seconds, 25 cycles of denaturation (98° C. for 10 seconds, annealing for 30 seconds, extension at 72° C. for 5 minutes), final extension at 72° C. for 2 minutes. The annealing temperatures used for the P23H RHO and RHO$_{820}$ PCR reactions were 68° and 72° C., respectively. 25 µg of the CMV-hRHO-turboGFP-BGH-PolyA plasmid was used as the template for each reaction. The AAV-T17M-GFP was a gift of Dr. Marina Gorbatyuk. (76)

In Vitro Screening of shRNA-Mediated Knockdown of RHO

HEK293T cells (ATCC) were seeded in a 12-well plate and transfected the following day when the cells reached 70-90% confluency. Into each well, 500 ng of the CMV-hRHO-turboGFP-BGH-PolyA plasmid expressing either wild-type human RHO, human P23H RHO, human T17M RHO, or RHO$_{820}$ (a human RHO made resistant to shRNA$_{820}$ degradation via four silent codon modifications) was transiently co-transfected with 1 µg of a self-complementary rAAV2 plasmid containing an anti-sense GFP stuffer sequence and either a control H1-shRNA cassette, an on-target (131, 134, or 820) H1-shRNA cassette, or no (empty) H1-shRNA cassette. Each co-transfection condition was performed in triplicate. A DNA to polyethylenimine (PEI at 1 mg/mL; Polysciences Inc, Warrington, PA., USA) ratio of 1 µg:3 µL was utilized such that each well received 4.5 µL of PEI. The cells were incubated for 48 hours at 37° C. with 5% $CO_2$. Following incubation, the medium was aspirated, and the cells were re-suspended in phosphate buffered saline (PBS) and pelleted by centrifugation at 3,000×g. The PBS was then removed and the cells were re-suspended and sonicated in 150 µL of 0.23M sucrose in PBS. 50 µL of loading buffer (200 mM Tris-Cl pH 6.8+400 mM DTT+8% SDS+40% glycerol+bromophenol blue) was applied to each sample and mixed by pipetting. The samples were incubated at room temperature for 30 minutes before being passed through a 28 gauge insulin syringe to shear co-extracted DNA. The total protein concentration of each sample was measured using the Pierce™ 660 nm Protein Assay Reagent and the Pierce Ionic Detergent Compatibility Reagent (Thermo Fisher, Waltham, MA., USA). The amount of total protein loaded in to each well (15-20 µg) was constant within each experiment. The samples were run on a 10% Mini-PROTEAN® TGX™ Precast Protein Gels (Biorad, Hercules, CA., USA) adjacent to the Li-COR Chameleon ladder (Li-Cor, Lincoln, NE, USA) and transferred to a iBlot PVDF Transfer Stack using Invitrogen's iBlot system (Invitrogen, Carlsbad, CA, USA) according to the manufacturer's instructions. Membranes were incubated with methanol for 5 minutes, washed with $diH_2O$ 3 times, and blocked for 1 hour at room temperature with Odyssey blocking buffer (Li-Cor, Lincoln, NE, USA). Membranes were then incubated with mouse anti-TurboGFP (1:2000; Origene, Rockville, MD, USA) and rabbit anti-β-tubulin (1:5000; Millipore, Burlington, MA, USA) in blocking buffer overnight at 4° C., and washed three times with 0.1% Tween20 in PBS before incubation with IRDye 800CW donkey-anti-rabbit and IRDye 680RD goat-anti-mouse (Both 1:5,000; Li-Cor, Lincoln, NE, USA) for 45 minutes at room temperature. Membranes were washed three times with 0.1% Tween20 in PBS and imaged with an Odyssey CLx system (Li-Cor, Lincoln, NE, USA). Band intensity was measured with the ImageJ software. To measure the band intensity of the predicted monomeric form of RHO-GFP, a box was drawn around the prominent band appearing at ~65 kDa whereas the aggregated forms were measured using a box drawn from the highest molecular weight marker (260 kDa) to the visible band just below 50 kDa. Band intensity of RHO was corrected for loading by measuring and dividing by the band intensity of β-tubulin. Values were reported as relative intensity, which was calculated as the corrected band intensity of each sample divided by the average corrected band intensity for the control shRNA condition. Statistical significance was determined via one-way ANOVA followed by Tukey's multiple comparisons test.

AAV Vector Preparation.

Adeno-associated virus (AAV) vectors with type 2 terminal repeats (TRs) were packaged in serotype 5 capsids as described by Zolotukhin et al. (2002).(79) AAV5 capsids permit efficient transduction of photoreceptor cells following subretinal injection.(78)

Vectors designed to knockdown human and canine rhodopsin without replacement, contained a 488 bp region (positions 916-1396) of the mouse Rho gene (GenBank M55171.2) and a humanized GFP gene cloned in reverse orientation. This orientation was used to provide a spacer for efficient packaging of AAV without over-expression of GFP. For RHO expression in the RNA replacement vectors, a 536 bp region (positions 4547-5083) from the human RHO gene (GenBank Accession number NG_009115.1) was employed as the human rhodopsin proximal promoter (hOP). The promoter was followed by a 163 synthetic intron (SD/SA) from SV40 which preceded 125 base pairs from the RHO 5' UTR the human RHO cDNA (1046 nt), or a codon-modified version ($RHO_{820}$) made resistant to $shRNA_{820}$ (see below). This was followed by a polyadenylation signal from SV40.

| Name | Target sequence | Resistant Sequence |
|---|---|---|
| $shRNA_{131}$ | CUGCCUACAUGUUUCUGCU (SEQ ID NO: 12) | N/A |
| $shRNA_{134}$ | CCUACAUGUUUCUGCUGAU (SEQ ID NO: 13) | N/A |
| $shRNA_{820}$ | GUGGCAUUCUACAUCUUCA (SEQ ID NO: 14) | GUGGCUUUUUAUAUAUUCA (SEQ ID NO: 15) |
| Rz525 | GGUGGUCCUGGC (SEQ ID NO: 16) | N/A |

The shRNA sense and antisense sequences are shown below, which in each case were connected with the loop sequence UUCAAGAGA (SEQ ID NO: 3).

| SEQ ID NO: | Name | RNA sequence |
|---|---|---|
| 21 | RHO131-Sense | CUGCCUACAUGUUUCUGCU |
| 22 | RHO131-Antisense | AGCAGAAACAUGUAGGCAG |
| 23 | RHO134-Sense | CCUACAUGUUUCUGCUGAU |
| 24 | RHO134-Antisense | AUCAGCAGAAACAUGUAGG |
| 25 | RHO765-Sense | GCAUGGUCAUCAUCAUGGU |
| 26 | RHO765-Antisense | ACCAUGAUGAUGACCAUGC |
| 1 | RHO820-Sense | GUGGCAUUCUACAUCUUCA |
| 2 | RHO820-Antisense | UGAAGAUGUAGAAUGCCAC |

AAV2/5 vectors for shRNA expression were packaged as self-complementary AAV (77) and expression of shRNAs was directed by the human H1 RNA promoter (GenBank X16612.1; nucleotides 276-378). The shRNAs contained 19 bp of double stranded sequence connected by a 9 nucleotide loop (UUCAAGAGA, encoded by the sequence TTCAAGAGA). For vectors intended for shRNA delivery without rhodopsin replacement, efficient packaging required maintenance of at least 2.2 kb of DNA between the terminal repeat sequences of AAV. In these vectors, the sequence of humanized GFP (80) was inserted in reverse orientation behind either the mouse opsin proximal promoter or the human opsin proximal promoter (see above). The vector used to express hammerhead ribozyme Rz525, pMOPS500NewHpRz525, used the mouse proximal rhodopsin promoter to drive expression of the ribozyme cassette. It is was described by Gorbatyuk et al. 2007.(33)

Both $shRNA_{820}$ and a human rhodopsin cDNA ($RHO_{820}$) made resistant to $shRNA_{820}$ by introducing silent mutations in the target sequence were packaged together as self-complementary AAV2/5. A self-complementary construct was chosen to accelerate the rate of RHO replacement (with $RHO_{820}$) in order to preserve, or rapidly reform rod outer segment structure in the context of a highly efficient KD reagent ($shRNA_{820}$).

Animals

All dogs were bred and maintained at the University of Pennsylvania Retinal Disease Studies Facility (RDSF). Studies were carried out in strict accordance with the recommendations in the Guide for the Care and Use of Laboratory Animals of the National Institutes of Health and the USDA's Animal Welfare Act and Animal Welfare Regulations, and complied with the ARVO Statement for the Use of Animals in Ophthalmic and Vision Research. The protocols were approved by the Institutional Animal Care and Use Committee of the University of Pennsylvania.

All normal (WT dogs) were housed under standard kennel cyclic (12 hours ON, 12 hours OFF) white light illumination (175-350 lux at the level of the "standard" dog eye). All RHO mutant dogs studied were heterozygous for the T4R mutant allele, and are referred to in text as RHO mutants, and as $RHO^{T4R/+}$ in Table 1 and in the figures to emphasize the heterozygosity. All but 3 mutant RHO dogs were housed under cyclic dim red illumination (9-20 lux at the level of the "standard" dog eye) from birth until termination to prevent any acceleration of retinal degeneration triggered by environmental white light. All electroretinographic and noninvasive imaging procedures, as well as subretinal injections, were performed under general anesthesia, as previously described.(44, 74, 81) Ocular tissues were collected after euthanasia with i.v. injection of euthanasia solution (Euthasol; Virbac), and all efforts were made to improve animal welfare and minimize discomfort. Included were 21 eyes from 14 normal (WT) dogs, and 40 eyes from 21 mutant RHO dogs (Table 1).

Subretinal Injections

Subretinal injections of BSS or vector were performed under direct visualization through an operating microscope (Zeiss OPMI 6; Carl Zeiss Inc, Oberkochen, Germany) and a contact vitrectomy lens using a subretinal cannula as previously reported (65) In the case of the RHO mutant dogs, dim red illumination was set up in the operating room, and subretinal injections were performed under near infrared light using an infrared bandpass filter (RT-830; Hoya Optics, Inc, Fremont, California) placed in the operating microscope's light path and monocular infrared image intensifiers (Owl Nitemare Third generation: BE Meyers & Co, Inc, Redmond, Washington) that were mounted on the two microscope eyepieces as previously described.(49) This night vision system allows the surgeon to perform subretinal injections in the light-sensitive RHO mutant dogs without causing any surgical light-induced retinal degeneration.(49) Successful subretinal injection of a ~150 uL volume produced a bleb that covered ~15% of the retinal surface. The location of the subretinal bleb was recorded immediately after each injection. This was done in normal dogs by fundus photography (Retcam shuttle, Clarity Medical Systems, Pleasanton, CA), and in RHO-mutant dogs by drawings of the bleb on near infrared cSLO composite images captured prior to the injection.

Experimental Acceleration of Retinal Disease by a Light Exposure.

An acute light exposure protocol was used as previously described (46-48) to assess the efficiency of the viral vector constructs at preventing retinal degeneration in the light sensitive RHO-mutant dog. (45) All steps of this procedure were carried out under dim red light illumination. The pupils were dilated with 1% tropicamide and 1% phenylephrine (3 times, 30 minutes apart in both eyes), and general anesthesia was induced with propofol (4 mg/kg) IV and maintained with inhalation anesthesia (isoflurane). To prevent the ventral rotation of the globe induced by the general anesthesia, a retrobulbar saline injection (5-10 ml) was performed to recenter the eyes in the primary gaze position. A one minute exposure to white (6500K) light at a corneal irradiance of 1 $mW/cm^2$ (measured with a luminometer, IL1700; International Light Technologies, Peabody, MA, USA) was performed using a monocular Ganzfeld stimulator (ColorBurst; Diagnosys LLC, Lowell, MA, USA) from an ERG system (Espion, Diagnosys LLC). Eyes that were not exposed were kept shielded with a black photographic cloth during the light exposure procedure in the contralateral eye.

In Vivo Optical Coherence Tomography (OCT) Imaging and Analyses

En face and retinal cross-sectional imaging was performed with the dogs under general inhalation anesthesia as described above. Overlapping en face images of reflectivity with near-infrared illumination (820 nm) were obtained (Spectralis HRA+October, Heidelberg, Germany) with 30° and 55° diameter lenses to delineate fundus features such as optic nerve, retinal blood vessels, boundaries of injection blebs, retinotomy sites and other local changes. Custom programs (MatLab 7.5; The MathWorks, Natick, MA) were used to digitally stitch individual photos into a retina-wide panorama. Two methods were used to overlay injection blebs onto panoramic images. In WT eyes, photos of blebs taken at the time of the surgery were registered and bleb boundaries were transferred. In RHO-mutant eyes, sketches of blebs drawn at the time of the surgery were transferred onto panoramic images.

Spectral-domain optical coherence tomography (SD-OCT) was performed with linear and raster scans (Spectralis HRA+October, Heidelberg, Germany). Overlapping (30°× 20°) raster scans were recorded covering large regions of the retina. Post-acquisition processing of OCT data was performed with custom programs (MatLab 7.5; The Math Works, Natick, MA). For retina-wide topographic analysis, integrated backscatter intensity of each raster scan was used to locate its precise location and orientation relative to retinal features visible on the retina-wide panorama. Individual longitudinal reflectivity profiles (LRPs) forming all registered raster scans were allotted to regularly spaced bins (1°×1°) in a rectangular coordinate system centered at the optic nerve; LRPs in each bin were aligned and averaged. Intensity and slope information of the backscatter signal along each LRP was manually evaluated to segment two boundaries that define the ONL. One boundary was the distal transition of the outer plexiform layer (OPL) peak. The other boundary was the external limiting membrane (ELM) peak. In locations with severe retinal degeneration without a detectable ELM peak, the second ONL boundary was placed at the most proximal transition to the RPE peak. In addition, the normalized IS/OS backscatter intensity was calculated by subtracting the mean backscatter intensity of the 5 axial samples vitreal to the OPL boundary from the mean backscatter intensity of the 5 axial samples scleral to the ELM boundary; the latter included the IS/OS peak.(44, 74) IS/OS intensities were only mapped in regions of retained inner and outer segment length since compromise of the latter made it impossible to distinguish the IS/OS signal from the RPE/tapetum signal. Topographic results from uninjected control eyes were registered by the center of the ONH and the canine fovea (83) and maps of control variability were generated defining the 99th percentile confidence intervals. Injected eyes were compared locus-by-locus to the control confidence intervals to generate maps of significant change.

Electroretinography (ERG) Recording and Analyses

Dogs were pre-medicated with subcutaneous injections of atropine, and acepromazine, and their pupils dilated with atropine (1%), tropicamide (1%) and phenylephrine (10%). After induction with intravenous propofol, dogs were maintained under general inhalation anesthesia (isoflurane), and their pulse rate, oxygen saturation and temperature was monitored for constancy during the entire procedure. Full-field flash electroretinography was performed as previously described (44, 74) on both eyes using a custom-built Ganzfeld dome fitted with the LED stimuli of a ColorDome stimulator (Diagnosys LLC, Lowell, MA). After 20 minutes of dark adaptation, rod and mixed rod-cone-mediated responses (averaged 4 times) to single 4 ms white flash stimuli of increasing intensities (from −3.74 to 0.51 log $cd \cdot s \cdot m^{-2}$) were recorded. Following 5 minutes of white light adaptation (1.53 log $cd \cdot m^{-2}$), cone-mediated signals (averaged 10 times) to a series of single flashes (from −2.74 to 0.51 log $cd \cdot s \cdot m^{-2}$) and to a 29.4-Hz flicker (averaged 20 times; from −2.74 to 0.26 log $cd \cdot s \cdot m^{-2}$) stimuli were recorded. Waveforms were processed with a digital low-pass (50 Hz) filter to reduce recording noise if necessary. Amplitudes of the a- and b-waves of the scotopic mixed rod-cone ERG, and the peak to peak amplitudes of the photopic single flash and 29.4 Hz cone flicker were measured.

Retinal Histology and Immunohistochemistry

Following euthanasia and enucleation, the globes were fixed in 4% paraformaldehyde (PFA) for 3 hours followed by 2% PFA for 24 hours, trimmed, cryoprotected in 15-30% sucrose/PBS solution, and embedded in optimal cutting temperature media as previously reported (81). Ten-micrometer-thick serial sections that encompassed the nontreated, the boundary, and the treated/bleb area were cut on a cryostat (Microm HM550; Thermo Fisher Scientific, Kalamazoo, MI). Blood vessel landmarks identified by H&E staining were used to determine the precise location of the retinal cryosections on the vascular pattern of the en face cSLO images, as previously reported. (44, 74, 81) Sequential sections were immunolabeled with primary antibodies and cell-specific markers: rod opsin (cat #MAB5316; 1:200 dilution; EMD Millipore, Billerica, MA), goat anti-human cone arrestin (W. Beltran, Univ. of Pennsylvania; 1:100). The antigen-antibody complexes were visualized with fluorochrome-labeled secondary antibodies (Alexa Fluor, 1:200; Molecular Probes, Kalamazoo, MI), and Hoechst 33342 nuclear stain (Molecular Probes) was used to label cell nuclei. H&E-stained sections were examined by widefield microscopy (Axioplan; Carl Zeiss Meditec, Dublin, CA), and the images were digitally captured (Spot 4.0 camera; Diagnostic Instruments, Sterling Heights, MI) and imported into a graphics program (Illustrator; Adobe, San Jose, CA) for display. Sections labeled for fluorescent immunohistochemistry were examined by confocal microscopy (Leica TCS SP5; Leica Microsystems, Buffalo Grove, IL), and digital images were taken, processed using the Leica Application suite program, and imported into a graphics program (Illustrator; Adobe).

Retinal Tissue Sampling for RHO RNA and Protein Quantification

Immediately following enucleation and separation of the posterior cup, 3 mm biopsy punches from treated and untreated neuroretinal areas were individually collected in cryovials, frozen in liquid nitrogen and stored at −80° C. For RHO mutant dogs retinal sampling was performed under dim red illumination.

RNA Extraction and cDNA Synthesis

Total RNA was extracted from the punches of neuroretina using Direct-zol RNA Miniprep Kit (Zymo Research, Irvine, CA). cDNA was prepared from total RNA using the High Capacity RNA to cDNA kit (Applied Biosystems, Foster City, CA) following the manufacturer's recommendations.

Absolute Quantification of Canine and Human RHO Transcripts in Retina

To efficiently determine the ratio between endogenous canine and exogenous human RHO transcripts in the same retinal samples specific primer pairs have been designed for canine (For: 5'-ACAAGACGGGTGTGGTGCGC (SEQ ID NO: 17); Rev: 5'-TCATGGGCGTCGCCTTCACC (SEQ ID NO: 18)) and human RHO (For: 5'-CCATCAACTTCCT-CACGCTCTA (SEQ ID NO: 19); Rev: 5'-TAGGTT-GAGCAGGATGTAGTTGAGA (SEQ ID NO: 20)). The SYBR green platform was used for the analysis using a primer concentration of 0.15 μM. Real-time PCR was performed in a total volume of 25 μL in 96-well microwell plates on the Applied Biosystems 7500 Real-Time PCR System. All PCRs were performed using cDNA generated from 0.1 ng DNAase-treated RNA. The RT-PCR product was used for construction of an absolute standard curve for individual amplicons representing the canine and human RHO. The number of copies of a template was calculated as previously described.(82) The dynamic range of the calibration curves was between $10^3$ and $10^7$ molecules. Amplification data were analyzed with the 7500 Software version 2.0.1 (Applied Biosystems).

Quantification of Rhodopsin Protein:

Protein retinal extracts were prepared from 3 mm biopsy punches collected (under dim red illumination for RHO mutant dogs) from treated and untreated neuroretinal areas. After sonication in a buffer containing 0.23M Sucrose, 2 mM EDTA, 5 mM TrisHCl, pH 7.4, and protease inhibitors (Halt Protease Inhibitor cocktail, cat. No. 87786, Thermo Fisher Scientific, Waltham, MA.), samples were centrifuged and total protein concentration in the supernatant was measured by the Bradford method. One μg of total protein from each sample was resolved on 8-16% Tris Glycine gel (Invitrogen, Carlsbad, CA), transferred to a nitrocellulose membrane (iBLOT, Invitrogen) and immunoblotted using anti-Rhodopsin antibody (MAB5316, 1:1000 dilution, EMD Millipore, Billerica, MA) and anti-Histone H3 antibody (ab1791, 1:3000 dilution, Abcam, Cambridge, MA). Protein bands were visualized on a digital imaging system (Odyssey Fc, Licor, Lincoln, NE) after incubation with infrared labeled secondary antibodies (IRDye 680 and IRDye 800, Licor). Amounts of Rhodopsin protein were quantified with the Licor Image Studio v4.0 software using the histone H3 band for normalization.

REFERENCES

1. Ginn S L, Alexander I E, Edelstein M L, Abedi M R, & Wixon J (2013) Gene therapy clinical trials worldwide to 2012—an update. J Gene Med 15(2):65-77.
2. Dunbar C E, et al. (2018) Gene therapy comes of age. Science 359(6372).
3. Ferrua F & Aiuti A (2017) Twenty-Five Years of Gene Therapy for ADA-SCID: From Bubble Babies to an Approved Drug. Hum Gene Ther 28(11):972-981.
4. Kumar S R, Markusic D M, Biswas M, High K A, & Herzog R W (2016) Clinical development of gene therapy: results and lessons from recent successes. Molecular therapy. Methods & clinical development 3:16034.
5. Mao H, et al. (2011) AAV Delivery of Wild-Type Rhodopsin Preserves Retinal Function in a Mouse Model of Autosomal Dominant Retinitis Pigmentosa. Hum Gene Ther 22(5):567-575.
6. Stanton C M, et al. (2017) Novel pathogenic mutations in C1QTNF5 support a dominant negative disease mechanism in late-onset retinal degeneration. Scientific reports 7(1):12147.
7. Lewin A S, Glazer P M, & Milstone L M (2005) Gene therapy for autosomal dominant disorders of keratin. The journal of investigative dermatology. Symposium proceedings 10(1):47-61.
8. Miller T M, et al. (2013) An antisense oligonucleotide against SOD1 delivered intrathecally for patients with SOD1 familial amyotrophic lateral sclerosis: a phase 1, randomised, first-in-man study. The Lancet. Neurology 12(5):435-442.
9. Bennett J (2017) Taking Stock of Retinal Gene Therapy: Looking Back and Moving Forward. Mol Ther 25(5): 1076-1094.
10. Hartong D T, Berson E L, & Dryja T P (2006) Retinitis pigmentosa. Lancet 368(9549):1795-1809.
11. Sung C H, et al. (1991) Rhodopsin mutations in autosomal dominant retinitis pigmentosa. Proc Natl Acad Sci USA 88(15):6481-6485.
12. Inglehearn C F, et al. (1992) A completed screen for mutations of the rhodopsin gene in a panel of patients with autosomal dominant retinitis pigmentosa. Hum Mol Genet 1(1):41-45.
13. Sullivan L S, et al. (2006) Prevalence of disease-causing mutations in families with autosomal dominant retinitis pigmentosa: a screen of known genes in 200 families. Invest Ophthalmol Vis Sci 47(7):3052-3064.
14. Sullivan L S, et al. (2013) Prevalence of Mutations in eyeGENE Probands With a Diagnosis of Autosomal Dominant Retinitis Pigmentosa. Invest Ophthalmol Vis Sci 54(9):6255-6261.
15. Athanasiou D, et al. (2018) The molecular and cellular basis of rhodopsin retinitis pigmentosa reveals potential strategies for therapy. Prog Retin Eye Res 62:1-23.
16. Sung C H, Davenport C M, & Nathans J (1993) Rhodopsin mutations responsible for autosomal dominant retinitis pigmentosa. Clustering of functional classes along the polypeptide chain. J Biol Chem 268(35):26645-26649.
17. Jacobson S G, Kemp C M, Sung C H, & Nathans J (1991) Retinal function and rhodopsin levels in autosomal dominant retinitis pigmentosa with rhodopsin mutations. Am J Ophthalmol 112(3):256-271.
18. Jacobson S G, et al. (1994) Phenotypes of stop codon and splice site rhodopsin mutations causing retinitis pigmentosa. Invest Ophthalmol Vis Sci 35(5):2521-2534.
19. Cideciyan A V, et al. (1998) Disease sequence from mutant rhodopsin allele to rod and cone photoreceptor degeneration in man. Proc Natl Acad Sci USA 95(12): 7103-7108.
20. Jacobson S G, et al. (2016) Complexity of the Class B Phenotype in Autosomal Dominant Retinitis Pigmentosa Due to Rhodopsin Mutations. Invest Ophthalmol Vis Sci 57(11):4847-4858.
21. Drenser K A, Timmers A M, Hauswirth W W, & Lewin A S (1998) Ribozyme-targeted destruction of RNA associated with autosomal-dominant retinitis pigmentosa. Invest Ophthalmol Vis Sci 39(5):681-689.
22. Lewin A S, et al. (1998) Ribozyme rescue of photoreceptor cells in a transgenic rat model of autosomal dominant retinitis pigmentosa. Nat Med 4(8):967-971.
23. LaVail M M, et al. (2000) Ribozyme rescue of photoreceptor cells in P23H transgenic rats: long-term survival and late-stage therapy. Proc Natl Acad Sci USA 97(21): 11488-11493.
24. Shaw L C, et al. (2001) An allele-specific hammerhead ribozyme gene therapy for a porcine model of autosomal dominant retinitis pigmentosa. Mol Vis 7:6-13.
25. Tessitore A, et al. (2006) Preferential silencing of a common dominant rhodopsin mutation does not inhibit retinal degeneration in a transgenic model. Mol Ther 14(5):692-699.
26. Murray S F, et al. (2015) Allele-Specific Inhibition of Rhodopsin With an Antisense Oligonucleotide Slows Photoreceptor Cell Degeneration. Invest Ophthalmol Vis Sci 56(11):6362-6375.
27. Bakondi B, et al. (2016) In Vivo CRISPR/Cas9 Gene Editing Corrects Retinal Dystrophy in the S334ter-3 Rat Model of Autosomal Dominant Retinitis Pigmentosa. Mol Ther 24(3):556-563.
28. Burnight E R, et al. (2017) Using CRISPR-Cas9 to Generate Gene-Corrected Autologous iPSCs for the Treatment of Inherited Retinal Degeneration. Mol Ther 25(9):1999-2013.
29. Millington-Ward S, et al. (1997) Strategems in vitro for gene therapies directed to dominant mutations. Hum Mol Genet 6(9):1415-1426.
30. O'Neill B, et al. (2000) Ribozyme-based therapeutic approaches for autosomal dominant retinitis pigmentosa. Invest Ophthalmol Vis Sci 41(10):2863-2869.
31. Sullivan J M, Pietras K M, Shin B J, & Misasi J N (2002) Hammerhead ribozymes designed to cleave all human rod opsin mRNAs which cause autosomal dominant retinitis pigmentosa. Mol Vis 8:102-113.
32. Gorbatyuk M S, Pang J J, Thomas J, Jr., Hauswirth W W, & Lewin A S (2005) Knockdown of wild-type mouse rhodopsin using an AAV vectored ribozyme as part of an RNA replacement approach. Mol Vis 11:648-656.
33. Gorbatyuk M, Justilien V, Liu J, Hauswirth W W, & Lewin A S (2007) Preservation of photoreceptor morphology and function in P23H rats using an allele independent ribozyme. Exp Eye Res 84(1):44-52.
34. Gorbatyuk M, Justilien V, Liu J, Hauswirth W W, & Lewin A S (2007) Suppression of mouse rhodopsin expression in vivo by AAV mediated siRNA delivery. Vision Res 47(9):1202-1208.
35. O'Reilly M, et al. (2008) A transgenic mouse model for gene therapy of rhodopsin-linked Retinitis Pigmentosa. Vision Res 48(3):386-391.
36. Chadderton N, et al. (2009) Improved Retinal Function in a Mouse Model of Dominant Retinitis Pigmentosa Following AAV-delivered Gene Therapy. Mol Ther 17(4): 593-599.
37. Abdelmaksoud H E, Yau E H, Zuker M, & Sullivan J M (2009) Development of lead hammer-head ribozyme candidates against human rod opsin mRNA for retinal degeneration therapy. Exp Eye Res 88(5):859-879.
38. Mussolino C, et al. (2011) Zinc-finger-based transcriptional repression of rhodopsin in a model of dominant retinitis pigmentosa. EMBO molecular medicine 3(3): 118-128.
39. Latella M C, et al. (2016) In vivo Editing of the Human Mutant Rhodopsin Gene by Electroporation of Plasmid-based CRISPR/Cas9 in the Mouse Retina. Molecular therapy. Nucleic acids 5(11):e389.

40. Kiang A S, et al. (2005) Toward a gene therapy for dominant disease: validation of an RNA interference-based mutation-independent approach. Mol Ther 12(3): 555-561.
41. O'Reilly M, et al. (2007) RNA interference-mediated suppression and replacement of human rhodopsin in vivo. Am J Hum Genet 81(1):127-135.
42. Millington-Ward S, et al. (2011) Suppression and Replacement Gene Therapy for Autosomal Dominant Disease in a Murine Model of Dominant Retinitis Pigmentosa. Mol Ther 19(4):642-649.
43. Mao H, Gorbatyuk M S, Rossmiller B, Hauswirth W W, & Lewin A S (2012) Long-term rescue of retinal structure and function by rhodopsin RNA replacement with a single adeno-associated viral vector in P23H RHO transgenic mice. Hum Gene Ther 23(4):356-366.
44. Beltran W A, et al. (2017) Optimization of Retinal Gene Therapy for X-Linked Retinitis Pigmentosa Due to RPGR Mutations. Mol Ther 25(8):1866-1880.
45. Cideciyan A V, et al. (2005) In vivo dynamics of retinal injury and repair in the rhodopsin mutant dog model of human retinitis pigmentosa. Proc Natl Acad Sci USA 102(14):5233-5238.
46. Marsili S, et al. (2015) Exclusion of the Unfolded Protein Response in Light-Induced Retinal Degeneration in the Canine T4R RHO Model of Autosomal Dominant Retinitis Pigmentosa. PLOS ONE 10(2):e0115723.
47. Iwabe S, Ying G S, Aguirre G D, & Beltran W A (2016) Assessment of visual function and retinal structure following acute light exposure in the light sensitive T4R rhodopsin mutant dog. Exp Eye Res 146:341-353.
48. Sudharsan R, Simone K M, Anderson N P, Aguirre G D, & Beltran W A (2017) Acute and Protracted Cell Death in Light-Induced Retinal Degeneration in the Canine Model of Rhodopsin Autosomal Dominant Retinitis Pigmentosa. Invest Ophthalmol Vis Sci 58(1):270-281.
49. Komaromy A M, Acland G M, & Aguirre G D (2008) Operating in the dark: a night-vision system for surgery in retinas susceptible to light damage. Arch Ophthalmol 126(5):714-717.
50. Pelletier R, Caron S O, & Puymirat J (2006) RNA based gene therapy for dominantly inherited diseases. Curr Gene Ther 6(1):131-146.
51. Palfi A, et al. (2006) RNAi-based suppression and replacement of rds-peripherin in retinal organotypic culture. Hum Mutat 27(3):260-268.
52. Mueller C, et al. (2012) Sustained miRNA-mediated knockdown of mutant AAT with simultaneous augmentation of wild-type AAT has minimal effect on global liver miRNA profiles. Mol Ther 20(3):590-600.
53. Conley S M & Naash M I (2014) Gene therapy for PRPH2-associated ocular disease: challenges and prospects. Cold Spring Harbor perspectives in medicine 4(11): a017376.
54. Botta S, et al. (2016) Rhodopsin targeted transcriptional silencing by DNA-binding. eLife 5:e12242.
55. Sakami S, et al. (2011) Probing mechanisms of photoreceptor degeneration in a new mouse model of the common form of autosomal dominant retinitis pigmentosa due to P23H opsin mutations. J Biol Chem 286(12): 10551-10567.
56. Kijas J W, et al. (2002) Naturally occurring rhodopsin mutation in the dog causes retinal dysfunction and degeneration mimicking human dominant retinitis pigmentosa. Proc Natl Acad Sci USA 99(9):6328-6333.
57. Zhu L, et al. (2004) A naturally occurring mutation of the opsin gene (T4R) in dogs affects glycosylation and stability of the G protein-coupled receptor. J Biol Chem 279(51):53828-53839.
58. Heckenlively J R, Rodriguez J A, & Daiger S P (1991) Autosomal dominant sectoral retinitis pigmentosa. Two families with transversion mutation in codon 23 of rhodopsin. Arch Ophthalmol 109(1):84-91.
59. Iannaccone A, et al. (2006) Retinitis pigmentosa associated with rhodopsin mutations: Correlation between phenotypic variability and molecular effects. Vision Res. 46(27):4556-4567.
60. Paskowitz D M, LaVail M M, & Duncan J L (2006) Light and inherited retinal degeneration. Br J Ophthalmol 90(8): 1060-1066.
61. Sakami S, Kolesnikov A V, Kefalov V J, & Palczewski K (2014) P23H opsin knock-in mice reveal a novel step in retinal rod disc morphogenesis. Hum Mol Genet 23(7): 1723-1741.
62. Haeri M & Knox B E (2012) Rhodopsin mutant P23H destabilizes rod photoreceptor disk membranes. PLOS ONE 7(1):e30101.
63. White D A, Fritz J J, Hauswirth W W, Kaushal S, & Lewin A S (2007) Increased sensitivity to light-induced damage in a mouse model of autosomal dominant retinal disease. Invest Ophthalmol Vis Sci 48(5):1942-1951.
64. Tam B M & Moritz O L (2009) The role of rhodopsin glycosylation in protein folding, trafficking, and light-sensitive retinal degeneration. J Neurosci 29(48):15145-15154.
65. Beltran W A, et al. (2010) rAAV2/5 gene-targeting to rods: dose-dependent efficiency and complications associated with different promoters. Gene Ther 17(9):1162-1174.
66. Komaromy A M, et al. (2013) Transient photoreceptor deconstruction by CNTF enhances rAAV-mediated cone functional rescue in late stage CNGB3-achromatopsia. Mol Ther 21(6):1131-1141.
67. Olsson J E, et al. (1992) Transgenic mice with a rhodopsin mutation (Pro23His): a mouse model of autosomal dominant retinitis pigmentosa. Neuron 9(5):815-830.
68. Tan E, et al. (2001) The relationship between opsin overexpression and photoreceptor degeneration. Invest Ophthalmol Vis Sci 42(3):589-600.
69. Dittmar K A, Goodenbour J M, & Pan T (2006) Tissue-specific differences in human transfer RNA expression. PLOS genetics 2(12):e221.
70. Gardin J, et al. (2014) Measurement of average decoding rates of the 61 sense codons in vivo. eLife 3.
71. Trochet D, Prudhon B, Vassilopoulos S, & Bitoun M (2015) Therapy for dominant inherited diseases by allele-specific RNA interference: successes and pitfalls. Curr Gene Ther 15(5):503-510.
72. Myslinski E, Ame J C, Krol A, & Carbon P (2001) An unusually compact external promoter for RNA polymerase III transcription of the human H1RNA gene. Nucleic acids research 29(12):2502-2509.
73. Wu M T, et al. (2005) Simple and efficient DNA vector-based RNAi systems in mammalian cells. Biochem Biophys Res Commun 330(1):53-59.
74. Beltran W A, et al. (2015) Successful arrest of photoreceptor and vision loss expands the therapeutic window of retinal gene therapy to later stages of disease. Proc Natl Acad Sci USA 112(43):E5844-5853.
75. Guziewicz K E, et al. (2018) BEST1 gene therapy corrects a diffuse retina-wide micro-detachment modulated by light exposure. Proc Natl Acad Sci USA In Press: DOI 10.107-3/pnas.1720662115.
76. Kunte M M, et al. (2012) ER Stress Is Involved in T17M Rhodopsin-Induced Retinal Degeneration. Invest Ophthalmol Vis Sci 53(7):3792-3800.
77. McCarty D M, Monahan P E, & Samulski R J (2001) Self-complementary recombinant adeno-associated virus (scAAV) vectors promote efficient transduction independently of DNA synthesis. Gene Ther 8(16):1248-1254.
78. Auricchio A, et al. (2001) Exchange of surface proteins impacts on viral vector cellular specificity and transduction characteristics: the retina as a model. Hum Mol Genet 10(26):3075-3081.
79. Zolotukhin S, et al. (2002) Production and purification of serotype 1, 2, and 5 recombinant adeno-associated viral vectors. Methods 28(2):158-167.
80. Zolotukhin S, Potter M, Hauswirth W W, Guy J, & Muzyczka N (1996) A "humanized" green fluorescent protein cDNA adapted for high-level expression in mammalian cells. J Virol 70(7):4646-4654.
81. Beltran W A, et al. (2012) Gene therapy rescues X-linked photoreceptor blindness in dogs and paves the way for treating RPGR form of human retinitis pigmentosa. Proc Natl Acad Sci USA 109(6):2132-2137.
82. Kuznetsova T, Zangerl B, Goldstein O, Acland G M, & Aguirre G D (2011) Structural organization and expression pattern of the canine RPGRIP1 isoforms in retinal tissue. Invest. Ophthalmol. Vis Sci. 52(6):2989-2998.
83. Beltran W A, et al. (2014) Canine retina has a primate fovea-like bouquet of cone photoreceptors which is affected by inherited macular degenerations. PLOS ONE 9(3):e90390.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A short hairpin RNA (shRNA) comprising the nucleotide sequence: GUGGCAUUCUACAUCUUCAUU-CAAGAGAUGAAGAUGUAGAAUGCCAC (SEQ ID NO: 4).

2. A vector encoding the shRNA of claim 1.

3. The vector of claim 2, further comprising a recombinant rhodopsin (RHO) coding sequence that does not contain a sequence targeted by the shRNA.

4. The vector of claim 3, wherein the recombinant RHO coding sequence is codon-optimized for expression in a human cell.

5. The vector of claim 3, wherein the recombinant RHO coding sequence comprises a nucleotide sequence that is at least 95% identical to the nucleotide sequence of SEQ ID NO: 5.

6. The vector of claim 5, wherein the recombinant RHO coding sequence comprises the nucleotide sequence of SEQ ID NO: 5.

7. The vector of claim 3, further comprising an opsin proximal promoter.

8. The vector of claim 7, wherein the opsin proximal promoter comprises the nucleotide sequence of SEQ ID NO: 7.

9. The vector of claim 2, wherein the vector is a plasmid.

10. The vector of claim 2, wherein the vector is a recombinant adeno-associated viral (rAAV) vector.

11. The vector of claim 10, wherein the rAAV vector is self-complementary.

12. The vector of claim 2, further comprising an H1 RNA promoter.

13. The vector of claim 12, wherein the H1 RNA promoter comprises the nucleotide sequence of SEQ ID NO: 8.

14. A recombinant adeno-associated viral (rAAV) particle comprising the rAAV vector of claim 10.

15. A composition comprising the rAAV particle of claim 14 and a pharmaceutically acceptable carrier.

16. A method of modulating RHO expression in a subject, the method comprising administering subretinally to the subject the composition of claim 15.

17. A method of treating retinitis pigmentosa in a subject, the method comprising administering subretinally to the subject the composition of claim 15.

18. The method of claim 17, wherein the subject is a human subject.

19. A vector comprising a nucleotide sequence that is at least 90% identical to the nucleotide sequence of SEQ ID NO: 6.

20. The vector of claim 19, wherein the vector comprises the nucleotide sequence of SEQ ID NO: 6.

* * * * *

SEQUENCE LISTING

```
<160> NUMBER OF SEQ ID NOS: 47

<210> SEQ ID NO 1
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1
guggcauucu acaucuuca                                                  19

<210> SEQ ID NO 2
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 2
ugaagaugua gaaugccac                                                  19

<210> SEQ ID NO 3
<211> LENGTH: 9
<212> TYPE: RNA
<213> ORGANISM: Artificial Sequence
<220> FEATURE:
<223> OTHER INFORMATION: Synthetic Polynucleotide

<400> SEQUENCE: 3 uucaagaga                                                              9

<210> SEQ ID NO 4
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 4
guggcauucu acaucuucau ucaagagaug aagauguaga augccac                   47

<210> SEQ ID NO 5
<211> LENGTH: 1047
<212> TYPE: DNA
<213> ORGANISM: Artificial Sequence
```

```
<220> FEATURE:
<223> OTHER INFORMATION: Synthetic Polynucleotide

<400> SEQUENCE: 5
atgaatggca cagaaggccc taacttctac gtgcccttct ccaatgcgac gggtgtggta      60
cgcagcccct tcgagtaccc acagtactac ctggctgagc catggcagtt ctccatgctg     120
gccgcctaca tgtttctgct gatcgtgctg ggcttcccca tcaacttcct cacgctctac     180
gtcaccgtcc agcacaagaa gctgcgcacg cctctcaact acatcctgct caacctagcc     240
gtggctgacc tcttcatggt cctaggtggc ttcaccagca ccctctacac ctctctgcat     300
ggatacttcg tcttcgggcc cacaggatgc aatttggagg gcttctttgc caccctgggc     360
ggtgaaattg ccctgtggtc cttggtggtc ctggccatcg agcggtacgt ggtggtgtgt     420
aagcccatga gcaacttccg cttcggggag aaccatgcca tcatgggcgt tgccttcacc     480
tgggtcatgg cgctggcctg cgccgcaccc ccactcgccg gctggtccag gtacatcccc     540
gagggcctgc agtgctcgtg tggaatcgac tactacacgc tcaagccgga ggtcaacaac     600
gagtcttttg tcatctacat gttcgtggtc cacttcacca tccccatgat tatcatcttt     660
ttctgctatg gcagctcgt cttcaccgtc aaggaggccg ctgcccagca gcaggagtca     720
gccaccacac agaaggcaga gaaggaggtc acccgcatgg tcatcatcat ggtcatcgct     780
ttcctgatct gctgggtgcc ctacgccagc gtggcttttt atatattcac ccaccagggc     840
tccaacttcg gtcccatctt catgaccatc ccagcgttct tgccaagag cgccgccatc     900
tacaaccctg tcatctatat catgatgaac aagcagttcc ggaactgcat gctcaccacc     960
atctgctgcg gcaagaaccc actgggtgac gatgaggcct ctgctaccgt gtccaagacg    1020
gagacgagcc aggtggcccc ggcctaa                                         1047

<210> SEQ ID NO 6
<211> LENGTH: 6562
<212> TYPE: DNA
<213> ORGANISM: Artificial Sequence
<220> FEATURE:
<223> OTHER INFORMATION: Synthetic Polynucleotide

<400> SEQUENCE: 6
cgctcgctcg ctcactgagg ccgcccgggc aaagcccggg cgtcgggcga cctttggtcg      60
cccggcctca gtgagcgagc gagcgcgcag agagggagtg gccaactcca tcactagggg     120
ttccttgtag ttaatgatta acccgccatg ctacttatct acgtagccat gctctaggat     180
ctgaattcgg taccccctcat ggagctcctc ctgtcagagg agtgtgggga ctggatgact     240
ccagaggtaa cttgtggggg aacgaacagg taaggggctg tgtgacgaga tgagagactg     300
ggagaataaa ccagaaagtc tctagctgtc cagaggacat agcacagagg cccatggtcc     360
ctatttcaaa cccaggccac cagactgagc tgggaccttg gacagacaa gtcatgcaga     420
agttagggga cctctctcc ccttttcctg gatcctgagt acctctcctc cctgacctca     480
ggcttcctcc tagtgtcacc ttggcccctc ttagaagcca attaggccct cagtttctgc     540
agcggggatt aatatgatta tgaacacccc caatctccca gatgctgatt cagccaggag     600
cttaggaggg ggaggtcact ttataagggt ctggggggg cagaacccag agtcatccag     660
ctggagccct gagtggctga gctcaggcct tcgcagcatt cttgggtggg agcagccacg     720
ggtcagccac atctagagga tccggtactc gaggaactga aaaccagaa agttaactgg     780
taagtttagt ctttttgtct tttatttcag gtcccggatc cggtggtggt gcaaatcaaa     840
```

```
gaactgctcc tcagtggatg ttgcctttac ttctaggcct gtacggaagt gttacttctg      900
ctctaaaagc tgcggaattg tacccgcggc cgcccagctg gagccctgag tggctgagct      960
caggccttcg cagcattctt gggtgggagc agccacgggt cagccacaag gccacagcc     1020 atgaatggca cagaaggccc taacttctac gtgcccttct ccaatgcgac gggtgtggta     1080
cgcagcccct tcgagtaccc acagtactac ctggctgagc catggcagtt ctccatgctg     1140
gccgcctaca tgtttctgct gatcgtgctg ggcttcccca tcaacttcct cacgctctac     1200
gtcaccgtcc agcacaagaa gctgcgcacg cctctcaact acatcctgct caacctagcc     1260
gtggctgacc tcttcatggt cctaggtggc ttcaccagca ccctctacac ctctctgcat     1320
ggatacttcg tcttcgggcc cacaggatgc aatttggagg gcttctttgc caccctgggc     1380
ggtgaaattg ccctgtggtc cttggtggtc ctggccatcg agcggtacgt ggtggtgtgt     1440
aagcccatga gcaacttccg cttcggggag aaccatgcca tcatgggcgt tgccttcacc     1500
tgggtcatgg cgctggcctg cgccgcaccc ccactcgccg gctggtccag gtacatcccc     1560
gagggcctgc agtgctcgtg tggaatcgac tactacacgc tcaagccgga ggtcaacaac     1620 gagtctttg tcatctacat gttcgtggtc cacttcacca tccccatgat tatcatcttt     1680
ttctgctatg ggcagctcgt cttcaccgtc aaggaggccg ctgcccagca gcaggagtca     1740
gccaccacac agaaggcaga gaaggaggtc acccgcatgg tcatcatcat ggtcatcgct     1800
ttcctgatct gctgggtgcc ctacgccagc gtggcttttt atatattcac ccaccagggc     1860
tccaacttcg gtcccatctt catgaccatc ccagcgttct tgccaagag cgccgccatc     1920 tacaaccctg tcatctatat catgatgaac aagcagttcc ggaactgcat gctcaccacc     1980
atctgctgcg gcaagaaccc actgggtgac gatgaggcct ctgctaccgt gtccaagacg     2040
gagacgagcc aggtggcccc ggcctaagac ctgcctagga ctctgtggcc gactataggc     2100
gtctcccatc ccctacacct tcccccagcc acagccatcc caccaggcgg ccgcggggat     2160
ccagacatga taagatacat tgatgagttt ggacaaacca caactagaat gcagtgaaaa     2220
aaatgcttta tttgtgaaat ttgtgatgct attgctttat tgtaaccat tataagctgc     2280 aataaacaag ttaacaacaa caattgcatt catttatgt ttcaggttca ggggaggtg      2340 tgggaggttt tttagtcgac taaaacgacg gccagtgaat tcatatttgc atgtcgctat     2400
gtgttctggg aaatcaccat aaacgtgaaa tgtctttgga tttgggaatc ttataagttc     2460
tgtatgagac cactcggatc cgtggcattc tacatcttca ttcaagagat gaagatgtag     2520
aatgccactt tttaagcttt ttggcgtaat catggtcgac attggatcgg atcccgggcc     2580
cgtcgactag agctcgctga tcagcctcga ctgtgccttc tagttgccag ccatctgttg     2640 tttgccccctc ccccgtgcct tccttgaccc tggaaggtgc cactcccact gtcctttcct     2700
aataaaatga ggaaattgca tcgcattgtc tgagtaggtg tcattctatt ctgggggggtg     2760 gggtggggca ggacagcaag ggggaggatt gggaagacaa tagcaggaac cccactccct     2820
ctctgcgcgc tcgctcgctc actgaggccg ggcgaccaaa ggtcgcccga cgcccgggct     2880
ttgcccgggc ggcctcagtg agcgagcgag cgcgcagctg ctgcattaat gaatcggcca     2940
acgcgcgggg agaggcggtt tgcgtattgg gcgctcttcc gcttcctcgc tcactgactc     3000
gctgcgctcg tcgttcggc tgcggcgagc ggtatcagct cactcaaagg cggtaatacg     3060
gttatccaca gaatcagggg ataacgcagg aaagaacatg tgagcaaaag gccagcaaaa     3120
ggccaggaac cgtaaaaagg ccgcgttgct ggcgttttt cataggctcc gcccccctga     3180
cgagcatcac aaaaatcgac gctcaagtca gaggtggcga acccgacag gactataaag     3240
```

```
ataccaggcg tttccccctg gaagctccct cgtgcgctct cctgttccga ccctgccgct    3300
taccggatac ctgtccgcct ttctcccttc gggaagcgtg gcgctttctc atagctcacg    3360
ctgtaggtat ctcagttcgg tgtaggtcgt tcgctccaag ctgggctgtg tgcacgaacc    3420
ccccgttcag cccgaccgct gcgccttatc cggtaactat cgtcttgagt ccaacccggt    3480
aagacacgac ttatcgccac tggcagcagc cactggtaac aggattagca gagcgaggta    3540
tgtaggcggt gctacagagt tcttgaagtg gtggcctaac tacggctaca ctagaaggac    3600
agtatttggt atctgcgctc tgctgaagcc agttaccttc ggaaaaagag ttggtagctc    3660
ttgatccggc aaacaaacca ccgctggtag cggtggtttt tttgtttgca agcagcagat    3720
tacgcgcaga aaaaaggat ctcaagaaga tcctttgatc ttttctacgg gtctgacgc    3780 tcagtggaac gaaaactcac gttaagggat tttggtcatg agattatcaa aaaggatctt    3840
cacctagatc cttttaaatt aaaaatgaag ttttaaatca atctaaagta tatatgagta    3900
aacttggtct gacagttacc aatgcttaat cagtgaggca cctatctcag cgatctgtct    3960
atttcgttca tccatagttg cctgactccc cgtcgtgtag ataactacga tacgggaggg    4020
cttaccatct ggccccagtg ctgcaatgat accgcgagac ccacgctcac cggctccaga    4080
tttatcagca ataaaccagc cagccggaag ggccgagcgc agaagtggtc ctgcaacttt    4140
atccgcctcc atccagtcta ttaattgttg ccgggaagct agagtaagta gttcgccagt    4200
taatagtttg cgcaacgttg ttgccattgc tacaggcatc gtggtgtcac gctcgtcgtt    4260
tggtatggct tcattcagct ccggttccca acgatcaagg cgagttacat gatccccat    4320 gttgtgcaaa aaagcggtta gctccttcgg tcctccgatc gttgtcagaa gtaagttggc    4380
cgcagtgtta tcactcatgg ttatggcagc actgcataat tctcttactg tcatgccatc    4440
cgtaagatgc ttttctgtga ctggtgagta ctcaaccaag tcattctgag aatagtgtat    4500
gcggcgaccg agttgctctt gcccggcgtc aatacgggga atacccgcgc cacatagcag    4560
aactttaaaa gtgctcatca ttggaaaacg ttcttcgggg cgaaaactct caaggatctt    4620
accgctgttg agatccagtt cgatgtaacc cactcgtgca cccaactgat cttcagcatc    4680
ttttactttc accagcgttt ctgggtgagc aaaaacagga aggcaaaatg ccgcaaaaaa    4740
gggaataagg gcgacacgga aatgttgaat actcatactc ttcctttttc aatattattg    4800
aagcatttat cagggttatt gtctcatgag cggatacata tttgaatgta tttagaaaaa    4860
taaacaaata ggggttccgc gcacatttcc ccgaaaagtg ccacctgacg tctaagaaac    4920
cattattatc atgacattaa cctataaaaa taggcgtatc acgaggccct ttcgtctcgc    4980
gcgtttcggt gatgacggtg aaaacctctg acacatgcag ctcccggaga cggtcacagc    5040
ttgtctgtaa gcggatgccg ggagcagaca agcccgtcag ggcgcgtcag cgggtgttgg    5100
cgggtgtcgg ggctggctta actatgcggc atcagagcag attgtactga gagtgcacca    5160
tatgcggtgt gaaataccgc acagatgcgt aaggagaaaa taccgcatca ggaaatccaa    5220
catccaataa atcatacagg caaggcaaag aattagcaaa attaagcaat aaagcctcag    5280
agcataaagc taaatcggtt gtaccaaaaa cattatgacc ctgtaatact tttgcgggag    5340
aagcctttat ttcaacgcaa ggataaaaat ttttagaacc ctcatatatt ttaaatgcaa    5400
tgcctgagta atgtgtaggt aaagattcaa acgggtgaga aaggccggag acagtcaaat    5460
caccatcaat atgatattca accgttctag ctgataaatt catgccggag agggtagcta    5520
tttttgagag gtctctacaa aggctatcag gtcattgcct gagagtctgg agcaaacaag    5580
```

| | |
|---|---|
| agaatcgatg aacggtaatc gtaaaactag catgtcaatc atatgtaccc cggttgataa | 5640 |
| tcagaaaagc cccaaaaaca ggaagattgt ataagcaaat attttaaattg taaacgttaa | 5700 |
| tattttgtta aaattcgcgt taaattttg ttaaatcagc tcatttttta accaataggc | 5760 |
| cgaaatcggc aaaatccctt ataaatcaaa agaatagacc gagatagggt tgagtgttgt | 5820 |
| tccagtttgg aacaagagtc cactattaaa gaacgtggac tccaacgtca aagggcgaaa | 5880 |
| aaccgtctat cagggcgatg gcccactacg tgaaccatca ccctaatcaa gttttttggg | 5940 |
| gtcgaggtgc cgtaaagcac taaatcggaa ccctaaaggg agccccgat ttagagcttg | 6000 |
| acggggaaag ccggcgaacg tggcgagaaa ggaagggaag aaagcgaaag gagcgggcgc | 6060 |
| tagggcgctg gcaagtgtag cggtcacgct gcgcgtaacc accacacccg ccgcgcttaa | 6120 |
| tgcgccgcta cagggcgcgt actatggttg ctttgacgag cacgtataac gtgctttcct | 6180 |
| cgttagaatc agagcgggag ctaaacagga ggccgattaa agggatttta gacaggaacg | 6240 |
| gtacgccaga atcctgagaa gtgttttat aatcagtgag gccaccgagt aaaagagtct | 6300 |
| gtccatcacg caaattaacc gttgtcgcaa tacttctttg attagtaata acatcacttg | 6360 |
| cctgagtaga agaactcaaa ctatcggcct tgctggtaat atccagaaca atattaccgc | 6420 |
| cagccattgc aacaggaaaa acgctcatgg aaatacctac attttgacgc tcaatcgtct | 6480 |
| ggaaatccat tcgccattca ggctgcgcaa ctgttgggaa gggcgatcgg tgcgggcctc | 6540 |
| ttcgctatta cgccagctgg cg | 6562 |

<210> SEQ ID NO 7
<211> LENGTH: 537
<212> TYPE: DNA
<213> ORGANISM: homo sapiens

<400> SEQUENCE: 7

| | |
|---|---|
| cctcatggag ctcctcctgt cagaggagtg tggggactgg atgactccag aggtaacttg | 60 |
| tgggggaacg aacaggtaag gggctgtgtg acgagatgag agactgggag aataaaccag | 120 |
| aaagtctcta gctgtccaga ggacatagca cagaggccca tggtccctat ttcaaaccca | 180 |
| ggccaccaga ctgagctggg accttgggac agacaagtca tgcagaagtt aggggacctt | 240 |
| ctcctccctt ttcctggatc ctgagtacct ctcctccctg acctcaggct tcctcctagt | 300 |
| gtcaccttgg cccctcttag aagccaatta ggccctcagt ttctgcagcg gggattaata | 360 |
| tgattatgaa caccccccaat ctcccagatg ctgattcagc caggagctta ggaggggag | 420 |
| gtcactttat aagggtctgg gggggtcaga acccagagtc atccagctgg agccctgagt | 480 |
| ggctgagctc aggccttcgc agcattcttg ggtgggagca gccacgggtc agccaca | 537 |

<210> SEQ ID NO 8
<211> LENGTH: 121
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---|
| taaaacgacg gccagtgaat tcatatttgc atgtcgctat gtgttctggg aaatcaccat | 60 |
| aaacgtgaaa tgtctttgga tttgggaatc ttataagttc tgtatgagac cactcggatc | 120 |
| c | 121 |

<210> SEQ ID NO 9
<211> LENGTH: 47

```
<212> TYPE: DNA
<213> ORGANISM: Artificial Sequence
<220> FEATURE:
<223> OTHER INFORMATION: Synthetic Polynucleotide

<400> SEQUENCE: 9
gtggcattct acatcttcat tcaagagatg aagatgtaga atgccac            47

<210> SEQ ID NO 10
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 10
ugaagaugua gaaugccacu u                                         21

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
gtggcttttt atatattca                                            19

<210> SEQ ID NO 12
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 12
cugccuacau guuucugcu                                            19

<210> SEQ ID NO 13
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 13
ccuacauguu ucugcugau                                            19

<210> SEQ ID NO 14
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 14
guggcauucu acaucuuca                                            19

<210> SEQ ID NO 15
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 15
```
guggcuuuuu auauauuca                                          19

<210> SEQ ID NO 16
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 16
ggugguccug gc                                                 12

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
acaagacggg tgtggtgcgc                                         20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
tcatgggcgt cgccttcacc                                         20

<210> SEQ ID NO 19
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 19
ccatcaactt cctcacgctc ta                                      22

<210> SEQ ID NO 20
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 20
taggttgagc aggatgtagt tgaga                                   25

<210> SEQ ID NO 21
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 21
cugccuacau guuucugcu                                          19

<210> SEQ ID NO 22
<211> LENGTH: 19
<212> TYPE: RNA
<213> ORGANISM: Artificial Sequence -continued
<220> FEATURE:
<223> OTHER INFORMATION: Synthetic Polynucleotide

<400> SEQUENCE: 22
agcagaaaca uguaggcag                                                      19

<210> SEQ ID NO 23
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 23
ccuacauguu ucugcugau                                                      19

<210> SEQ ID NO 24
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 24
aucagcagaa acauguagg                                                      19

<210> SEQ ID NO 25
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 25
gcauggucau caucauggu                                                      19

<210> SEQ ID NO 26
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 26
accaugauga ugaccaugc                                                      19

<210> SEQ ID NO 27
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 27
cugccuacau guuucugcuu ucaagagaag cagaaacaug uaggcag                       47

<210> SEQ ID NO 28
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 28
ccuacauguu ucugcugauu ucaagagaau cagcagaaac auguagg                       47

```
<210> SEQ ID NO 29
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 29
gcauggucau caucaugguu ucaagagaac caugaugaug accaugc        47

<210> SEQ ID NO 30
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 30
cacacccgtc gcattgga                                         18

<210> SEQ ID NO 31
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 31
gtacgcagcc acttcgagta c                                     21

<210> SEQ ID NO 32
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 32
attctacatc                                                  10

<210> SEQ ID NO 33
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 33
tttttatata                                                  10

<210> SEQ ID NO 34
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 34
atatattcac ccaccagggc tccaac                                26

<210> SEQ ID NO 35
<211> LENGTH: 23
<212> TYPE: DNA
<213> ORGANISM: Artificial Sequence
<220> FEATURE:
<223> OTHER INFORMATION: Synthetic Polynucleotide
```

```
<400> SEQUENCE: 35
aaaaagccac gctggcgtag ggc                                           23

<210> SEQ ID NO 36
<211> LENGTH: 49
<212> TYPE: RNA
<213> ORGANISM: Artificial Sequence
<220> FEATURE:
<223> OTHER INFORMATION: Synthetic Polynucleotide

<400> SEQUENCE: 36
guggcauucu acaucuucau ucaagagaug aagauguaga augccacuu              49

<210> SEQ ID NO 37
<211> LENGTH: 49
<212> TYPE: RNA
<213> ORGANISM: Artificial Sequence
<220> FEATURE:
<223> OTHER INFORMATION: Synthetic Polynucleotide

<400> SEQUENCE: 37
cugccuacau guuucugcuu ucaagagaag cagaaacaug uaggcaguu              49

<210> SEQ ID NO 38
<211> LENGTH: 49
<212> TYPE: RNA
<213> ORGANISM: Artificial Sequence
<220> FEATURE:
<223> OTHER INFORMATION: Synthetic Polynucleotide

<400> SEQUENCE: 38
ccuacauguu ucugcugauu ucaagagaau cagcagaaac auguagguu              49

<210> SEQ ID NO 39
<211> LENGTH: 49
<212> TYPE: RNA
<213> ORGANISM: Artificial Sequence
<220> FEATURE:
<223> OTHER INFORMATION: Synthetic Polynucleotide

<400> SEQUENCE: 39
gcauggucau caucaugguu ucaagagaac caugaugaug accaugcuu              49

<210> SEQ ID NO 40
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 40
ccgtggcatt ctacatcttc at                                           22

<210> SEQ ID NO 41
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 41
ccgtggcatt ctacatcttc ata                                          23

<210> SEQ ID NO 42
```

-continued

```
<210> SEQ ID NO 42
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 42
cgtggcattc tacatcttca tt                                              22

<210> SEQ ID NO 43
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 43
tgaagatgta gaatgccact t                                               21

<210> SEQ ID NO 44
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 44
tgaagatgta gaatgccact tt                                              22

<210> SEQ ID NO 45
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 45
tgaagatgta gaatgccact tta                                             23

<210> SEQ ID NO 46
<211> LENGTH: 52
<212> TYPE: RNA
<213> ORGANISM: Artificial Sequence
<220> FEATURE:
<223> OTHER INFORMATION: Synthetic Polynucleotide

<400> SEQUENCE: 46
ccguggcauu cuacaucuuc auucaagaga ugaagaugua gaaugccacu uu             52

<210> SEQ ID NO 47
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 47

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Ala Ala Leu Met Tyr Met Phe Val Ile Leu
        35                  40                  45

Leu Leu Gly Phe Phe Asn Ile Pro Leu Thr Leu Val Tyr Thr Val Gln
    50                  55                  60
```

```
His Lys Lys Leu Arg Thr Pro Leu Asn Tyr Ile Leu Ala Leu Asn Leu
 65             70                  75                  80
Val Ala Asp Val Met Phe Leu Leu Gly Gly Thr Ser Thr Phe Leu Tyr
             85                  90                  95
Thr Ser Leu His Gly Tyr Phe Val Phe Gly Pro Thr Gly Cys Asn Leu
            100                 105                 110
Phe Gly Glu Phe Ala Thr Leu Arg Gly Gly Ile Ala Leu Trp Val Leu
            115                 120                 125
Ser Val Leu Ala Ile Glu Arg Tyr Val Val Val Cys Lys Pro Met Ser
        130                 135                 140
Asn Phe Arg Phe Gly Glu Asn His Ala Ile Met Gly Phe Ala Val Thr
145             150                 155                 160
Trp Val Met Ala Leu Ala Cys Ala Ala Pro Pro Leu Ala Gly Trp Ser
                165                 170                 175
Arg Tyr Ile Pro Glu Gly Leu Gln Cys Ser Cys Gly Ile Asp Tyr Tyr
            180                 185                 190
Thr Leu Lys Pro Glu Val Asn Asn Glu Ser Phe Val Ile Tyr Val Phe
        195                 200                 205
Met Val His Phe Thr Met Pro Ile Ile Ile Ile Phe Tyr Cys Phe Gly
        210                 215                 220
Gln Leu Val Val Thr Phe Lys Glu Ala Ala Gln Gln Gln Glu Ser
225             230                 235                 240
Ala Thr Thr Gln Lys Ala Glu Lys Glu Val Thr Arg Met Val Ile Ile
                245                 250                 255
Met Val Ile Leu Phe Ala Ile Cys Trp Val Ala Tyr Pro Ser Val Ala
            260                 265                 270
Phe Tyr Ile Phe Thr His Gln Gly Ser Asn Phe Gly Pro Ile Phe Met
            275                 280                 285
Ala Pro Ile Thr Phe Phe Ala Ala Ala Ser Lys Ile Tyr Asn Tyr Ile
        290                 295                 300
Val Pro Ile Met Met Asn Lys Gln Phe Arg Asn Cys Met Leu Thr Thr
305             310                 315                 320
Ile Cys Cys Gly Lys Met Pro Leu Gly Asp Asp Glu Ala Ser Ala Thr
                325                 330                 335
Val Ser Lys Thr Glu Thr Ser Gln Val Ala Pro Ala
                340                 345
```